US007635695B2

(12) United States Patent
Burkitt et al.

(10) Patent No.: US 7,635,695 B2
(45) Date of Patent: Dec. 22, 2009

(54) ANTIINFLAMMATION AGENTS

(75) Inventors: Simon A. Burkitt, Kirkby-in-Ashfield (GB); Mario G. Cardozo, San Francisco, CA (US); Timothy D. Cushing, Pacifica, CA (US); Michael R. DeGraffenreid, San Francisco, CA (US); Christopher N. Farthing, Macclesfield (GB); Xiaolin Hao, Foster City, CA (US); Juan C. Jaen, Burlingame, CA (US); Xian Yun Jiao, San Mateo, CA (US); David J. Kopecky, San Francisco, CA (US); Marc Labelle, Burlingame, CA (US); Sarah E. Lively, Congleton (GB); Dustin L. McMinn, Pacifica, CA (US); Sven P. Rasmussen, Congleton (GB); Youngsook Shin, San Mateo, CA (US); Marie-Louise Smith, Half Moon Bay, CA (US); Andrew Smith, Macclesfield (GB)

(73) Assignee: Amgen Inc., South San Francisco, CA (US)

( * ) Notice: Subject to any disclaimer, the term of this patent is extended or adjusted under 35 U.S.C. 154(b) by 0 days.

(21) Appl. No.: 11/709,895

(22) Filed: Feb. 21, 2007

(65) Prior Publication Data

US 2007/0155777 A1    Jul. 5, 2007

Related U.S. Application Data

(62) Division of application No. 10/666,857, filed on Sep. 19, 2003, now Pat. No. 7,199,119.

(60) Provisional application No. 60/422,531, filed on Oct. 31, 2002.

(51) Int. Cl.
*A61K 31/5377* (2006.01)
*A61K 31/4365* (2006.01)
*C07D 413/14* (2006.01)
*C07D 495/04* (2006.01)

(52) U.S. Cl. .................... 514/233.8; 514/301; 544/127; 546/114

(58) Field of Classification Search ............... 514/233.8, 514/301; 546/114; 544/127
See application file for complete search history.

(56) References Cited

U.S. PATENT DOCUMENTS

| 3,845,065 | A | 10/1974 | Shen et al. |
| 3,903,095 | A | 9/1975 | Shen et al. |
| 6,022,884 | A | 2/2000 | Mantlo et al. |
| 6,649,654 | B1 | 11/2003 | Karin et al. |

FOREIGN PATENT DOCUMENTS

| WO | WO 95/02597 | 1/1995 |
| WO | WO 01/00610 | 1/2001 |
| WO | WO 01/30774 | 3/2001 |
| WO | WO 01/58890 | 8/2001 |
| WO | WO 01/58899 | 8/2001 |
| WO | WO 01/68648 | 9/2001 |
| WO | WO 02/28860 | 4/2002 |
| WO | WO 02/30353 | 4/2002 |
| WO | WO 02/30423 | 4/2002 |
| WO | WO 02/41843 | 5/2002 |
| WO | WO 02/44153 | 6/2002 |
| WO | WO 02/46171 | 6/2002 |
| WO | WO 02/060386 | 8/2002 |
| WO | WO 02/076985 | 10/2002 |
| WO | WO 02/094265 | 11/2002 |
| WO | WO 02/094322 | 11/2002 |
| WO | WO 02/094813 | 11/2002 |
| WO | WO 03/010158 | 2/2003 |
| WO | WO 03/024935 | 3/2003 |
| WO | WO 03/024936 | 3/2003 |
| WO | WO 03/027075 | 4/2003 |
| WO | WO 03/029242 | 4/2003 |
| WO | WO 03/035625 | 5/2003 |
| WO | WO 03/037886 | 5/2003 |
| WO | WO 03/039545 | 5/2003 |
| WO | WO 03/040131 | 5/2003 |
| WO | WO 03/070706 | 8/2003 |
| WO | WO 03/086309 | 10/2003 |
| WO | WO 03/084959 | 11/2003 |
| WO | WO 03/095430 | 11/2003 |
| WO | WO 03/103648 | 12/2003 |
| WO | WO 03/103658 | 12/2003 |
| WO | WO 03/103661 | 12/2003 |
| WO | WO 03/104218 | 12/2003 |
| WO | WO 03/104219 | 12/2003 |
| WO | WO 2004/009582 | 1/2004 |

OTHER PUBLICATIONS

Vippagunta et al., Crystalline solids, 2001, Advanced Drug Delivery Reviews, 48, pp. 3 and 18.*

(Continued)

*Primary Examiner*—Kamal A Saeed
*Assistant Examiner*—Kristin Bianchi
(74) *Attorney, Agent, or Firm*—Jones Day

(57) ABSTRACT

Compounds, compositions and methods that are useful in the treatment of inflammatory, immunoregulatory, metabolic, infectious and cell proliferative diseases or conditions are provided herein. In particular, the invention provides compounds which modulate the expression and/or function of proteins involved in inflammation, metabolism, infection and cell proliferation. The subject compounds contain a fused heterobicyclic ring.

20 Claims, 7 Drawing Sheets

OTHER PUBLICATIONS

Wolff et al., Burger's Medicinal Chemistry and Drug Discovery, 1994, Wiley-Interscience, Fifth Edition, vol. I: Principles and Practice, pp. 975-977.*

Adha, et al., "Synthesis of Complex Ethynyladenosines Using Organic Triflic Enolates in Palladium-Catalyzed Reactins: Potential Agonists for the Adenisone $A_2$ Receptor" Tetrahedron, vol. 53, No. 20; pp. 2747-6754, (1997).

Baichwal & Baeuerle, "Apoptosis: Activate NF-KB or die?" Current Biology, 7:R94-R96 (1997).

Comins, D. L. et al., "Lithiation of Heterocycles Directed by α-Amino Alkoxides" J. Org Chem. 52; pp. 104-109 (1987).

Eloy, F. and Deryckere, A., "Thienopyridines" Bulletin des Societes Chimiquest Belges; pp. 301-311 (1970) (English Abstract Provided at C05).

English Abstract of C04. Eloy, F., and Deryckere, A. "Thienopyridines" Bulletin des Societes chimiquest Belges 79, 301-311 (1970).

Gjoes et al., "Some Substitution Reactions of 2-Phenylthiophene" Acta Chemica Scandinavica, vol. 26, No. 5, 1751-2162 (1972).

Hehner, S.P. et al., "The anti-inflammatory sesquiterprene lactone parthenolide inhibits NV-kB by targeting the 1kB kinase complex", J. Immunol., vol. 163; pp. 5617-5623 (1999).

Junek, H., et al., "Synthesen von Alkyl-bzw. Cycloalkylpyridinen and Naphthyridinen," *Monatshefte fuer Chemie.*; vol. 108, No. 3; pp. 689-702 (1977) (English Abstract Provided at C9).

English Abstract of C08. Junek, H., et al., "Report on the chemistry of enaminoketones, part 13, Syntheses of alkyl-cycloalklpyridines, and naphthyridines", Montashefte fuer chemie, vol. 108, No. 3, pp. 689-702 (1977).

Karin, J., "The beginning of the End: IkB Kinase (Ikk) and NF-kB Activation", The Journal of Biological Chemistry, vol. 274, No. 39, pp. 27339-27342, Issue of Sep. 24, 1999.

Koitz, G. et al., "Condensation products of dimeric malononitrile derivatives with 2,4-diketones and their application for the synthesis of substituted 1,6-naphtyridines", Heterocycles, vol. 20, No. 12; pp. 2405-2409 (1983).

Malinin, N. et al., "MAP3K-related kinase involved in NF-kB induction by TNF, CD95 and IL-1", Nature, vol. 385, pp. 540-544 (1997).

Mercurio, F., et al, "IKK-1 and IKK-2: Cytokine-Activated IkB Kinases Essential for NF-kB Activation", Science, vol. 278; pp. 1054-1068 (1997).

Poirier, Y. et al, "Composes sulfures heterocycliques. Xx(*). —Sulfration d'alcoylidene cyclopentanones" Bulletin de la Societe Chimique de France; pp. 1054-1068 (1966) (English Abstract Provided at C15).

English Abstract of C14. Poirier, Y. et al, "Heterocyclic sulfur compounds. xx. Sulfuration of alkl-idenecyclopentanones" Bulletin de la Societe Chimique de France; pp. 1052-1068 (1966).

Silberg, A., et al., "Beitrage zum Studium der Thiazole, VIII" Chem. Ber, 97(6); pp. 1684-1687, (1964) (English Abstract Provided at C17).

English Abstract of C16. Silberg, A., et al., "Thiazoles. VIII. Phenylthiazolecarboxaldehydes" Chem. Ber, 97(6); pp. 1684-1687, (1964).

Silverman, J. et al., "3840 In Vitro and in vivo activity of SPC-595, a novel cell cycle inhibitory cytotoxic in murine syngeneic and human xenograft tumor models" Presentation at the 95th American Association for Cancer Research, Mar. 27-31, 2004.

Skorcz, J. A., Suh, J.T.; Germershausen, R. L. J. Heterocyclic, vol. 10; pp. 249-253 (1973).

Verma, et al., Genes & Development, vol. 9, No. 22; pp. 2723-2872 (1995).

Woronicz, J.D., et al., "1κβ: Nf-κB Activation and complex Formation with IκB Kinase-α and NIK" Science, vol. 278; Oct. 31, 1997.

Zhang, Y., Homfeldt, A.-B; Gronowitz, S.; Stalhandske C. "Pyridine-Substituted Hydroxythiophenes. III. Dimerization of 3-(2-Pyridyl)thiophen-2(5H)-one from Demethylation Reaction of 2-Methoxy-3-(2-pyridyl)thiophene. X-Ray Structure Determination of (±)-(3R*, 4S*)-3-(2-Pyridyl)-4-[2-oxo-3(1,2-dihydropyridin-2-ylidene)-2,3-dihydro-thiophen-5-yl]-4,5-dihydrothiophen-2(3H)-one" Acta Chemica Scand. vol. 48; pp. 843-849 (1994).

* cited by examiner

ANTIINFLAMMATION AGENTS

CROSS-REFERENCES TO RELATED APPLICATIONS

This application is a divisional application of U.S. patent application Ser. No. 10/666,857, filed Sep. 19, 2003 now U.S. pat. No. 7,199,119, which claims the benefit of U.S. Provisional Application Ser. No. 60/422,531, filed Oct. 31, 2002 (entitled "Antiinflammation Agents" Ref. No. T02-008-2/US), the contents of each of which are incorporated herein by reference in their entireties.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Tumor Necrosis Factor (TNF) and interleukin-1 (IL-1) are cytokines that have been implicated in a wide range of biological processes, including inflammation. The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, septic shock, inflammatory bowel disease, bone mass loss, cancer, dermal sensitization disorders, diabetes, obesity and neurological conditions such as ischemic stroke, closed-head injuries, etc.

Cytokines trigger a variety of changes in gene expression in their target cells by binding and activating their respective cognate receptors. Receptor activation sets in motion certain biochemical events, including the activation of otherwise latent transcription factors. Members of the NF-κB Rel family of transcription factors represent some of the most prominent of these transcription factors, having been implicated in the regulation of genes involved in inflammation, cell proliferation, apoptosis, and several other basic cellular functions (Verma et al. *Genes Dev.* 9, 2723 (1995); Baichwal & Baeuerle, *Curr. Biol.* 7, 94 (1997)).

The best studied member of this family of transcription factors is NF-κB, which generally exists in cells as a heterodimer of two proteins: p50 (NF-κB1) and p65 (RelA), although homodimers of these individual components are also possible (Baeuerle and Baltimore, *Cell*, 53, 211 (1988); Baeuerle and Henkel, *Annu. Rev. Immunol.* 12, 141 (1994)). NF-κB, in its inactive form, resides in the cytoplasm of cells. In response to various types of stimuli, such as proinflammatory cytokines (e.g., TNF and IL-1), ultraviolet irradiation and viral infection (Verma, 1995; Baichwal, 1997; Cao et al. *Science*, 271, 1128 (1996)) NF-κB migrates to the nucleus.

In its inactive state, the NF-κB heterodimer is held in the cytoplasm by association with inhibitory IκB proteins. Recently, the three-dimensional structure of a NF-κB/IκB ternary complex has been solved (Huxford et al. *Cell*, 95, 759 (1998); Jacobs et al. *Cell*, 95, 749 (1998)). When cells are treated with the appropriate stimuli, such as IL-1 or TNF, intracellular signal transduction pathways are activated that lead to the eventual phosphorylation of IκB proteins on two specific residues (serines 32 and 36 in IκBα, serines 19 and 23 in IκBβ). Mutation of one or both serine residues renders IκB resistant to cytokine-induced phosphorylation. This signal-induced phosphorylation targets IκB for ubiquitination and proteosome-mediated degradation, allowing nuclear translocation of NF-κB (Thanos and Maniatis, *Cell*, 80, 529 (1995)). The only regulated step in the IκB degradation pathway is the phosphorylation of IκB by IκB kinases (IKK) (Yaron et al. *EMBO J.* 16, 6486 (1997)).

Several intermediate steps in the TNF- and IL-1-activated signaling pathways that result in IκB phosphorylation have been elucidated in recent years. Both pathways appear to merge at the level of the protein kinase NIK (NF-κB-inducing kinase) (Malinin et al. *Nature*, 385, 540 (1997); Song et al. *Proc. Natl. Acad. Sci. USA*, 94, 9792 (1997)). Similarly, the protein kinases MEKK1 and MLK3 have been implicated in the induction of IKK activity (Lee et al. *Proc. Natl. Acad. Sci. USA*. 95, 9319 (1998); Hehner et al. *Mol. Cell. Biol.* 20, 2556 (2000)). While the specific details remain somewhat unclear regarding how these or other intermediate proteins may interact with and/or stimulate IKK activity in cells, significant progress has been made in elucidating the enzymes responsible for IκB phosphorylation.

Two IKK enzymes, generally referred to as IKKα (or IKK-1) and IKK β (or IKK-2) (Woronicz et al. *Science*, 278, 866 (1997); Zandi et al. *Cell*, 91, 243 (1997); Mercurio et al. *Science*, 278, 860 (1997)) have been discovered. Both forms of IKK can exist as homodimers and as IKKα/IKKβ heterodimers. Another recently discovered component of the IκB kinase complex is a regulatory protein, known as IKK-gamma or NEMO (NF-κB-Essential Modulator) (Rothwarf et al. *Nature*, 395, 297 (1998)). NEMO does not contain a catalytic domain, and thus it appears to have no direct kinase activity and it probably serves a regulatory function. Existing data suggest that the predominant form of IKK in cells is an IKKα/IKKβ heterodimer associated with either a dimer or a trimer of NEMO (Rothwarf et al. *Nature* 395, 297 (1998)).

Biochemical and molecular biology experiments have clearly identified IKKα and IKKβ, as the most likely mediators of TNF- and IL-1-induced IκB phosphorylation and degradation, which results in NF-κB activation and upregulation of families of genes involved in inflammatory processes (Woronicz et al. *Science (*1997); Karin, Oncogene 18, 6867 (1999); Karin, *J. Biol. Chem.* 274, 27339 (1999)). These kinases have also been identified as components of CD40 ligand-induced signaling. IKKα and IKKβ have very similar primary structures, displaying more than 50% overall sequence identity. In the kinase domain, their sequences are 65% identical.

Based on our present understanding of the critical role played by TNF and IL-1 in the wide array of pathological conditions described above, and the involvement of IKKα and IKKβ in the signal transduction of both cytokines, the discovery of small molecules that potently and selectively inhibit either of these kinases would result in a major advancement in the therapy of those conditions. In this application we describe novel compounds which display such desirable activity.

BRIEF SUMMARY OF THE INVENTION

The present invention provides compounds useful in the treatment or prevention of inflammatory, metabolic, infectious or cell proliferative diseases or conditions, having the formula (I):

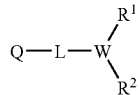
I wherein

W is a 5-6, 6-6 or 5-5 or fused bicyclic ring system, wherein one or both rings are aromatic, containing a nitrogen atom and from 0 to 3 additional heteroatoms selected from the group consisting of N, O and S, wherein (i) the ring fusion atoms are independently CH or N, with the proviso that the ring fusion atoms are not both N; and (ii) the atoms to which L, $R^1$ and $R^2$ are attached are independently selected from the group consisting of =C—, —CH— and —N—;

$R^1$ is selected from the group consisting of —C(O)NR$^{1a}$R$^{1b}$, —C(O)R$^{1a}$, —CH(=NOH), —N(R$^{1b}$)C(O)R$^{1a}$, —SO$_2$NR$^{1a}$R$^{1b}$, —SO$_2$R$^{1a}$, —C(O)N(R$^{1a}$)OR$^{1b}$, —(C$_1$-C$_4$)alkylene-N(R$^{1b}$)C(O)R$^{1a}$, —(C$_1$-C$_4$)alkylene-C(O)NR$^{1a}$R$^{1b}$ and heteroaryl; wherein R$^{1a}$ and R$^{1b}$ are selected from hydrogen, (C$_1$-C$_6$)alkyl, (C$_2$-C$_4$)alkenyl, (C$_2$-C$_6$)heteroalkyl, hydroxy(C$_1$-C$_4$)alkyl, fluoro(C$_1$-C$_4$)alkyl, cyano(C$_1$-C$_4$) alkyl, cyclo(C$_3$-C$_8$)alkyl, mono- or di-hydroxycyclo(C$_3$-C$_8$) alkyl, heterocyclo(C$_3$-C$_8$)alkyl, heterocyclo(C$_3$-C$_8$)alkyl-(C$_1$-C$_4$)alkyl; and optionally, R$^{1a}$ is attached to an adjacent ring member of W relative to the point of attachment of R$^1$ to form an additional 5- or 6-membered fused ring, or R$^{1a}$ and R$^{1b}$ are combined with their intervening atoms to form a 3-, 4-, 5- or 6-membered ring.

$R^2$ is selected from the group consisting of —NR$^{2a}$R$^{2b}$ and —OH; wherein R$^{2a}$ and R$^{2b}$ are selected from hydrogen, (C$_1$-C$_6$)alkyl, (C$_2$-C$_4$)alkenyl, (C$_2$-C$_6$)heteroalkyl, hydroxy (C$_1$-C$_4$)alkyl, fluoro(C$_1$-C$_4$)alkyl, cyano(C$_1$-C$_4$)alkyl, cyclo (C$_3$-C$_8$)alkyl, mono- or di-hydroxycyclo(C$_3$-C$_8$)alkyl, heterocyclo(C$_3$-C$_8$)alkyl, heterocyclo(C$_3$-C$_8$)alkyl-(C$_1$-C$_4$) alkyl, aryl, aryl(C$_1$-C$_4$)alkyl, heteroaryl, heteroaryl(C$_1$-C$_4$) alkyl, —C(O)—(C$_1$-C$_4$)alkyl, —C(O)—(C$_1$-C$_4$)alkoxy, —C(O)-heterocyclo(C$_3$-C$_8$)alkyl and C(O)-fluoro(C$_1$-C$_4$) alkyl; and optionally, R$^{2a}$ and R$^{2b}$ may be combined with the nitrogen atom to which each is attached to form a 5-, 6- or 7-membered ring containing from 1-3 heteroatoms selected from N, O and S.

L is a divalent linkage selected from the group consisting of a single bond, (C$_1$-C$_4$)alkylene, —C(O)—, —C(O)N(R$^3$)—, —SO$_2$N(R$^3$)—, —C(R$^3$)=C(R$^4$)—, —O—, —S— and —N(R$^3$)—; wherein R$^3$ and R$^4$ are independently selected from the group consisting of hydrogen, (C$_1$-C$_6$)alkyl, cyclo (C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl.

Q is selected from the group consisting of (C$_2$-C$_6$)alkenyl, (C$_2$-C$_6$)alkynyl, (C$_1$-C$_6$)alkoxy, halogen, aryl, aryl(C$_1$-C$_4$) alkyl, heteroaryl, cyclo(C$_3$-C$_8$)alkyl, cyclo(C$_5$-C$_8$)alkenyl and heterocyclo(C$_3$-C$_8$)alkyl; each of which is optionally substituted as indicated below.

Within the above compounds of formula I, the compound is other than

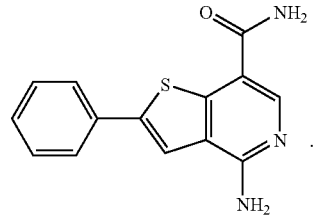

The invention also provides compounds useful in the treatment or prevention of inflammatory, metabolic, infectious or cell proliferative diseases or conditions, having a formula selected from the group consisting of:

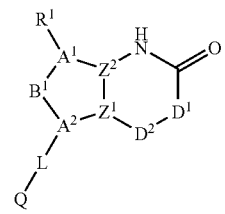
VIIa.1

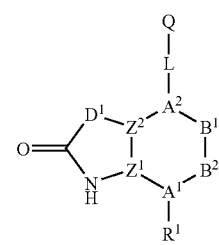
VIIa.2

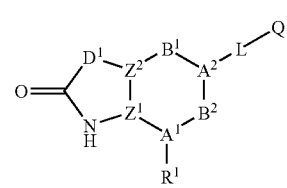
VIIa.3

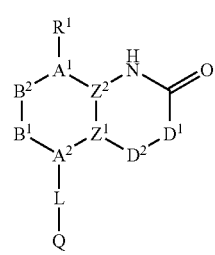
VIIb.1

-continued

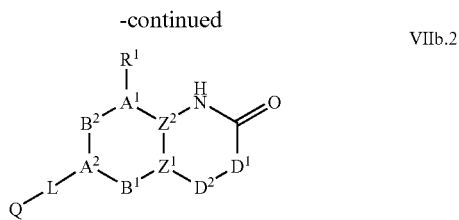

VIIb.2 wherein

R$^1$ is selected from the group consisting of —C(O)NR$^{1a}$R$^{1b}$, —C(O)R$^{1a}$, —CH(=NOH), —N(R$^{1b}$)C(O)R$^{1a}$, —SO$_2$NR$^{1a}$R$^{1b}$, —SO$_2$R$^{1a}$, —C(O)N(R$^{1a}$)OR$^{1b}$, —(C$_1$-C$_4$)alkylene-N(R$^{1b}$)C(O)R$^{1a}$, —(C$_1$-C$_4$)alkylene-C(O)NR$^{1a}$R$^{1b}$ and heteroaryl; wherein R$^{1a}$ and R$^{1b}$ are selected from hydrogen, (C$_1$-C$_6$)alkyl, (C$_2$-C$_4$)alkenyl, (C$_2$-C$_6$)heteroalkyl, hydroxy(C$_1$-C$_4$)alkyl, fluoro(C$_1$-C$_4$)alkyl, cyano(C$_1$-C$_4$)alkyl, cyclo(C$_3$-C$_8$)alkyl, mono- or di-hydroxycyclo(C$_3$-C$_8$)alkyl, heterocyclo(C$_3$-C$_8$)alkyl, heterocyclo(C$_3$-C$_8$)alkyl-(C$_1$-C$_4$)alkyl; and optionally, R$^{1a}$ is attached to an adjacent ring member of W relative to the point of attachment of R$^1$ to form an additional 5- or 6-membered fused ring, or R$^{1a}$ and R$^{1b}$ are combined with their intervening atoms to form a 3-, 4-, 5- or 6-membered ring.

L is a divalent linkage selected from the group consisting of a single bond, (C$_1$-C$_4$)alkylene, —C(O)—, —C(O)N(R$^3$)—, —SO$_2$N(R$^3$)—, —C(R$^3$)=C(R$^4$)—, —O—, —S— and —N(R$^3$)—; wherein R$^3$ and R$^4$ are independently selected from the group consisting of hydrogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl.

Q is selected from the group consisting of (C$_2$-C$_6$)alkenyl, (C$_2$-C$_6$)alkynyl, (C$_1$-C$_6$)alkoxy, halogen, aryl, aryl(C$_1$-C$_4$)alkyl, heteroaryl, cyclo(C$_3$-C$_8$)alkyl, cyclo(C$_5$-C$_8$)alkenyl and heterocyclo(C$_3$-C$_8$)alkyl; each of which is optionally substituted as indicated below.

A$^1$ and A$^2$ are independently selected from the group consisting of =C—, —CH— and —N—;

B$^1$ and B$^2$ are independently selected from the group consisting of =C(R$^{5a}$)—, —C(R$^5$)(R$^6$)—, —C(O)—, =N—, —N(R$^5$)—, —O— and —S(O)$_m$—;

D$^1$ is selected from the group consisting of —C(R$^7$)(R$^8$)—, —N(R$^7$)— and —O—;

D$^2$ is selected from the group consisting of —C(R$^9$)(R$^{10}$)—, —C(O)—, —N(R$^9$)—, —O— and —S(O)$_n$—;

optionally, D$^1$-D$^2$ may be —(R$^{11}$)=C(OR$^{12}$)— or —C(R$^{11}$)=N—;

Z$^1$ and Z$^2$ are independently CH or N;

R$^3$, R$^4$, R$^5$, R$^6$, R$^7$, R$^8$, R$^9$ and R$^{10}$ are independently selected from the group consisting of hydrogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl;

R$^{5a}$, in each instance is independently selected from the group consisting of hydrogen, halogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl;

R$^{11}$ and R$^{12}$ are independently selected from the group consisting of hydrogen and (C$_1$-C$_6$)alkyl, aryl and aryl(C$_1$-C$_4$)alkyl.

The subscripts m and n are independently an integer of from 0 to 2; with the proviso that D$^1$ and D$^2$ are not both —N(R$^9$)— or —O—.

Unless otherwise indicated, the compounds provided in the above formula are meant to include pharmaceutically acceptable salts, hydrates, solvates and prodrugs thereof.

In another aspect, the present invention provides pharmaceutical compositions comprising one or more compounds of the invention and pharmaceutically acceptable carrier, excipient or diluent.carrier or excipient.

In yet another aspect, provides methods for the treatment or prevention of an inflammatory, metabolic, infectious or cell proliferative disease or condition, comprising administering to a subject in need thereof a compound of the invention.

Other objects, features and advantages of the present invention will become apparent to those skilled in the art from the following description and claims.

DETAILED DESCRIPTION OF THE INVENTION

Abbreviations and Definitions

Figure 1:
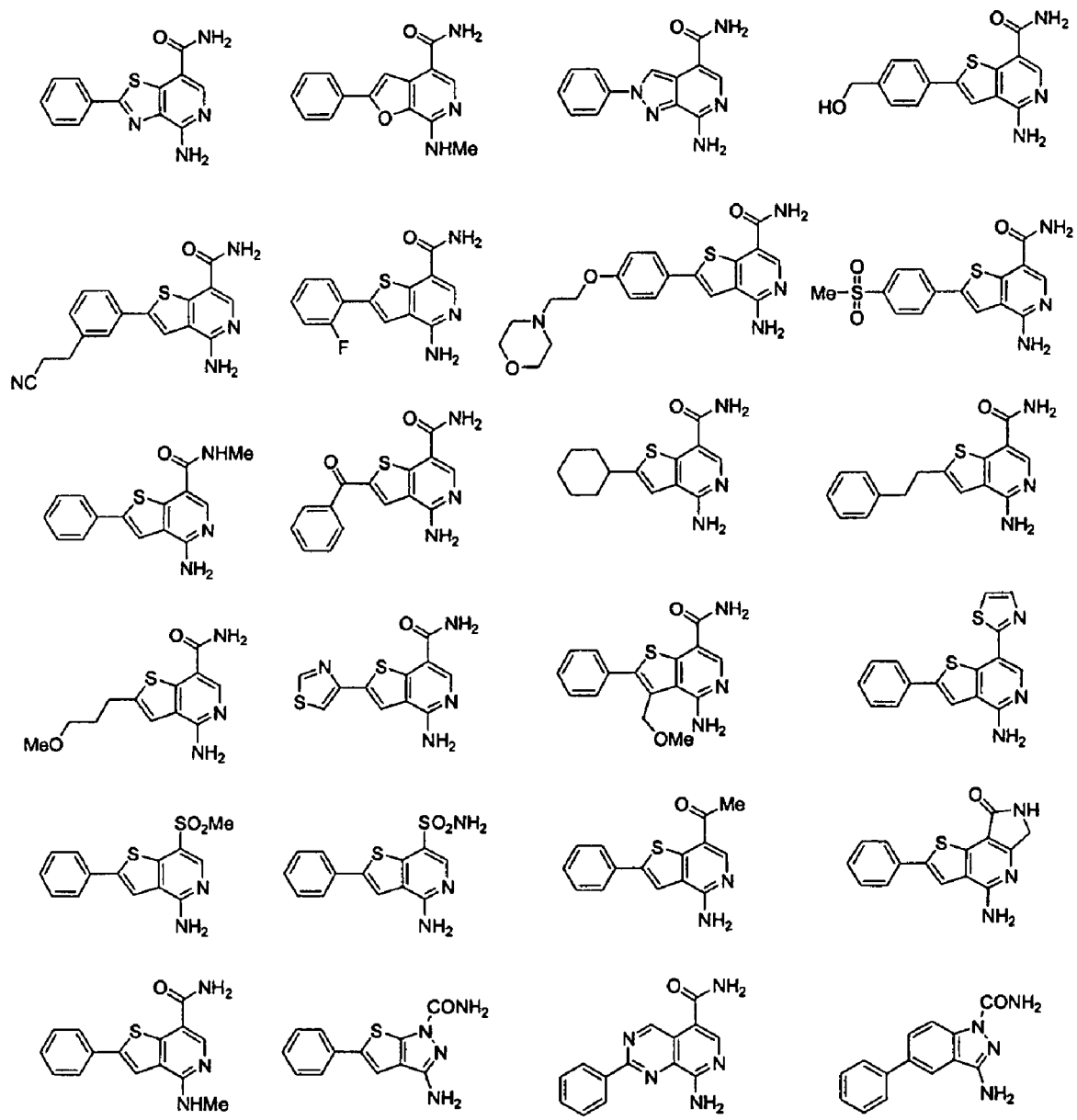
FIGS. 1-7 provides structures for selected compounds of the invention.

The abbreviations used herein are conventional, unless otherwise defined.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Cardiovascular disorders, such as hypertension and coronary artery disease, and metabolic disorders, such as hyperlidemia and diabetes, are commonly associated with obesity.

As used herein, "diabetes" refers to type I diabetes mellitus (juvenile onset diabetes, insulin dependent-diabetes mellitus or IDDM) or type II diabetes mellitus (non-insulin-dependent diabetes mellitus or NIDDM), preferably, NIDDM.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "eating disorder" refers to an emotional and/or behavioral disturbance associated with an excessive decrease in body weight and/or inappropriate efforts to avoid weight gain, e.g., fasting, self-induced vomiting, laxative or diuretic abuse. Exemplary eating disorders include anorexia nervosa and bulimia.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "signal transduction", "signaling" and related terms refer to a process whereby an extracellular signal (e.g, the concentration of a cytokine, hormone, neurotransmitter, growth factor) is transmitted via a cascade of intracellular protein-protein interactions and generates one or more cellular responses (e.g., gene transcription, protein secretion, mitosis, apoptosis). The interaction of an extracellular signaling molecule (e.g, a cytokine, a hormone, a neurotransmitter, a growth factor) with one or more transmembrane protein receptors at the cell surface can activate one or more signal transduction pathways. The protein-protein interactions in a signal transduction pathway may be multivalent and include covalent and/or non-covalent protein modification. An intracellular signaling molecule, i.e., a signal transducing protein or a signal transducer, may be involved in one or more signal transduction pathways. As described herein, protein-protein interactions includes direct and indirect interactions.

As used herein, the term "IKK" refers to an I-κB kinase protein or variant thereof that is capable of mediating a cellular response to IL-1 in vitro or in vivo. IKK may be capable of transphosphorylation of other proteins or autophosphorylation. In preferred embodiments, IKK is IKKβ and/or IKKα.

IKK variants include proteins substantially homologous to native IKK, i.e., proteins having one or more naturally or non-naturally occurring amino acid deletions, insertions or substitutions (e.g., IKK derivatives, homologs and fragments). The amino acid sequence of an IKK variant preferably is at least about 80% identical to a native IKK, more preferably at least about 90% identical, and most preferably at least about 95% identical.

As used herein, the term "IRAK" refers to an interleukin-1 (IL-1) receptor-associated kinase protein or variant thereof that is capable of mediating a cellular response to IL-1 in vitro or in vivo. IRAK may be kinase-active or kinase-inactive. Exemplary kinase active IRAKs include IRAK-1 and IRAK-4. Exemplary kinase inactive IRAKs include IRAK-2 and IRAK-3 (also known as IRAK-M). Kinase-active IRAKs may be capable of transphosphorylation of other proteins or autophosphorylation. In preferred embodiments, IRAK is IRAK-1 and/or IRAK-4.

IRAK variants include proteins substantially homologous to native IRAK, i.e., proteins having one or more naturally or non-naturally occurring amino acid deletions, insertions or substitutions (e.g., IRAK derivatives, homologs and fragments). The amino acid sequence of an IRAK variant preferably is at least about 80% identical to a native IRAK, more preferably at least about 90% identical, and most preferably at least about 95% identical.

"Acyl" or "alkanoyl" means the group C(O)R', where R' is hydrogen, alkyl, cycloalkyl, cycloalkyl-alkyl, aryl, arylalkyl, and variations of these groups in which one or more carbon atoms have been replaced with heteroatoms.

"Alkyl" means a linear saturated monovalent hydrocarbon radical or a branched saturated monovalent hydrocarbon radical having the number of carbon atoms indicated in the prefix. For example, $(C_1-C_6)$alkyl is meant to include methyl, ethyl, n-propyl, 2-propyl, tert-butyl, pentyl, and the like. For each of the definitions herein (e.g., alkyl, alkenyl, alkoxy, arylalkyloxy), when a prefix is not included to indicate the number of main chain carbon atoms in an alkyl portion, the radical or portion thereof will have six or fewer main chain carbon atoms.

"Alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2-C_6)$alkenyl is meant to include, ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, $(C_2-C_6)$alkynyl is meant to include ethynyl, propynyl, and the like.

"Alkoxy", "aryloxy", "arylalkyloxy", "heteroalkyloxy" or "heteroarylalkyloxy" means a radical —OR where R is an alkyl, aryl, arylalkyl, heteroalkyl or heteroarylalkyl respectively, as defined herein, e.g., methoxy, phenoxy, benzyloxy, pyridin-2-ylmethyloxy, and the like.

"Aryl" means a monovalent monocyclic or bicyclic aromatic hydrocarbon radical of 6 to 10 ring atoms which is substituted independently with one to four substituents, preferably one, two, or three substituents selected from, for example, alkyl, cycloalkyl, cycloalkyl-alkyl, halo, nitro, cyano, hydroxy, alkoxy, amino, acylamino, monoalkylamino, dialkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), —CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, heteroalkyl, phenyl or phenylalkyl), or —NR"C(O)R', —NR"CO$_2$R', —NR'C(O)NR"R'", —SO$_2$R', —SO$_2$NR'R" or —OC(O) NR'R" (where R', R" and R'"are independently hydrogen, alkyl, cycloalkyl, aryl, arylalkyl, —C(O)-alkyl, —CO$_2$-alkyl, —C(O)-heterocycloalkyl, —C(O)-fluoroalkyl, and heteroaryl). Optionally, two groups R', R", R'", R$^a$ or R$^b$ attached to a common nitrogen atom can be combined with the nitrogen atom to form a 3-, 4-, 5-, 6-, or 7-membered ring having from 1-3 heteroatoms selected from N, O and S. Two of the substituents on adjacent atoms of the aryl ring may optionally be replaced with a substituent of the formula -T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl, ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $(C_1-C_6)$alkyl. More specifically the term aryl includes, but is not limited to, phenyl, biphenyl, 1-naphthyl, and 2-naphthyl, and the substituted derivatives thereof.

"Arylalkyl" means a radical —$R^aR^b$ where $R^a$ is an alkylene group (having six or fewer main chain carbon atoms) and $R^b$ is an aryl group as defined herein, e.g., benzyl, phenylethyl, 3-(3-chlorophenyl)-2-methylpentyl, and the like.

"Arylheteroalkyl" means a radical —$R^aR^b$ where $R^a$ is an heteroalkylene group and $R^b$ is an aryl group as defined herein, e.g., 2-hydroxy-2-phenyl-ethyl, 2-hydroxy-1-hydroxymethyl-2-phenyl-ethyl, and the like.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, monoalkylamino, dialkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkyl-alkyl" means a radical —$R^aR^b$ where $R^a$ is an alkylene group and $R^b$ is a cycloalkyl group as defined herein, e.g., cyclopropylmethyl, cyclohexylpropyl, 3-cyclohexyl-2-methylpropyl, and the like.

"Haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I. The term "fluoroalkyl" means alkyl substituted with one or more same or different fluorine atoms, e.g., —$CF_3$ and —$CH_2CF_3$.

"Heteroalkyl" means an alkyl radical as defined herein with one, two or three substituents independently selected from cyano, —$OR^a$, —$NR^bR^c$, and —$S(O)_nR^d$ (where n is an integer from 0 to 2), with the understanding that the point of attachment of the heteroalkyl radical is through a carbon atom of the heteroalkyl radical. $R^a$ is hydrogen, alkyl, cycloalkyl, cycloalkyl-alkyl, aryl, arylalkyl, alkoxycarbonyl, aryloxycarbonyl, carboxamido, or mono- or dialkylcarbamoyl. $R^b$ is hydrogen, alkyl, cycloalkyl, cycloalkyl-alkyl, aryl or arylalkyl. $R^c$ is hydrogen, alkyl, cycloalkyl, cycloalkyl-alkyl, aryl, arylalkyl, alkoxycarbonyl, aryloxycarbonyl, carboxamido, mono- or dialkylcarbamoyl or alkylsulfonyl. $R^d$ is hydrogen (provided that n is 0), alkyl, cycloalkyl, cycloalkyl-alkyl, aryl, arylalkyl, amino, monoalkylamino, dialkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^a$, $R^b$, $R^c$, and $R^d$ can be further substituted by $NH_2$, fluorine, alkylamino, dialkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^a$, —$NR^bR^c$, or —$S(O)_nR^d$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl), —$(CR'R'')_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —$CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkyl-alkyl, heteroalkyl, phenyl or phenylalkyl). More specifically the term heteroaryl includes, but is not limited to, pyridyl, furanyl, thienyl, thiazolyl, isothiazolyl, triazolyl, tetrazolyl, imidazolyl, oxazolyl, isoxazolyl, pyrrolyl, pyrazolyl, pyrazinyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolyl, isoquinolyl, benzimidazolyl, benzisoxazolyl, benzothienyl, and the derivatives thereof.

"Heteroarylalkyl" means a radical —$R^aR^b$ where $R^a$ is an alkylene group and $R^b$ is a heteroaryl group as defined herein, e.g., pyridin-3-ylmethyl, 3-(benzofuran-2-yl)propyl, and the like.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, oxo, hydroxy, alkoxy, amino, monoalkylamino, dialkylamino, haloalkyl, haloalkoxy, —COR (where R is hydrogen, alkyl, cycloalkyl, cycloalkyl-alkyl, phenyl or phenylalkyl), —$(CR'R'')_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —$(CR'R'')_n$—$CONR^aR^b$ (where n is an integer from 0 to 5, R' and R" are independently hydrogen or alkyl, $R^a$ and $R^b$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N- methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of ring atoms, whether carbon or heteroatoms in the cycloheteroalkyl or heterocyclyl group.

"Heterocyclylalkyl", "cycloheteroalkyl-alkyl" or "heterocycloalkyl-alkyl" means a radical —$R^aR^b$ where $R^a$ is an alkylene group and $R^b$ is a heterocyclyl group as defined herein, e.g., tetrahydropyran-2-ylmethyl, 4-methylpiperazin-1-ylethyl, 3-piperidinylmethyl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl.

Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents generally selected from the substituents provided for aryl groups above. More particularly, the substituents can be selected from alkyl, cycloalkyl, cycloalkyl-alkyl, alkenyl, alkynyl, arylalkyl, halo, nitro, cyano, cyanoalkyl, hydroxy, hydroxyalkyl, alkoxy, amino, acylamino, monoalkylamino, dialkylamino, haloalkyl (e.g., fluoroalkyl), haloalkoxy (e.g, fluoroalkoxy), heteroalkyl, heteroalkenyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), —(CR'R")$_n$—CON-R$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl) or —NR'R", —NR"C(O)R', —NR"CO$_2$R', —NR'C(O)NR"R'", —SO$_2$R', —SO$_2$NR"R", —(C$_1$-C$_4$)alkylene-SO$_2$R', —(C$_1$-C$_4$)alkylene-SO$_2$NR'R" and —OC(O)NR'R" (where R', R" and R'" are independently hydrogen, alkyl, cycloalkyl, aryl, arylalkyl, —C(O)-alkyl, —CO$_2$-alkyl, —C(O)-heterocycloalkyl, —C(O)-fluoroalkyl, and heteroaryl). Optionally, two groups R', R", R'", R$^a$ or R$^b$ attached to a common nitrogen atom can be combined with the nitrogen atom to form a 3-, 4-, 5-, 6-, or 7-membered ring having from 1-3 heteroatoms selected from N, O and S.

The terms "modulate", "modulation" and the like refer to the ability of a compound to increase or decrease the function and/or expression of IKK, where IKK function may include kinase activity and/or protein-binding. Modulation may occur in vitro or in vivo. Modulation, as described herein, includes the inhibition or activation of IKK function and/or the downregulation or upregulation of IKK expression, either directly or indirectly. A modulator preferably activates IKK function and/or upregulates IKK expression. More preferably, a modulator activates or inhibits IKK function and/or upregulates or downregulates IKK expression. Most preferably, a modulator inhibits IKK function and/or downregulates IKK expression. The ability of a compound to inhibit IKK function can be demonstrated in an enzymatic assay or a cell-based assay (e.g., inhibition of IL-1-stimulated NF-κB activation).

"Pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

"Treating" or "treatment of" a disease includes inhibiting the disease, e.g., arresting or reducing the development of the disease or its clinical symptoms, or relieving the disease, e.g., causing regression of the disease or its clinical symptoms.

"Preventing" or "prevention of" the disease includes, e.g. causing the clinical symptoms of the disease not to develop in a mammal that may be exposed to or predisposed to the disease but does not yet experience or display symptoms of the disease.

As used herein, the term "condition or disorder responsive to IKK modulation" refers to a condition or disorder that is at least partially responsive to or affected by IKK modulation (e.g., an IKK inhibitor results in some improvement in patient well-being in at least some subjects suffering from said condition or disorder).

As used herein, the term "IKK-mediated disease or condition" and related terms and phrases refer to a disease, disorder or condition characterized by inappropriate, e.g., less than or greater than normal, IKK activity. Inappropriate IKK functional activity might arise as the result of IKK expression in cells which normally do not express IKK, increased IKK expression (leading to, e.g., inflammatory and immunoregulatory disorders and diseases) or decreased IKK expression. An IKK-mediated disease or condition may be completely or partially mediated by inappropriate IKK functional activity. However, an IKK-mediated disease or condition is one in which modulation of IKK results in some effect on the underlying disease or condition (e.g., an IKK inhibitor results in some improvement in patient well-being in at least some patients).

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry*, 4th edition J. March, John Wiley and Sons, New York, 1992).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabled compounds are useful as therapeutic agents (e.g., chemotherapeutic agents), research reagents (e.g., IKKβ binding assay reagents) and diagnostic agents (e.g., in vivo imaging agents). All isotopic variations of the compounds of the invention, whether radioactive or not, are intended to be encompassed within the scope of the invention.

EMBODIMENTS OF THE INVENTION

A class of compounds that interact with IKK has been discovered. Depending on the biological environment (e.g., cell type, pathological condition of the host, etc.), these compounds can activate or block the actions of IKK. By activating or inhibiting IKK, the compounds will find use as therapeutic agents capable of modulating diseases or conditions responsive to IKK modulation and/or mediated by IKK. As noted above, examples of such diseases and disorders include rheumatoid arthritis, septic shock, inflammatory bowel disease, bone mass loss, cancer, dermal sensitization disorders, diabetes, obesity and neurological conditions such as ischemic stroke and closed-head injuries. Additionally, the compounds are useful for the treatment of complications of these diseases and disorders (e.g., diabetic neuropathy). While the compounds of the invention are believed to exert their effects through modulation of IKK, the mechanism of action by which the compound act is not a limiting embodiment of the invention. For example, compounds of the invention may interact with one or more IKK isotypes, e.g., IKKβ and/or IKKα. In still other embodiments, compounds of the invention may modulate IRAK and/or IRAK and or one or more IKK isotypes. Accordingly, these compounds have further utility in the treatment of diseases or conditions mediated by IRAK.

Compounds contemplated by the invention include, but are not limited to, the exemplary compounds provided herein.

Compounds

In one aspect, the present invention provides compounds useful in the treatment of inflammatory, metabolic, infectious or cell proliferative diseases or conditions, having the formula (I):

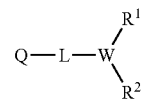

In formula I, W is a 5-6, 6-6 or 5-5 or fused bicyclic ring system, wherein one or both rings are aromatic, containing a nitrogen atom and from 0 to 3 additional heteroatoms selected from the group consisting of N, O and S, wherein (iii) the ring fusion atoms are independently CH or N, with the proviso that the ring fusion atoms are not both N; and (iv) the atoms to which L, $R^1$ and $R^2$ are attached are independently selected from the group consisting of =C—, —CH— and —N—.

$R^1$ is selected from the group consisting of —C(O)NR$^{1a}$R$^{1b}$, —C(O)R$^{1a}$, —CH(=NOH), —N(R$^{1b}$)C(O)R$^{1a}$, —SO$_2$NR$^{1a}$R$^{1b}$, —SO$_2$R$^{1a}$, —C(O)N(R$^{1a}$)OR$^{1b}$, —(C$_1$-C$_4$)alkylene-N(R$^{1b}$)C(O)R$^{1a}$, —(C$_1$-C$_4$)alkylene-C(O)NR$^{1a}$R$^{1b}$ and heteroaryl; wherein R$^{1a}$ and R$^{1b}$ are selected from hydrogen, (C$_1$-C$_6$)alkyl, (C$_2$-C$_4$)alkenyl, (C$_2$-C$_6$)heteroalkyl, hydroxy(C$_1$-C$_4$)alkyl, fluoro(C$_1$-C$_4$)alkyl, cyano(C$_1$-C$_4$)alkyl, cyclo(C$_3$-C$_8$)alkyl, mono- or di-hydroxycyclo(C$_3$-C$_8$)alkyl, heterocyclo(C$_3$-C$_8$)alkyl, heterocyclo(C$_3$-C$_8$)alkyl-C$_1$-C$_4$)alkyl; and optionally, R$^{1a}$ is attached to an adjacent ring member of W relative to the point of attachment of R$^1$ to form an additional 5- or 6-membered fused ring, or R$^{1a}$ and R$^{1b}$ are combined with their intervening atoms to form a 3-, 4-, 5- or 6-membered ring. In one embodiment, R$^1$ is selected from —C(O)NR$^2$R$^{1b}$, —SO$_2$NR$^{1a}$R$^{1b}$, —SO$_2$R$^{1a}$, —C(O)R$^{1a}$, imidazolyl, pyrazolyl, tetrazolyl, oxazolyl, thiazolyl, thienyl and pyridyl. In another embodiment, R$^1$ is selected from —C(O)NHR$^{1a}$, —O$_2$NHR$^{1a}$, —SO$_2$R$^{1a}$, —C(O)CH$_3$ and thiazolyl. In another embodiment, R$^1$ is selected from —C(O)NHR$^{1a}$, —SO$_2$NHR$^{1a}$ and —C(O)CH$_3$. In still another embodiment, R$^1$ is —(O)NH$_2$.

$R^2$ is selected from the group consisting of —NR$^{2a}$R$^{2b}$ and —OH; wherein R$^{2a}$ and R$^{2b}$ are selected from hydrogen, (C$_1$-C$_6$)alkyl, (C$_2$-C$_4$)alkenyl, (C$_2$-C$_6$)heteroalkyl, mono- or di-hydroxy(C$_1$-C$_4$)alkyl, fluoro(C$_1$-C$_4$)alkyl, cyano(C$_1$-C$_4$)alkyl, cyclo(C$_3$-C$_8$)alkyl, mono- or di-hydroxycyclo(C$_3$-C$_8$)alkyl, heterocyclo(C$_3$-C$_8$)alkyl, heterocyclo(C$_3$-C$_8$)alkyl-(C$_1$-C$_4$)alkyl, aryl, aryl(C$_1$-C$_4$)alkyl, heteroaryl, heteroaryl (C$_1$-C$_4$)alkyl, —C(O)—(C$_1$-C$_4$)alkyl, —C(O)—(C$_1$-C$_4$)alkoxy, —C(O)-heterocyclo(C$_3$-C$_8$)alkyl and C(O)-fluoro ($C_1$-$C_4$)alkyl; and optionally, $R^{2a}$ and $R^{2b}$ may be combined with the nitrogen atom to which each is attached to form a 5-, 6- or 7-membered ring containing from 1-3 heteroatoms selected from N, O and S. In one embodiment, $R^2$ is —$NHR^{2b}$. In another embodiment, $R^2$ is —$NH_2$. In still other embodiments, $R^2$ is —$NR^{2a}R^{2b}$ wherein $R^{2a}$ and $R^{2b}$, taken together with the nitrogen to which each is attached, form a 5- or 6-membered ring having from 1-3 heteroatom ring members, and which is further substituted with from one to three substituents selected from OH, $CONH_2$ and $NH_2$.

L is a divalent linkage selected from the group consisting of a single bond, ($C_1$-$C_4$)alkylene, —C(O)—, —C(O)N($R^3$)—, —$SO_2$N($R^3$)—, —C($R^3$)=C($R^4$)—, —O—, —S— and —N($R^3$)—; wherein $R^3$ and $R^4$ are independently selected from the group consisting of hydrogen, ($C_1$-$C_6$)alkyl, cyclo($C_3$-$C_8$)alkyl, aryl, aryl($C_1$-$C_4$)alkyl, hetero($C_1$-$C_6$)alkyl, heterocyclo($C_5$-$C_8$)alkyl, heteroaryl, heteroaryl($C_1$-$C_4$)alkyl and arylhetero($C_1$-$C_4$)alkyl. In one group of embodiments, L is selected from a single bond, ($C_1$-$C_4$)alkyl and —C(O)—.

Q is selected from the group consisting of ($C_2$-$C_6$)alkenyl, ($C_2$-$C_6$)alkynyl, ($C_1$-$C_6$)alkoxy, halogen, aryl, aryl($C_1$-$C_4$)alkyl, heteroaryl, cyclo($C_3$-$C_8$)alkyl, cyclo($C_5$-$C_8$)alkenyl and heterocyclo($C_3$-$C_8$)alkyl, wherein each of the moieties is optionally further substituted as indicated below. In one embodiment, Q is selected from the group consisting of phenyl, naphthyl, pyridyl, furyl, thienyl, thiazolyl, isothiazolyl, triazolyl, imidazolyl, oxazolyl, isoxazolyl, pyrrolyl, pyrrolidinyl, pyrazolyl, pyrazinyl, pyridazinyl, pyrimidyl, benzofuryl, tetrahydrobenzofuryl, isobenzofuryl, benzthiazolyl, benzoisothiazolyl, benzotriazolyl, indolyl, isoindolyl, benzoxazolyl, quinolyl, tetrahydroquinolyl, isoquinolyl, benzimidazolyl, benzisoxazolyl, benzothienyl, cyclopentyl and cyclohexyl, each of which is substituted or unsubstituted. In another embodiment, Q is un(substituted) phenyl, un(substituted) thienyl, or un(substituted)($C_2$-$C_6$)alkynyl wherein from 1 to 3 substituents may be present and are selected from halogen, cyano, nitro, cyano($C_2$-$C_6$)alkenyl, nitro($C_2$-$C_6$)alkenyl, —R', —OR', —NR'R", —C(O)', —$CO_2$R', —C(O)NR'R", —NR"C(O)R', —NR"$CO_2$R', —NR'C(O)NR"R'", —S(O)R', —$SO_2$R', —$SO_2$NR'R", —NR"$SO_2$R', —OC(O)NR'R", —X—C(O)R', —X—$CO_2$R', —X—C(O)NR'R", —X—NR"C(O)R', —X—NR"$CO_2$R', —X—NR'C(O)NR"R'", —X—S(O)R', —X—$SO_2$R', —X—$SO_2$NR'R", —X—NR"$SO_2$R' and —X—OC(O)NR'R", and optionally R' or R" is attached to an adjacent ring atom on the phenyl group or thienyl group to form a 5- or 6-membered fused ring.

X is ($C_1$-$C_6$)alkylene. Preferably a methylene, ethylene or propylene.

R', R" and R'" are independently selected from the group consisting of hydrogen, ($C_1$-$C_6$)alkyl, ($C_2$-$C_4$)alkenyl, ($C_1$-$C_6$)heteroalkyl, hydroxy($C_1$-$C_4$)alkyl, fluoro($C_1$-$C_4$)alkyl, cyano($C_1$-$C_4$)alkyl, cyano($C_1$-$C_4$)haloalkyl, cyclo($C_3$-$C_8$)alkyl, mono- or di-hydroxycyclo($C_3$-$C_8$)alkyl, heterocyclo($C_3$-$C_8$)alkyl, heterocyclo($C_3$-$C_8$)alkyl-($C_1$-$C_4$)alkyl, aryl, aryl($C_1$-$C_4$)alkyl, heteroaryl, heteroaryl($C_1$-$C_4$)alkyl, —C(O)—($C_1$-$C_4$)alkyl, —C(O)—($C_1$-$C_4$)alkoxy, —C(O)-heterocyclo($C_3$-$C_8$)alkyl and —C(O)-fluoro($C_1$-$C_4$)alkyl. Optionally, any two of R', R" and R'" can be combined with their intervening atom(s) to form a 5-, 6- or 7-membered ring containing from 1-3 heteroatoms selected from N, O and S.

Within the above compounds of formula I, the compound is other than

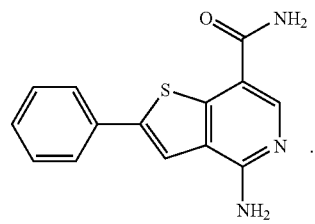

Within these embodiments are several groups of preferred embodiments, described below. In each of these preferred embodiments, the compound is other than

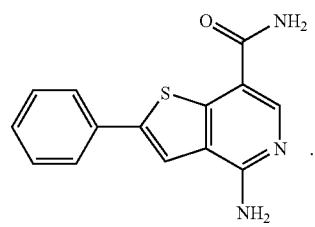

One group of preferred embodiments is represented by the formula:

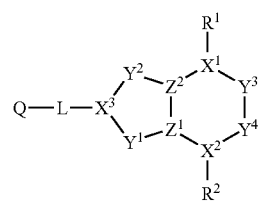

Ia.1

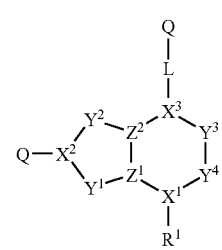

Ia.2

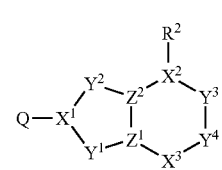

Ia.3

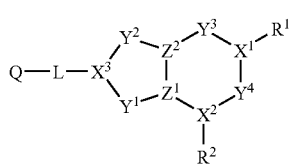

Ia.4

-continued
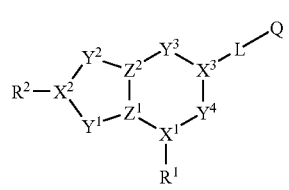
Ia.5
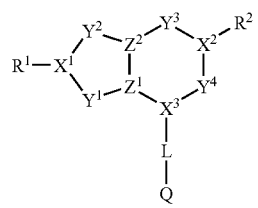
Ia.6
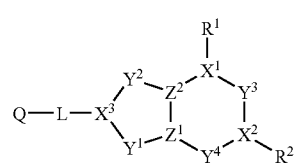
Ia.7
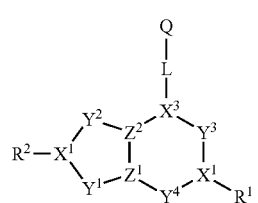
Ia.8
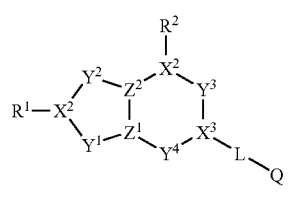
Ia.9
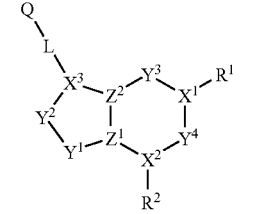
Ia.10
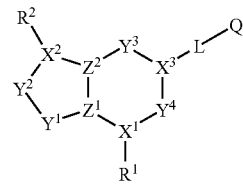
Ia.11
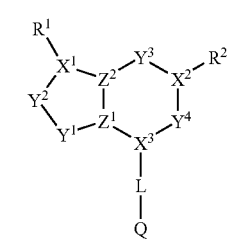
Ia.12
-continued
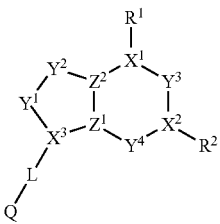
Ia.13
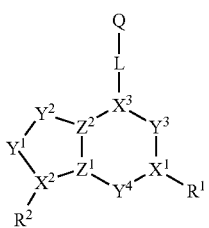
Ia.14
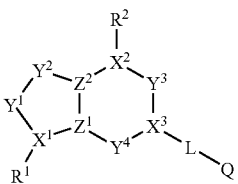
Ia.15
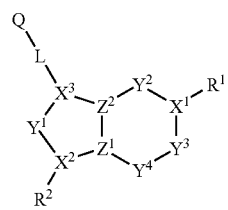
Ia.16
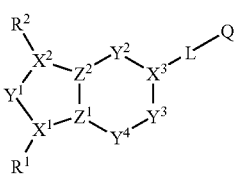
Ia.17
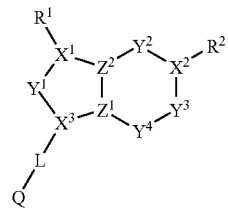
Ia.18
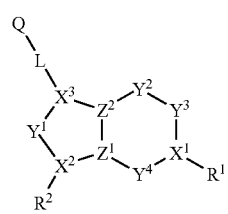
Ia.19

-continued

Ia.20
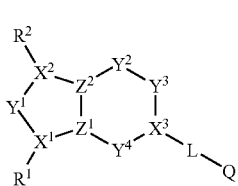

Ia.21
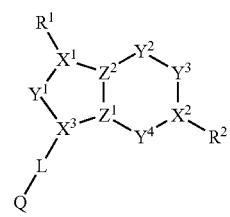

wherein $X^1$, $X^2$ and $X^3$ are independently selected from the group consisting of =C—, —CH— and —N—;

$Y^1$, $Y^2$, $Y^3$ and $Y^4$ are independently selected from the group consisting of =C($R^{5a}$)—, —C($R^5$)($R^6$)—, —C(O)—, =N—, —N($R^5$)—, —O— and —S(O)$_m$—;

$Z^1$ and $Z^2$ are independently CH or N;

Each $R^5$ and $R^6$ is independently selected from the group consisting of hydrogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero (C$_1$-C$_4$)alkyl;

Each $R^{5a}$ is independently selected from the group consisting of hydrogen, halogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero (C$_1$-C$_4$)alkyl;

the subscript m is an integer of from 0 to 2; and $R^1$, $R^2$, L and Q have the meanings and preferred groupings provided above.

Another group of preferred embodiments is represented by the formula:

Ib.1
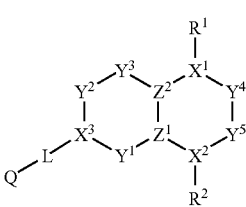

Ib.2
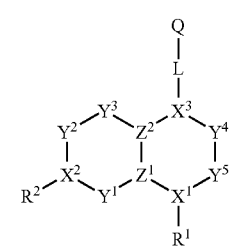

-continued

Ib.3
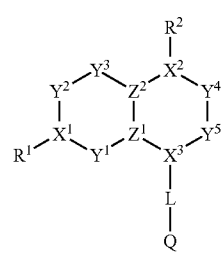

Ib.4
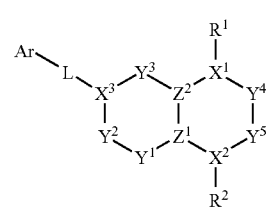

Ib.5
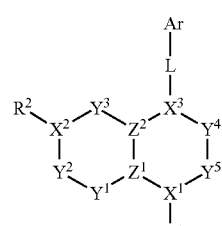

Ib.6
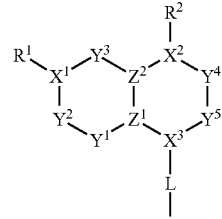

Ib.7
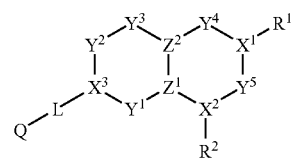

Ib.8
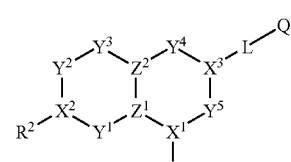

Ib.9
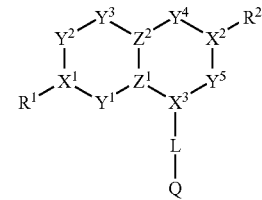

-continued

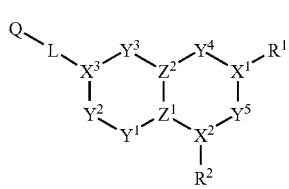
Ib.10

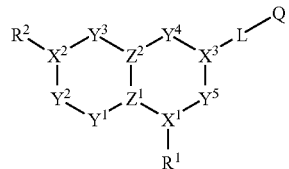
Ib.11

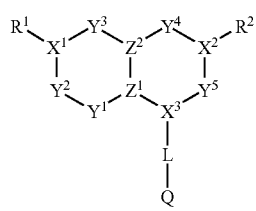
Ib.12

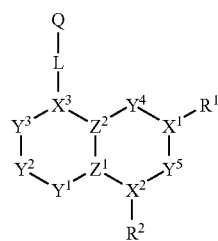
Ib.13

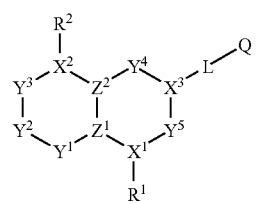
Ib.14

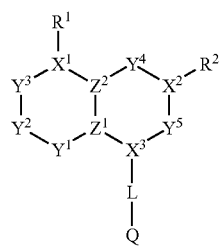
Ib.15

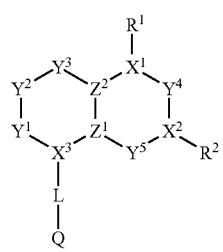
Ib.16

-continued

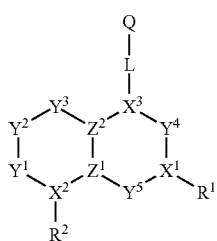
Ib.17

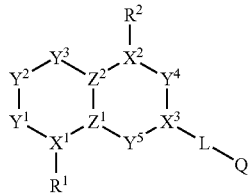
Ib.18 wherein $Y^5$ is independently selected from the group consisting of =C($R^{5a}$)—, —C($R^5$)($R^6$)—, —C(O)—, =N—, —N($R^5$)—, —O— and —S(O)$_m$— and $R^1$, $R^2$, L, Q, $X^1$, $X^2$, $X^3$, $Y^1$, $Y^2$, $Y^3$, $Y^4$, $Z^1$, $Z^2$, $R^5$, $R^{5a}$, $R^6$ and the subscript m have the meanings and preferred groupings provided above.

Another group of preferred embodiments is represented by the formula:

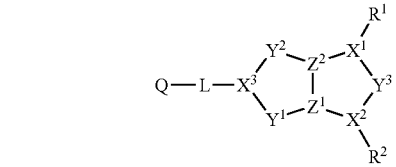
Ic.1

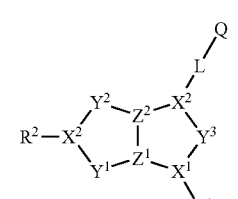
Ic.2

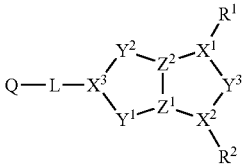
Ic.3 wherein $R^1$, $R^2$, L, Q, $X^1$, $X^2$, $X^3$, $Y^1$, $Y^2$, $Y^3$ $Z^1$, $Z^2$, $R^5$, $R^{5a}$, $R^6$ and the subscript m have the meanings and preferred groupings provided above.

Preferred are those embodiments that combine preferred groups. Accordingly, in one group of preferred embodiments, $R^1$ is selected from —(O)NR$^{1a}$R$^{1b}$, —SO$_2$NR$^{1a}$R$^{1b}$, —SO$_2$R$^{1a}$, —C(O)R$^{1a}$, imidazolyl, pyrazolyl, tetrazolyl, oxazolyl, thiazolyl, thienyl and pyridyl, and $R^2$ is —NHR$^{2b}$.

In another group of preferred embodiments, $R^1$ is selected from —C(O)NHR$^{1a}$, —SO$_2$NHR$^{1a}$, —SO$_2$R$^{1a}$, —C(O)CH$_3$ and thiazolyl, and $R^2$ is —NHR$^{2b}$. In yet another group of preferred embodiments, $R^1$ is selected from —C(O)NHR$^{1a}$, —SO$_2$NHR$^{1a}$ and —C(O)CH$_3$, and $R^2$ is —NHR$^{2b}$. In still another group of preferred embodiments, $R^1$ is —C(O)NHR$^{1a}$ and $R^2$ is —NHR$^{2b}$. In still further preferred embodiments, $R^1$ is —C(O)NH$_2$ and $R^2$ is —NH$_2$.

One group of preferred embodiments is represented by the formula (III):

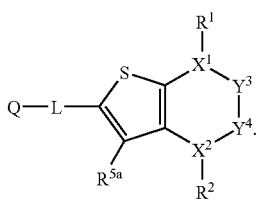

In formula III, $R^1$, $R^2$, $R^{5a}$, L, Q, $X^1$, $X^2$, $Y^3$ and $Y^4$ have the meanings and preferred groupings provided above. Preferably, $R^{5a}$ is hydrogen or halogen, and is independent of any remaining $R^{5a}$ substituents that are present as part of $Y^3$ or $Y^4$.

Another group of preferred embodiments is represented by the formula (IV):

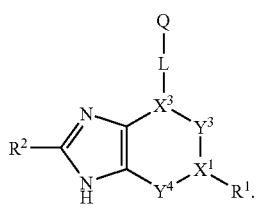

$R^1$, $R^2$, L, Q, $X^1$, $X^3$, $Y^3$ and $Y^4$ have the meanings and preferred groupings provided above.

Another group of preferred embodiments is represented by the formula (V):

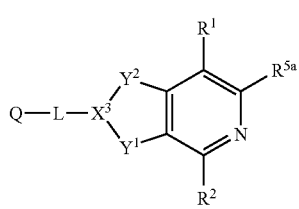

In formula V, $R^1$, $R^2$, $R^{5a}$, L, Q, $X^3$, $Y^1$ and $Y^2$ have the meanings and preferred groupings provided above.

Still another group of preferred embodiments is represented by the formula (VI):

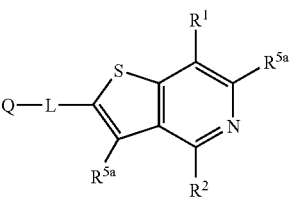

In formula VI, each $R^2$ is independently selected from hydrogen, halogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl, with preferred members being those that have been described above. $R^1$, $R^2$, L and Q have the meanings and preferred groupings provided above. Preferably, $R^{5a}$ attached to the six-membered ring is hydrogen. More preferably, each $R^{5a}$ is hydrogen.

In related, and preferred embodiments of formula VI, L is a bond; Q is phenyl, thienyl or (C$_2$-C$_6$)alkynyl, wherein any phenyl, thienyl or alkynyl portion is optionally substituted as indicated above in the general discussion of Q; and the $R^{5a}$ attached to the five-membered ring is (C$_1$-C$_6$)alkyl.

Still other preferred embodiments are provided are formulae A-G, below, wherein the phenyl and thienyl rings can be substituted or unsubstituted. Additionally, in formula G, the symbol R represents a substituted or unsubstituted (C$_1$-C$_4$) alkyl. The remaining substituents have the meanings provided above with respect to formula I, as well as preferred embodiments as recited for formula I as well as formulae III, V and VI.

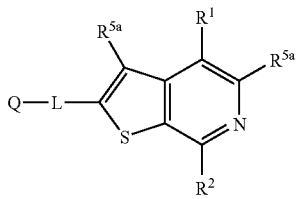

A

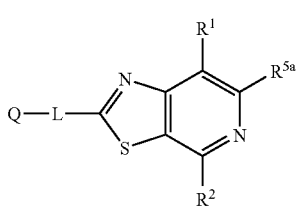

B

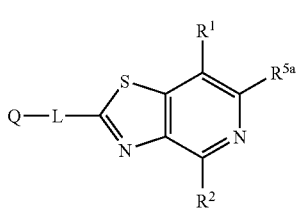

C

-continued

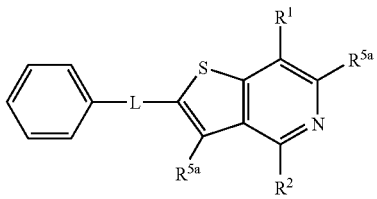
D

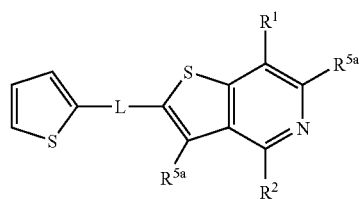
E

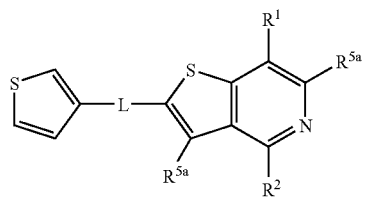
F

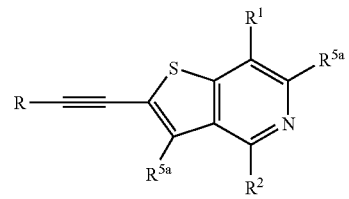
G

Figure 2:
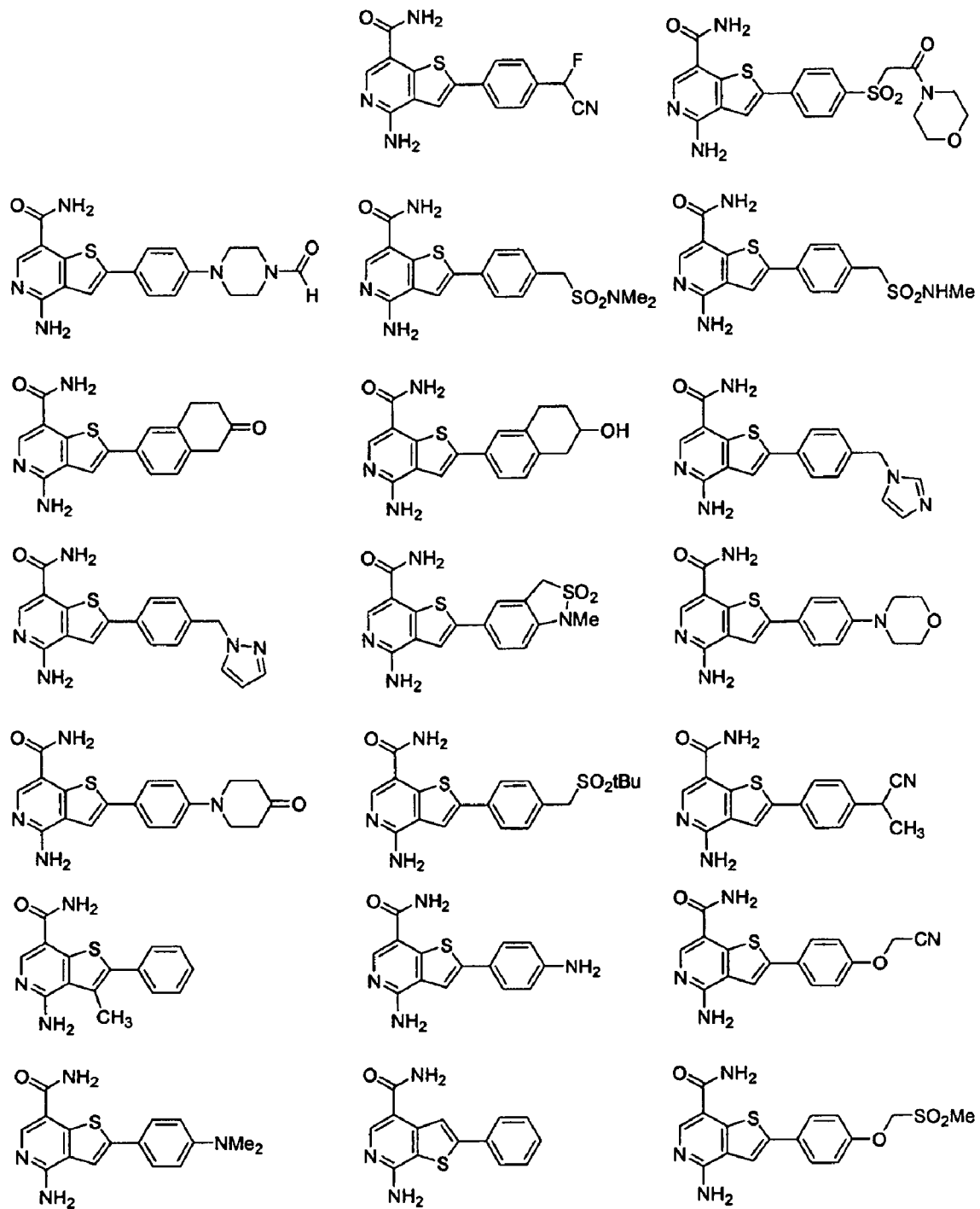
Figure 3:
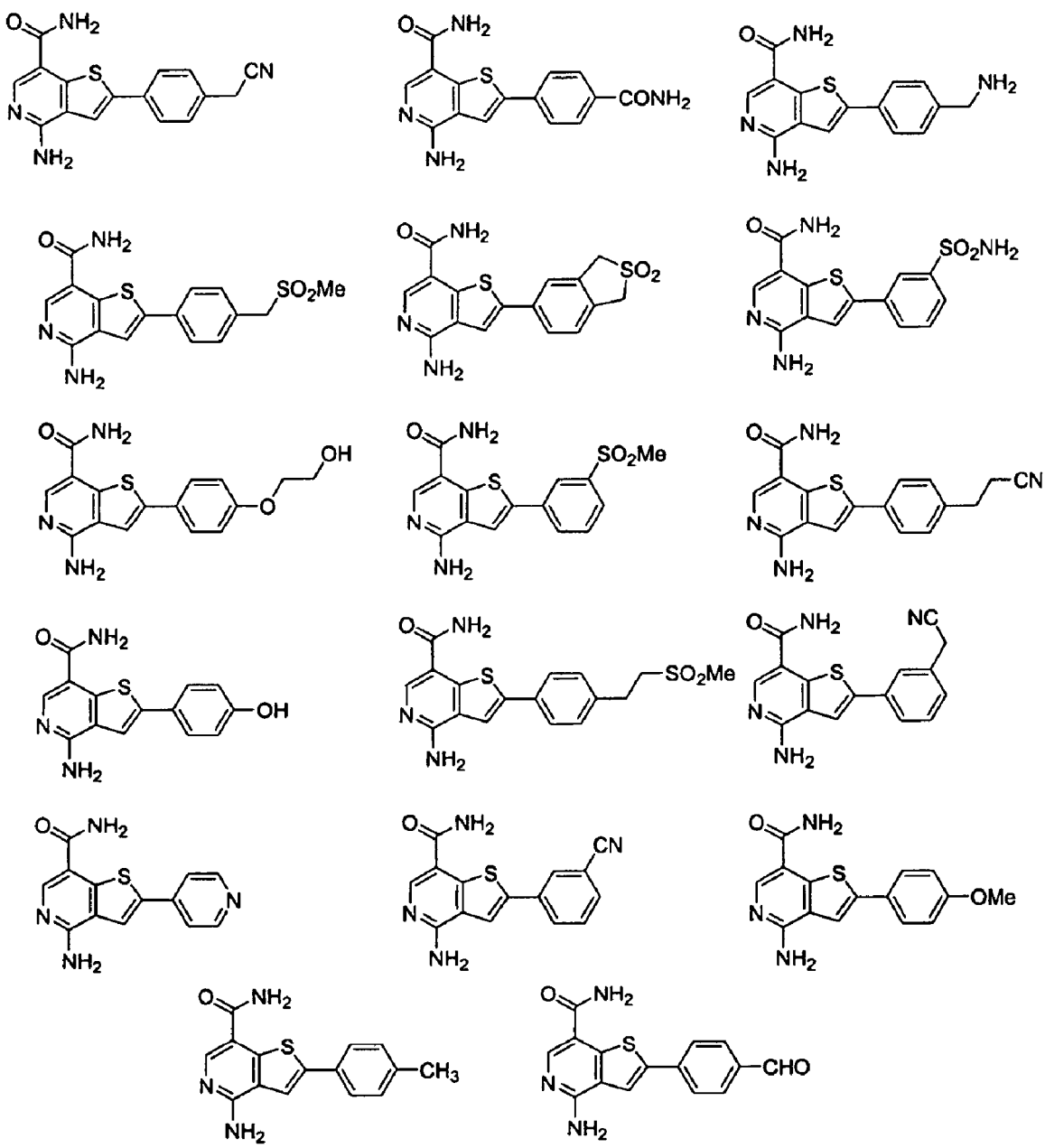
Figure 4:
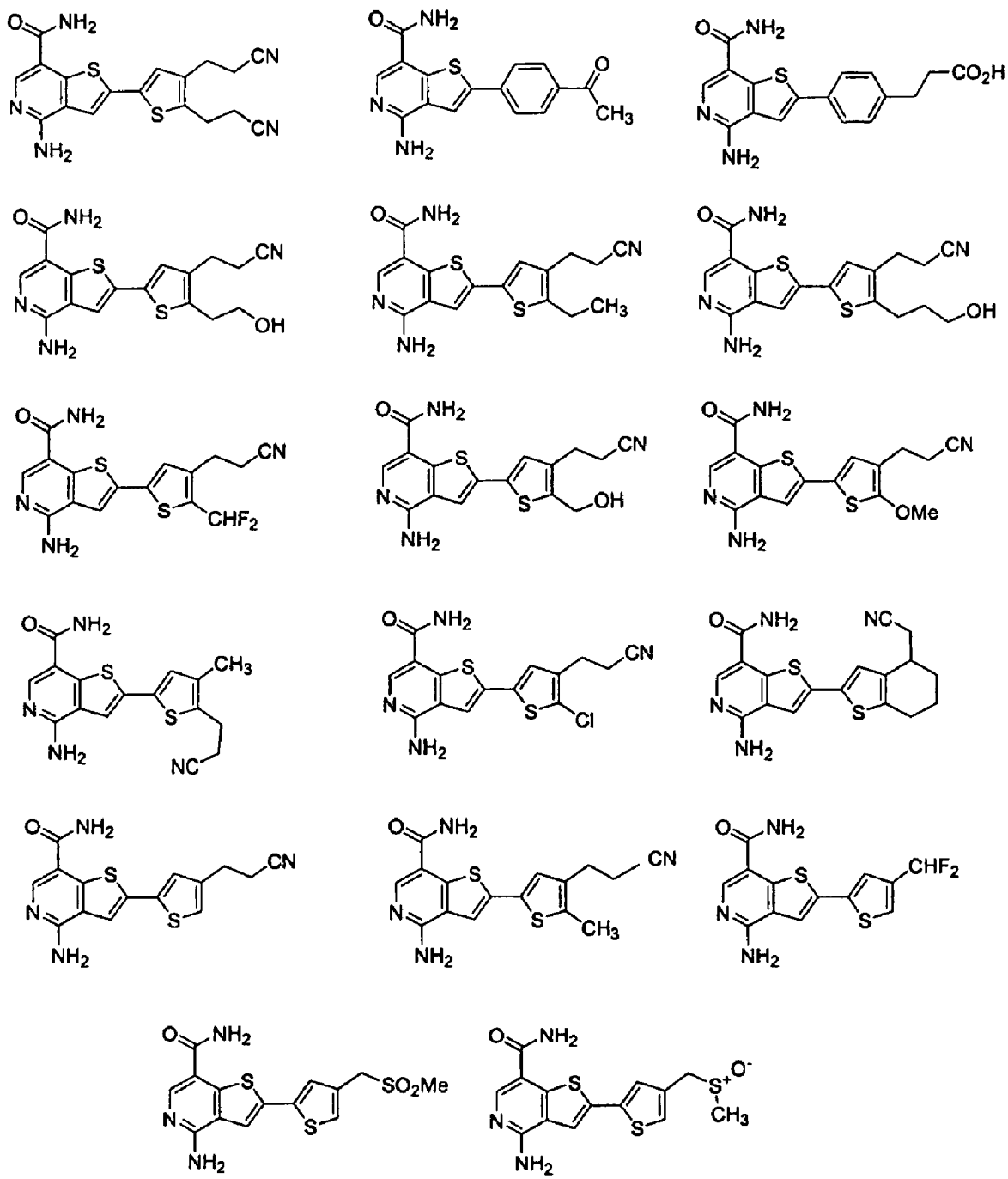
Figure 5:
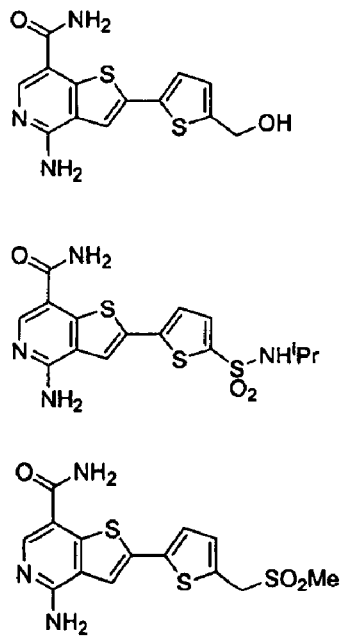
Figure 5:
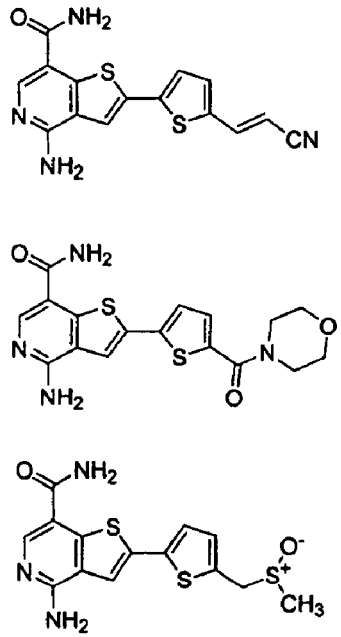
Figure 5:
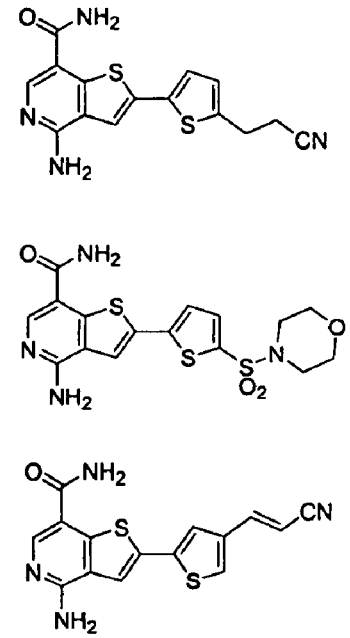
Figure 5:
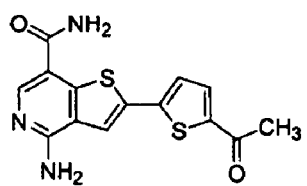
Figure 5:
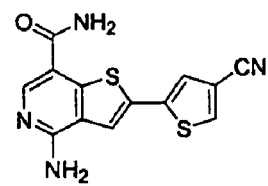
Figure 5:
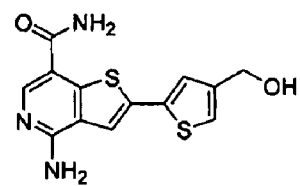
Figure 5:
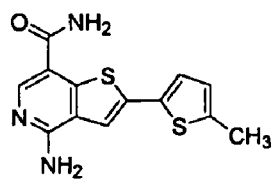
Figure 5:
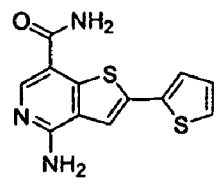
Figure 5:
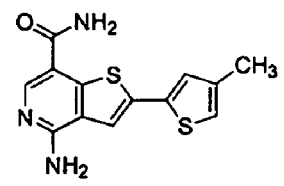
Figure 5:
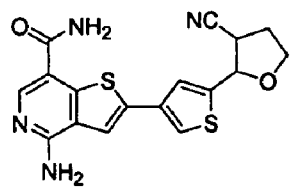
Figure 6:
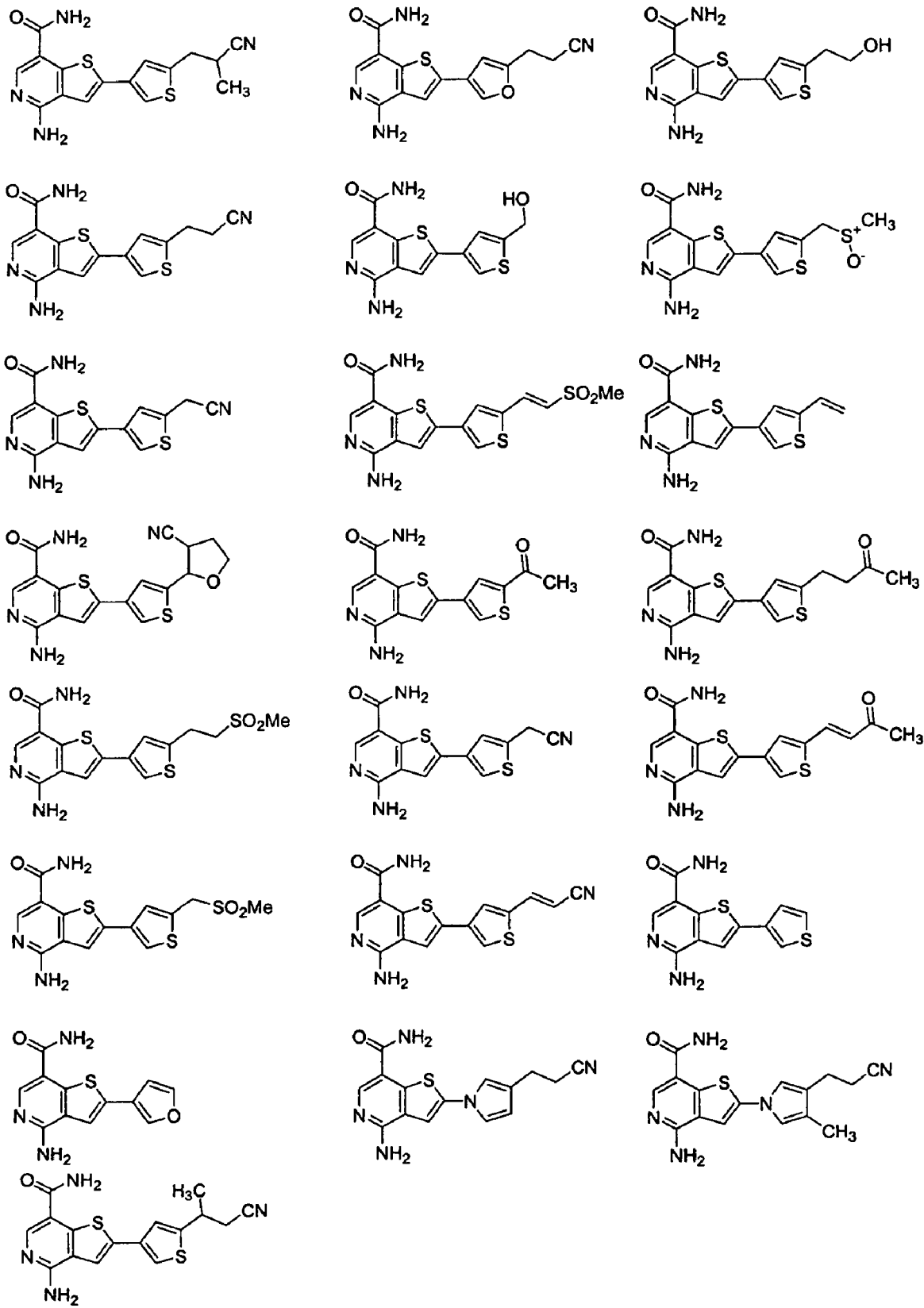
Figure 7:
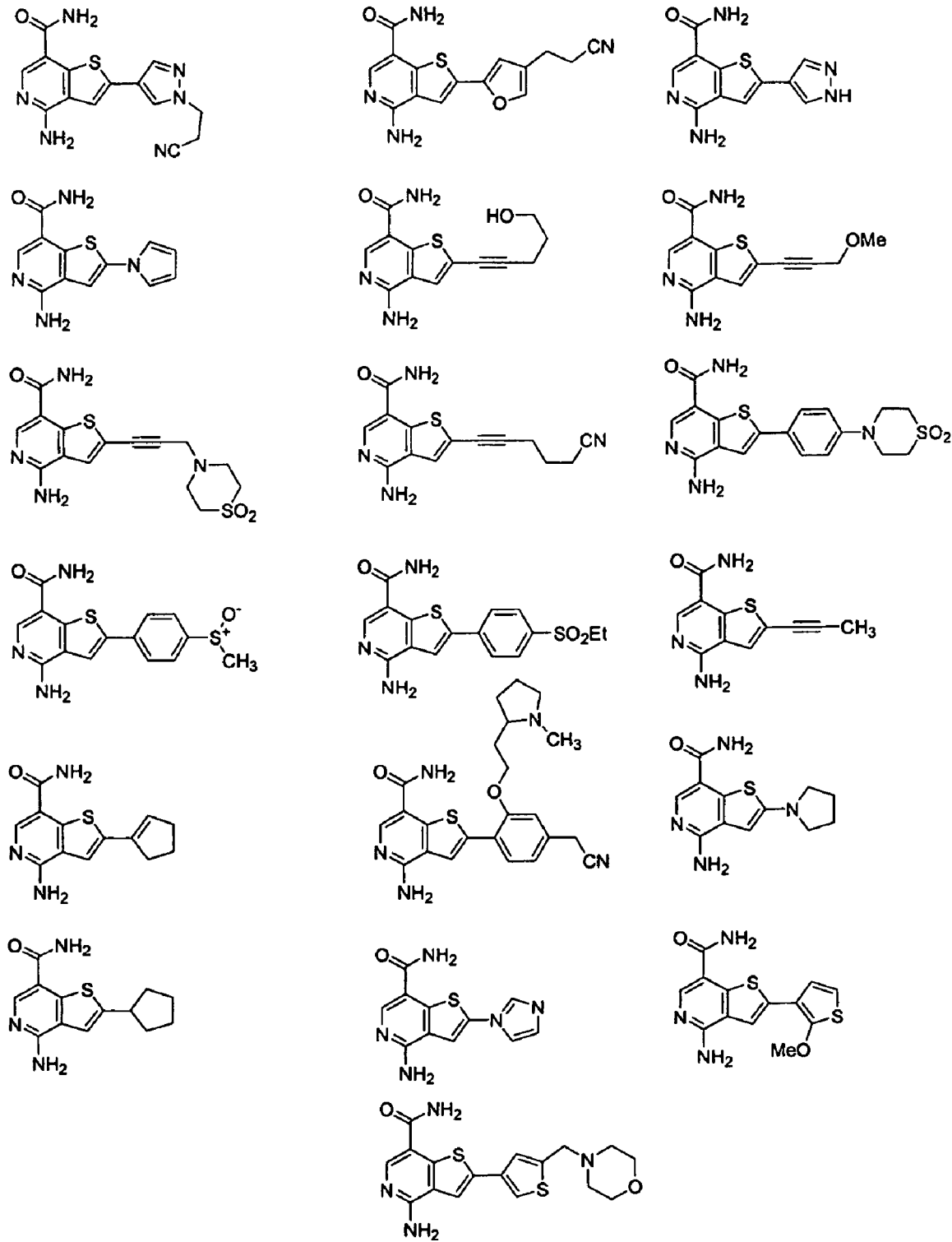

Exemplary compounds of the invention are provided in FIGS. 1-7.

The present invention also provides compounds useful in the treatment of inflammatory, metabolic, infectious or cell proliferative diseases or conditions, having the formula:

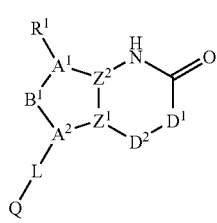
VIIa.1

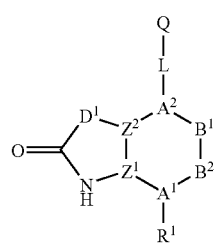
VIIa.2

-continued

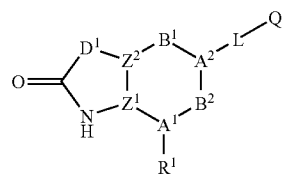
VIIa.3

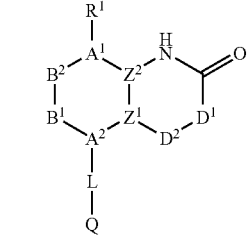
VIIb.1

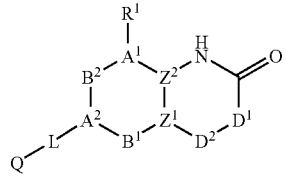
VIIb.2 wherein $R^1$ is selected from the group consisting of —C(O)NR$^{1a}$R$^{1b}$, —C(O)R$^{1a}$, —CH(=NOH), —N(R$^{1b}$)C(O)R$^{1a}$, —SO$_2$NR$^{1a}$R$^{1b}$, —SO$_2$R$^{1a}$, —C(O)N(R$^{1a}$)OR$^{1b}$, —(C$_1$-C$_4$)alkylene-N(R$^{1b}$)C(O)R$^{1a}$, —(C$_1$-C$_4$)alkylene-C(O)NR$^{1a}$R$^{1b}$ and heteroaryl; wherein R$^{1a}$ and R$^{1b}$ are selected from hydrogen, (C$_1$-C$_6$)alkyl, (C$_2$-C$_4$)alkenyl, (C$_2$-C$_6$)heteroalkyl, hydroxy(C$_1$-C$_4$)alkyl, fluoro(C$_1$-C$_4$)alkyl, cyano(C$_1$-C$_4$)alkyl, cyclo(C$_3$-C$_8$)alkyl, mono- or di-hydroxycyclo(C$_3$-C$_8$)alkyl, heterocyclo(C$_3$-C$_8$)alkyl, heterocyclo(C$_3$-C$_8$)alkyl-(C$_1$-C$_4$)alkyl; and optionally, R$^{1a}$ is attached to an adjacent ring member of W relative to the point of attachment of R$^1$ to form an additional 5- or 6-membered fused ring. In one embodiment, R$^1$ is selected from —C(O)NR$^{1a}$R$^{1b}$, —SO$_2$NR$^{1a}$R$^{1b}$, —SO$_2$R$^{1a}$, —C(O)R$^{1a}$, imidazolyl, pyrazolyl, tetrazolyl, oxazolyl, thiazolyl, thienyl and pyridyl. In another embodiment, R$^1$ is selected from —C(O)NHR$^{1a}$, —SO$_2$NHR$^{1a}$, —SO$_2$R$^{1a}$, —(O)CH$_3$ and thiazolyl. In another embodiment, R$^1$ is selected from —(O)NHR$^{1a}$, —SO$_2$NHR$^{1a}$ and —C(O)CH$_3$. In still another embodiment, R$^1$ is —(O)NH$_2$ L is a divalent linkage selected from the group consisting of a single bond, (C$_1$-C$_4$)alkylene, —C(O)—, —C(O)N(R$^3$)—, —SO$_2$N(R$^3$)—, —C(R$^3$)=C(R$^4$)—, —O—, —S— and —N(R$^3$)—; wherein R$^3$ and R$^4$ are independently selected from the group consisting of hydrogen, (C$_1$-C$_6$)alkyl, cyclo(C$_3$-C$_8$)alkyl, aryl, aryl(C$_1$-C$_4$)alkyl, hetero(C$_1$-C$_6$)alkyl, heterocyclo(C$_5$-C$_8$)alkyl, heteroaryl, heteroaryl(C$_1$-C$_4$)alkyl and arylhetero(C$_1$-C$_4$)alkyl. In one group of embodiments, L is selected from a single bond, (C$_1$-C$_4$)alkyl and —C(O)—.

Q is selected from the group consisting of (C$_2$-C$_6$)alkenyl, (C$_2$-C$_6$)alkynyl, (C$_1$-C$_6$)alkoxy, halogen, aryl, aryl(C$_1$-C$_4$)alkyl, heteroaryl, cyclo(C$_3$-C$_8$)alkyl, cyclo(C$_5$-C$_8$)alkenyl and heterocyclo(C$_3$-C$_8$)alkyl, wherein each of the moieties is optionally further substituted as indicated below. In one embodiment, Q is selected from the group consisting of phenyl, naphthyl, pyridyl, furyl, thienyl, thiazolyl, isothiazolyl, triazolyl, imidazolyl, oxazolyl, isoxazolyl, pyrrolyl, pyrrolidinyl, pyrazolyl, pyrazinyl, pyridazinyl, pyrimidyl, benzofuryl, tetrahydrobenzofuryl, isobenzofuryl, benzthiazolyl, benzoisothiazolyl, benzotriazolyl, indolyl, isoindolyl, benzoxazolyl, quinolyl, tetrahydroquinolyl, isoquinolyl, benzimidazolyl, benzisoxazolyl, benzothienyl, cyclopentyl and cyclohexyl, each of which is substituted or unsubstituted. In another embodiment, Q is un(substituted) phenyl, un(substituted) thienyl, or un(substituted)($C_2$-$C_6$)alkynyl wherein from 1 to 3 substituents may be present and are selected from halogen, cyano, nitro, cyano($C_2$-$C_6$)alkenyl, nitro($C_2$-$C_6$)alkenyl, —R', —OR', —NR'R", —C(O)R', —$CO_2$R', —C(O)NR'R", —NR"C(O)R', —NR"$CO_2$R', —NR'C(O)NR"R'", —S(O)R', —$SO_2$R', —$SO_2$NR'R", —NR"$SO_2$R', —OC(O)NR'R", —X—C(O)R', —X—$CO_2$R', —X—C(O)NR'R", —X—NR"C(O)R', —X—NR"$CO_2$R', —X—NR'C(O)NR"R'", —X—S(O)R', —X—$SO_2$R', —X—$SO_2$NR'R", —X—NR"$SO_2$R' and —X—OC(O)NR'R", and optionally R' or R" is attached to an adjacent ring atom on the phenyl group or thienyl group to form a 5- or 6-membered fused ring.

X is ($C_1$-$C_6$)alkylene. Preferably a methylene, ethylene or propylene.

R', R" and R'" are independently selected from the group consisting of hydrogen, ($C_1$-$C_6$)alkyl, ($C_2$-$C_4$)alkenyl, ($C_1$-$C_6$)heteroalkyl, hydroxy($C_1$-$C_4$)alkyl, fluoro($C_1$-$C_4$)alkyl, cyano($C_1$-$C_4$)alkyl, cyano($C_1$-$C_4$)haloalkyl, cyclo($C_3$-$C_8$)alkyl, mono- or di-hydroxycyclo($C_3$-$C_8$)alkyl, heterocyclo($C_3$-$C_8$)alkyl, heterocyclo($C_3$-$C_8$)alkyl-($C_1$-$C_4$)alkyl, aryl, aryl($C_1$-$C_4$)alkyl, heteroaryl, heteroaryl($C_1$-$C_4$)alkyl, —C(O)—($C_1$-$C_4$)alkyl, —C(O)—($C_1$-$C_4$)alkoxy, —C(O)-heterocyclo($C_3$-$C_8$)alkyl and —C(O)-fluoro($C_1$-$C_4$)alkyl. Optionally, any two of R', R" and R'" can be combined with their intervening atom(s) to form a 5-, 6- or 7-membered ring containing from 1-3 heteroatoms selected from N, O and S.

$A^1$ and $A^2$ are independently selected from the group consisting of =C—, —CH— and —N—;

$B^1$ and $B^2$ are independently selected from the group consisting of =C($R^{5a}$)—, —C($R^5$)($R^6$)—, —C(O)—, =N—, —N($R^5$)—, — and —S(O)$_m$—;

$D^1$ is selected from the group consisting of —C($R^7$)($R^8$)—, —N($R^7$)— and —O—;

$D^2$ is selected from the group consisting of —C($R^9$)($R^{10}$)—, —C(O)—, —N($R^9$)—, —O— and —S(O)$_n$—;

optionally, $D^1$-$D^2$ may be —C($R^{11}$)=C(O$R^{12}$)— or —C($R^{11}$)=N—, $Z^1$ and $Z^2$ are independently CH or N;

$R^3$, $R^4$, $R^5$, $R^6$, $R^7$, $R^8$, $R^9$ and $R^{10}$ are independently selected from the group consisting of hydrogen, ($C_1$-$C_6$)alkyl, cyclo($C_3$-$C_8$)alkyl, aryl, aryl($C_1$-$C_4$)alkyl, hetero($C_1$-$C_6$)alkyl, heterocyclo($C_5$-$C_8$)alkyl, heteroaryl, heteroaryl($C_1$-$C_4$)alkyl and arylhetero($C_1$-$C_4$)alkyl;

$R^{5a}$ is independently selected from the group consisting of hydrogen, halogen, ($C_1$-$C_6$)alkyl, cyclo($C_3$-$C_8$)alkyl, aryl, aryl($C_1$-$C_4$)alkyl, hetero($C_1$-$C_6$)alkyl, heterocyclo($C_5$-$C_8$)alkyl, heteroaryl, heteroaryl($C_1$-$C_4$)alkyl and arylhetero($C_1$-$C_4$)alkyl;

$R^{11}$ and $R^{12}$ are independently selected from the group consisting of hydrogen and ($C_1$-$C_6$)alkyl, aryl and aryl($C_1$-$C_4$)alkyl; and the subscripts m and n are independently an integer of from 0 to 2; with the proviso that $D^1$ and $D^2$ are not both —N($R^9$)— or —O—.

One group of preferred embodiments is represented by the formula:

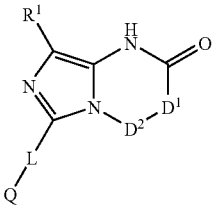

VIII

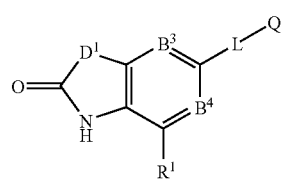

IX

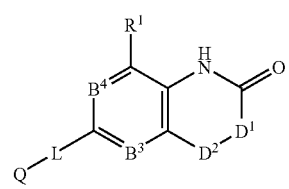

X wherein $B^3$ and $B^4$ are independently C($R^{5a}$) or N. $R^1$, L, Q, $D^1$ and $D^2$ have the meanings and preferred groupings provided above.

In sum, the invention encompasses novel compounds, novel pharmaceutical compositions and/or novel methods of use. While some compounds disclosed herein may be available from commercial sources, the pharmaceutical compositions or methods of using these compounds are novel. Unless otherwise indicated, it is to be understood that the invention includes those compounds that are novel, as well as pharmaceutical compositions, various methods (e.g., methods of treating or preventing certain IKK-mediated diseases or conditions), and the like which include both the novel compounds of the invention and compounds that are commercially available.

Compounds contemplated by the invention include, but are not limited to, the exemplary compounds provided herein.

Preparation of the Compounds

Exemplary methods for the preparation of the compounds of the invention are provided below and in the Examples. One of skill in the art will understand that additional methods are also useful. In other words, the compounds of the invention can be made using conventional organic synthetic methods, starting materials, reagents and reactions known in the art.

Scheme 1a
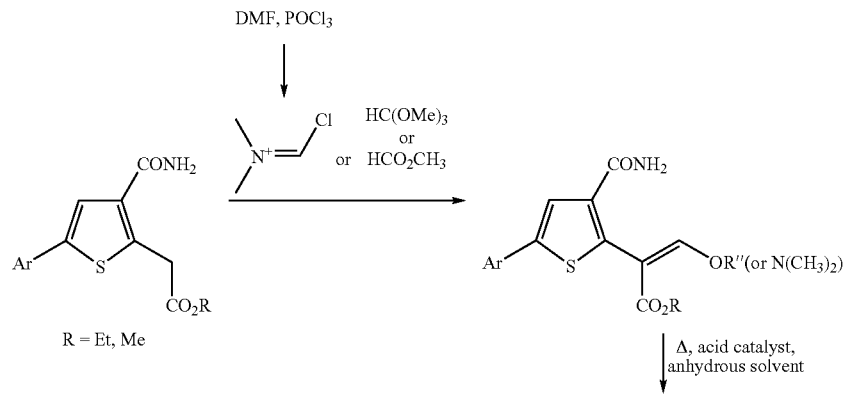
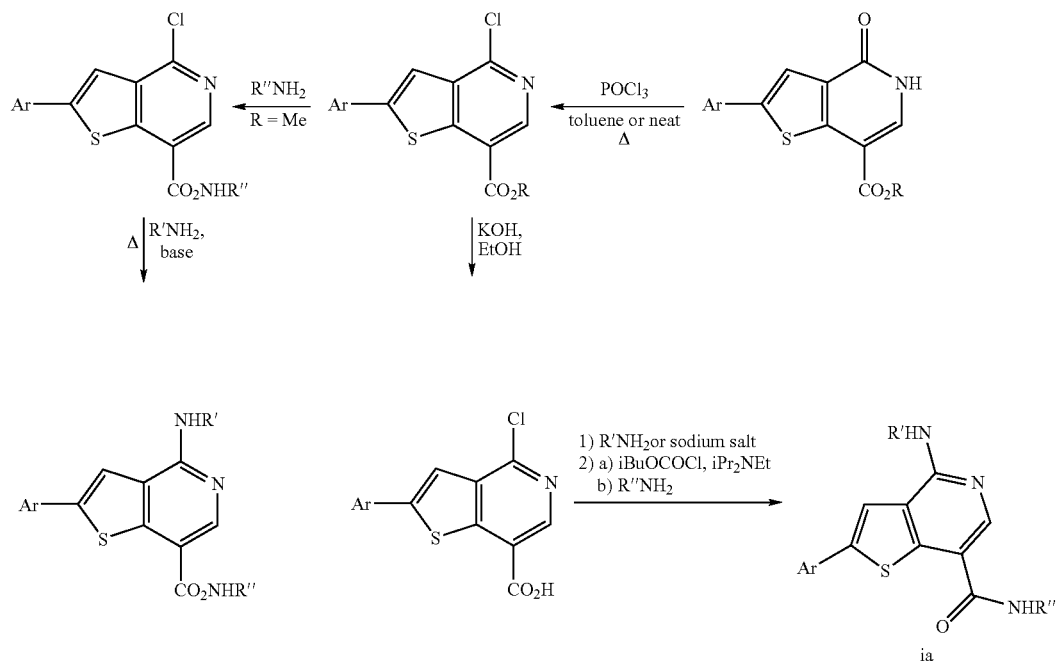
Scheme 1b
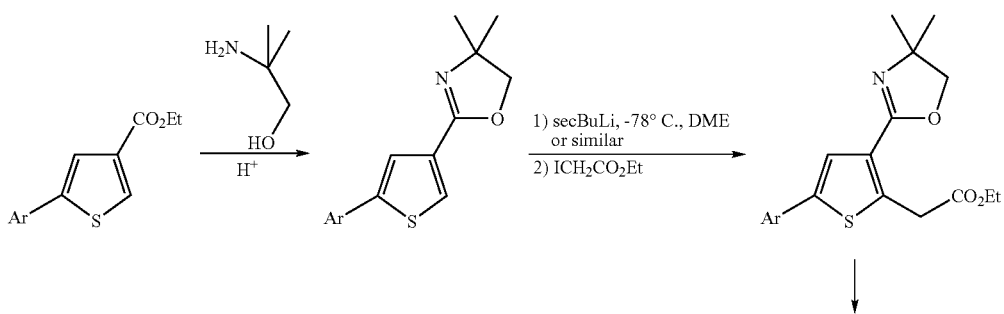

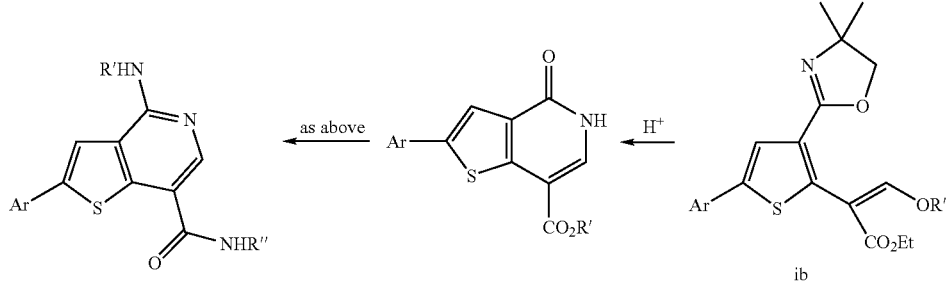
Alternatively, compounds such as ia above, can be prepared by the methods illustrated in Scheme 1c.
Scheme 1c
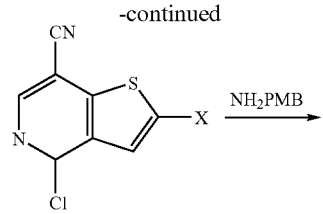

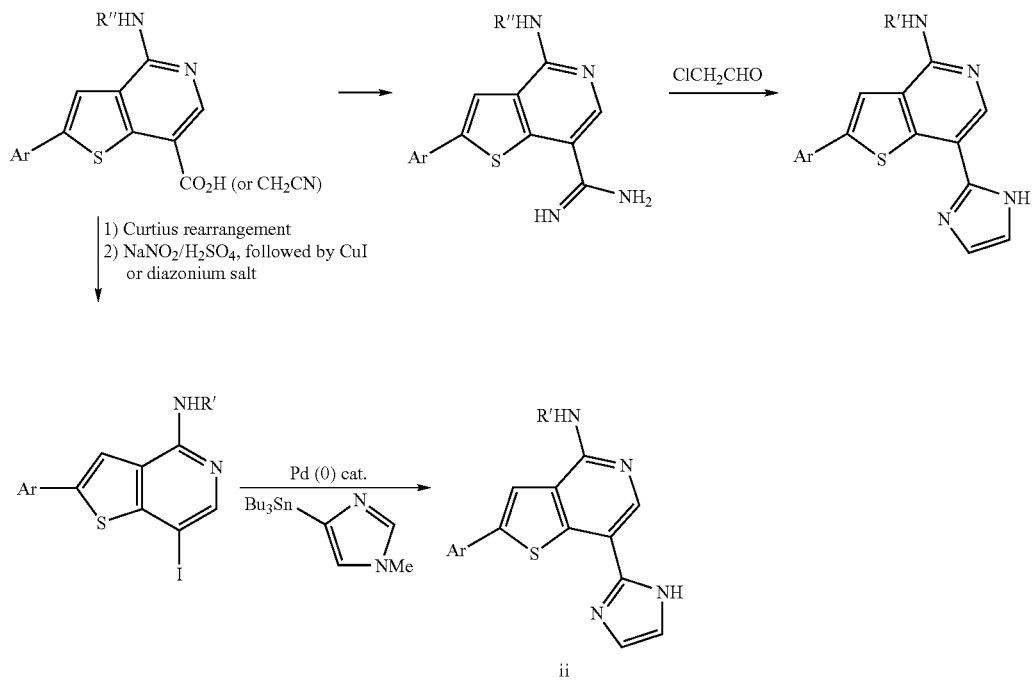
Scheme 2
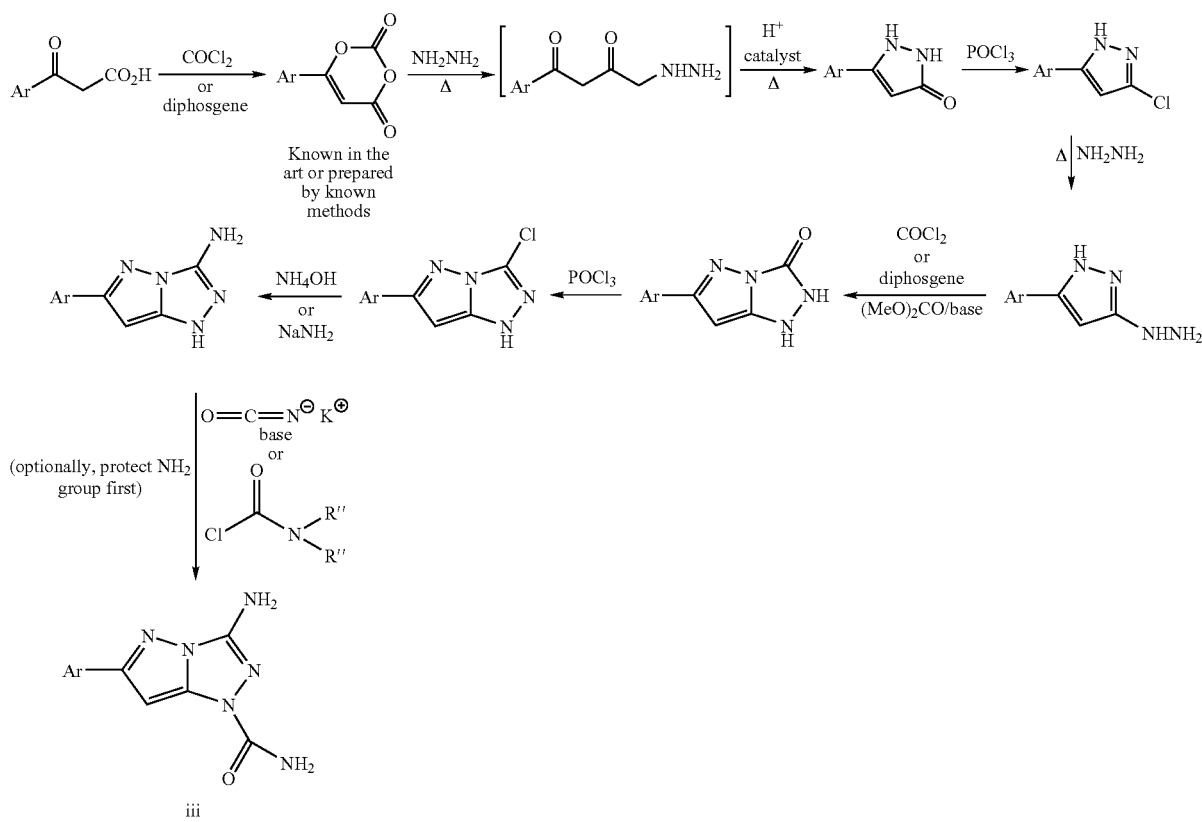
Scheme 3

Scheme 4
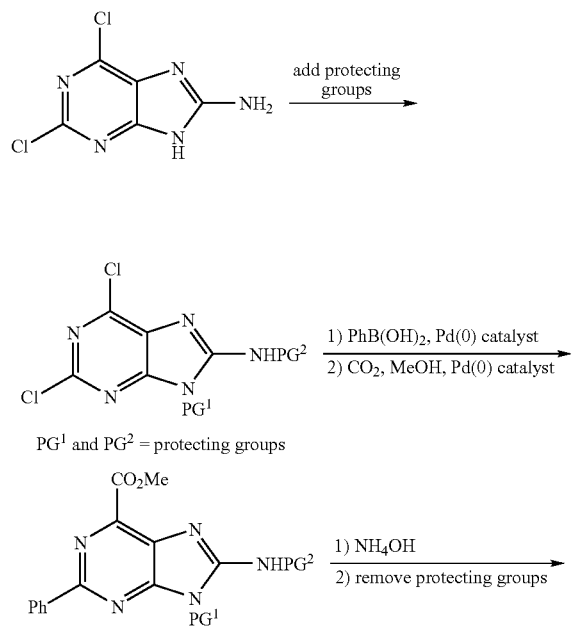
Scheme 5
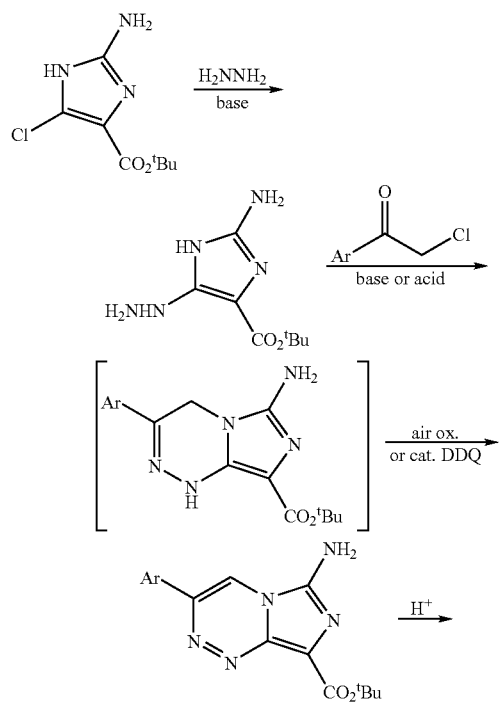
Scheme 6
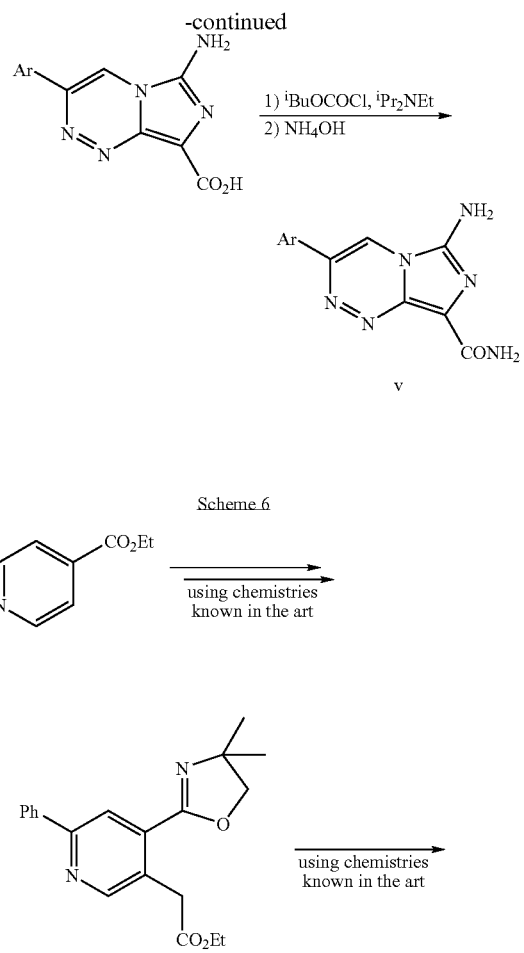

Scheme 7

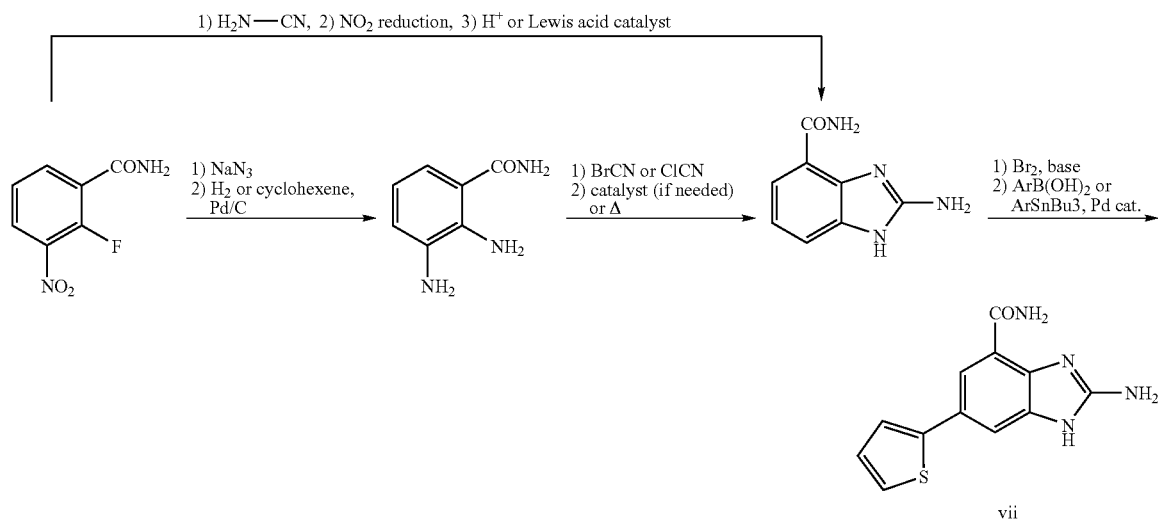

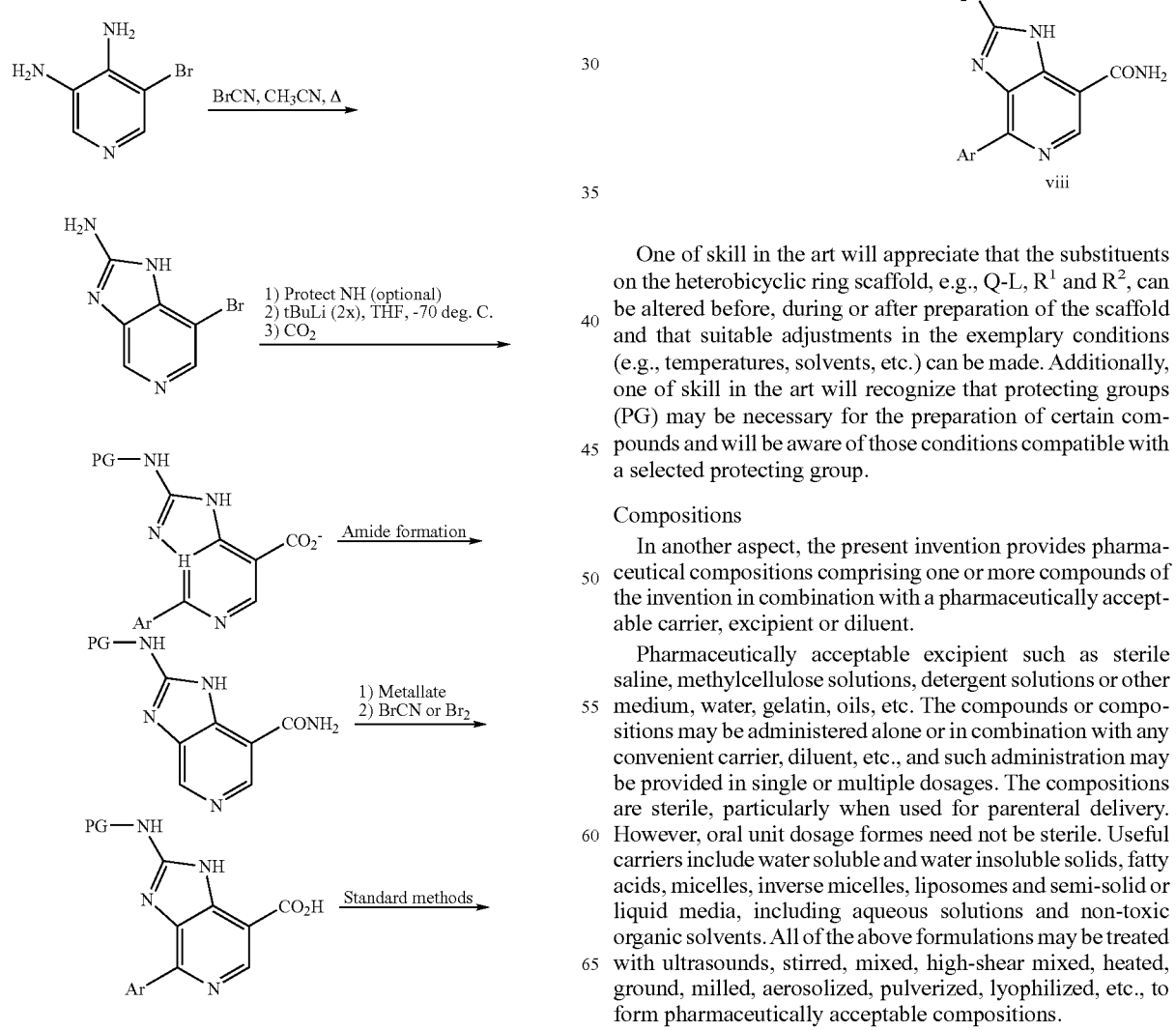

One of skill in the art will appreciate that the substituents on the heterobicyclic ring scaffold, e.g., Q-L, $R^1$ and $R^2$, can be altered before, during or after preparation of the scaffold and that suitable adjustments in the exemplary conditions (e.g., temperatures, solvents, etc.) can be made. Additionally, one of skill in the art will recognize that protecting groups (PG) may be necessary for the preparation of certain compounds and will be aware of those conditions compatible with a selected protecting group.

Compositions

In another aspect, the present invention provides pharmaceutical compositions comprising one or more compounds of the invention in combination with a pharmaceutically acceptable carrier, excipient or diluent.

Pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. The compositions are sterile, particularly when used for parenteral delivery. However, oral unit dosage formes need not be sterile. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc., to form pharmaceutically acceptable compositions.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Still other compositions of the present invention are those that combine two or more of the present compounds in one formulation, or one compound from the present invention with a second antiinflammatory, antiproliferative or antidiabetic agent.

Methods of Use

In yet another aspect, the present invention provides methods of treating or preventing a disease or condition associated with inflammation, a metabolic disorder, infection, cancer or an immune disease or condition by administering to a subject having such a condition or disease, a therapeutically effective amount of a compound or composition of the invention.

In one group of embodiments, diseases or conditions, including chronic diseases, of humans or other species can be treated or prevented with inhibitors of IKK function and/or inhibitors of IRAK function. These diseases or conditions include (1) inflammatory or allergic diseases such as systemic anaphylaxis and hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis and urticaria, (5) vasculitis, (6) spondyloarthropathies, (7) scleroderma, (8) asthma and respiratory allergic diseases such as allergic asthma, allergic rhinitis, allergic conjunctivitis, hypersensitivity lung diseases and the like, and (9) autoimmune diseases, such as arthritis (including rheumatoid and psoriatic), systemic lupus erythematosus, type I diabetes, glomerulonephritis and the like, (10) graft rejection (including allograft rejection and graft-v-host disease), (11) other diseases in which undesired inflammatory responses are to be inhibited, e.g., atherosclerosis, myositis, neurological disorders such as stroke, ischemic reperfusion injury, traumatic brain injury and closed-head injuries, neurodegenerative diseases (e.g., Parkinson's disease), multiple sclerosis, Alzheimer's disease, encephalitis, meningitis, osteoporosis, gout, hepatitis, nephritis, gall bladder disease, sepsis, sarcoidosis, conjunctivitis, otitis, chronic obstructive pulmonary disease, sinusitis and Behcet's syndrome; (12) cell proliferative or neoplastic diseases such as cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system and diseases in which angiogenesis and neovascularization play a role; (13) metabolic disorders that are sensitive to inhibition of TNF or IL-1 signaling, such as obesity, type II diabetes, Syndrome X, insulin resistance, hyperglycemia, hyperuricemia, hyperinsulinemia, cachexia, hypercholesterolemia, hyperlipidemia, dyslipidemia, mixed dyslipidemia and hypertriglyceridemia, eating disorders, such as anorexia nervosa and bulimia, (14) infectious diseases, e.g., bacteremia and septic shock; (15) cardiovascular disorders, such as acute heart failure, hypotension, hypertension, angina pectoris, myocardial infarction, cardiomyopathy, congestive heart failure, atherosclerosis, coronary artery disease, restenosis and vascular stenosis; and (16) immune diseases or conditions.

In one embodiment, the present methods are directed to the treatment or prevention of diseases or conditions selected from rheumatoid arthritis, septic shock, inflammatory bowel disease, bone mass loss, cancer, dermal sensitization disorders, diabetes, obesity, ischemic stroke, ischemic reperfusion injury, closed-head injuries, asthma, allergic disease, multiple sclerosis and graft rejection.

In another embodiment, the present invention provides methods of treating or preventing a disease or condition responsive to IKK modulation, comprising administering to a subject having such a disease or condition, a therapeutically effective amount of one or more of the subject compounds or compositions.

In still another embodiment, the present invention provides methods of treating or preventing a disease or condition mediated by IKK, comprising administering to a subject having such a disease or condition, a therapeutically effective amount of one or more of the subject compounds or compositions.

In another embodiment, the present invention provides methods of modulating IKK comprising contacting a cell with a compound of the invention.

In still other embodiments, the present invention provides methods of treating or preventing a disease or condition responsive to IRAK modulation, comprising administering to a subject having such a disease or condition, a therapeutically effective amount of one or more of the subject compounds or compositions.

In still another embodiment, the present invention provides methods of treating or preventing a disease or condition mediated by IRAK, comprising administering to a subject having such a disease or condition, a therapeutically effective amount of one or more of the subject compounds or compositions.

In yet another embodiment, the present invention provides methods of modulating IRAK comprising contacting a cell with a compound of the invention.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection or implant), inhalation, nasal, vaginal, rectal, sublingual transdermal or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In the treatment or prevention of the above-described diseases and conditions, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Combination Therapy

The compounds of the invention may be combined and/or used in combination with other agents useful in the treatment or prevention of inflammation, metabolic disorders, infection, cancer and those pathologies noted above. In many instances, administration of the subject compounds or pharmaceutical compositions in conjunction with these alternative therapeutic agents enhances the efficacy of such agents. Accordingly, in some instances, the compounds of the invention, when combined or administered in combination with, e.g., antiinflammatory agents, can be used in dosages which are less than the expected amounts when used alone, or less than the calculated amounts for combination therapy.

Likewise, compounds and compositions of the invention may be used in combination with other drugs that are used in the treatment, prevention, suppression or amelioration of the diseases or conditions for which compounds of the invention are useful. Such other drugs may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of therapeutic agents or active ingredients that may be combined with a compound of the invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone and hydrocortisone, and corticosteroid analogs such as budesonide; (c) imrunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $\beta 2$-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone) and cyclooxygenase-2 (COX-2) inhibitors such as celecoxib (Celebrex®) and rofecoxib (Vioxx®); (g) inhibitors of phosphodiesterase type IV; (h) opiod analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (i) cholesterol lowering agents such as HMG-CoA reductase inhibitors (e.g., lovastatin, simvastatin, pravastatin, fluvastatin, atorvastatin and other statins), bile acid sequestrants (e.g., cholestyramine, colestipol and dialkylaminoalkyl derivatives of a cross-linked dextran), vitamin $B_3$ (nicotinic acid or niacin), vitamin $B_6$ (pyridoxine), vitamin $B_{12}$ (cyanocobalamin), fibric acid derivatives (gemfibrozil, clofibrate, fenofibrate and benzafibrate), probucol, nitroglycerin, inhibitors of cholesterol absorption (e.g., beta-sitosterol and acylCoA-cholesterol acyltransferase (ACAT) inhibitors, e.g., melinamide), HMG-CoA synthase inhibitors, squalene epoxidase inhibitors, squalene syntetase inhibitors; (j); antidiabetic agents such as insulin or insulin mimetics, sulfonylureas (e.g., glyburide, meglinatide, tolbutamide and glipizide), biguanides, e.g., metformin (Glucophage®), $\alpha$-glucosidase inhibitors (acarbose), thiazolidinone compounds, e.g., rosiglitazone (Avandia®), troglitazone (Rezulin®), ciglitazone pioglitazone (Actos®) and englitazone; (k) preparations of interferon beta (interferon $\beta$-1 $\alpha$, interferon $\beta$-1 $\beta$); (l) gold compounds such as auranofin and aurothioglucose, (m) etanercept (Enbrel®); (n) antibody therapies such as orthoclone (OKT3), daclizumab (Zenapax®), basiliximab (Simulect®), infliximab (Remicade®) and D2E6 TNF antibody, (o) agents that directly or indirectly interfere with cytokine signalling, such as soluble TNF receptors, TNF antibodies and soluble IL-1; (p) IL-1 receptor antagonists, e.g., anakinra (Kineret®); (q) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (r) multiple sclerosis therapeutic agents such as interferon $\beta$-1$\beta$ (Betaseron®), interferon $\beta$-1$\alpha$ (Avonex®), azathioprine (Imurek®, Imuran®), glatiramer acetate (Capoxone®), a glucocorticoid (e.g., prednisolone) and cyclophosphamide; (s) anti-obesity agents such as fenfluramine, dexfenfluramine, phentermine, sibutramine, gastrointestinal lipase inhibitors (e.g., orlistat), phenylpropanolamine, diethylprorion, mazindol, $\beta$3 adrenergic receptor agonists, leptin or derivatives thereof and neuropeptide Y antagonists (e.g., NPY5); (t) other IKK inhibitors, especially IKK$\alpha$ inhibitors; (u) antineoplastic agents, such as DNA alkylating agents (e.g., mechlorethamine, chlorambucil, cyclophosphamide, melphalan and ifosfamide), antimetabolites (e.g., methotrexate, azathioprine, 6-mercaptopurine, 5-fluorouracil, cytarabine and gemcitabine), microtubule disruptors and/or spindle poisons (e.g., vinblastine, vincristine, vinorelbine, colchicine, nocodazole, paclitaxel, docetaxel, etoposide, irinotecan and topotecan), DNA intercalators (e.g., doxorubicin, daunomycin, bleomycin, mitomycin, cisplatin and carboplatin), nitrosoureas (e.g., carmustine and lomustine), interferon, aspariginase and hormones (e.g., tamoxifen, leuoprolide, flutamide and megestrol acetate); (v) antithrombotic agents such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors, vasodilators (e.g., sodium nitroprusside, nicardipine hydrochloride, nitroglycerin and enaloprilat); (w) recombinant tissue plasminogen activator (tPA); (x) cholinesterase inhibitors, such as galantamine (Reminyl®), donepezil hydrochloride (Aricept®) and rivastigmine (Exelon®); (y) anticholinergic agents (e.g., diphenhydramine, orphenadrine, amitriptyline, doxepin, imipramine, nortriptyline, benztropine, biperiden, ethopropazine, procyclidine and trihexyphenidyl), dopaminergic agents (e.g., carbidopa/levodopa, bromocriptine and pergolide), selegiline and amantadine; and (z) other compounds such as 5-aminosalicylic acid; and prodrugs thereof. In preferred embodiments, the second agent is selected from prednisone, dexamethasone, beclomethasone, methylprednisone, betamethasone, hydrocortisone, methotrexate, cyclosporin, rapamycin, tacrolimus, an antihistamine, a TNF antibody, an IL-1 antibody, a soluble TNF receptor, a soluble IL-1 receptor, a TNF or IL-1 receptor antagonist, a non-steroidal anti-inflammatory agent, a COX-2 inhibitor, an antidiabetic agent, an anticancer agent, hydroxycloroquine, D-penicillamine, infliximab, etanercept, auranofin, aurothioglucose, sulfasalazine, sulfasalazine analogs, mesalamine, corticosteroids, corticosteroid analogs, 6-mercaptopurine, interferon β-1β, interferon β-1α, azathioprine, glatiramer acetate, a glucocorticoid and cyclophosphamide.

The weight ratio of the compound of the compound of the present invention to the second active ingredient may be varied and will depend upon the effective dose of each ingredient. Generally, an effective dose of each will be used. Thus, for example, when a compound of the invention is combined with an NSAID the weight ratio of the compound of the invention to the NSAID will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

The following examples are offered by way of illustration and are not intended to limit the scope of the invention. Those of skill in the art will readily recognize a variety of noncritical parameters that could be modified to yield essentially similar results.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter (μL) was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent. Reverse phase HPLC was carried out using a Rainin Dynamax Model SD-300 with a Capcell Pak C18 column as the stationary phase and eluting with acetonitrile:H$_2$O:0.1% TFA. Detection was carried out using a Dynamax UV detector at 254 nM.

Example 1

Preparation of 4-Amino-2-phenyl-1-H-imidazole[4,5-c]pyridine-7-carboxylic acid amide TFA salt

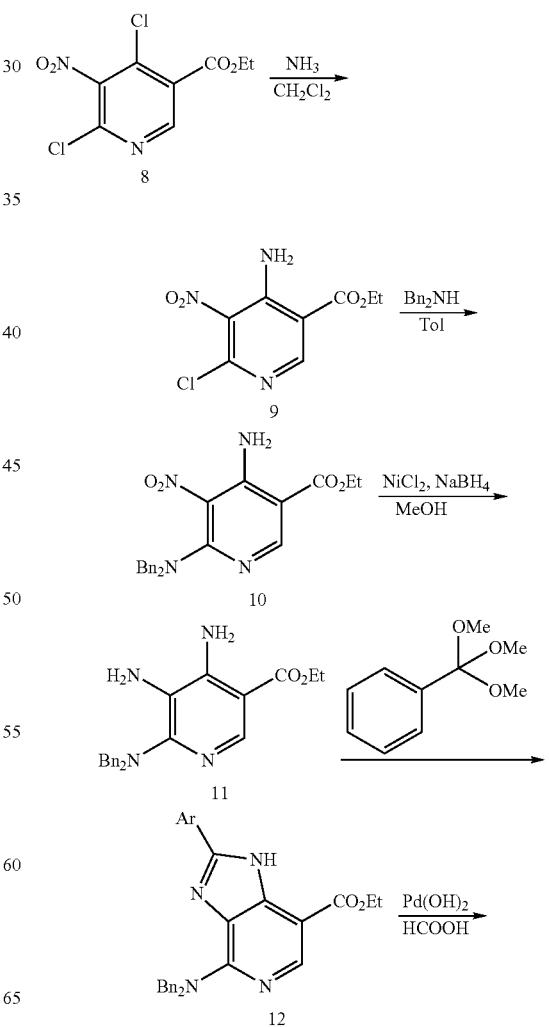

-continued

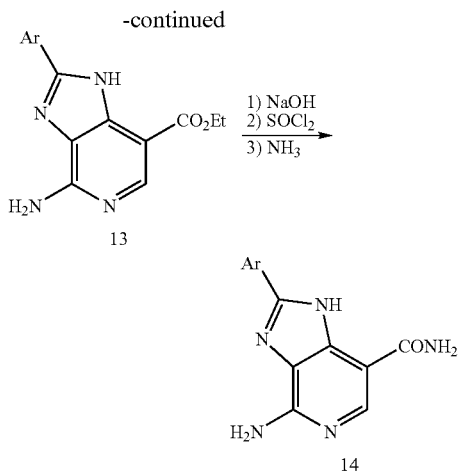

4,6-Dichloro-2-methyl-5-nitro-pyridine-3-carboxylic acid (8). 4,6-Dichloro-2-methyl-5-nitro-pyridine-3-carboxylic acid was prepared according to the procedure described in U.S. Pat. No. 3,891,660.

4-Amino-6-chloro-5-nitro-pyridine-3-carboxylic acid ethyl ester (9). To a solution of 4,6-Dichloro-2-methyl-5-nitro-pyridine-3-carboxylic acid (15 g, 56.6 mmol) and triethylamine (7.9 mL, 57.3 mmol) in dichloromethane (84 mL) at 0° C. was added dropwise ammonia solution in dioxane (0.5 M, 113 mL, 56.5 mmol). The mixture was then stirred overnight. Removal of the solvent followed by column chromatography gave 9 as a yellow crystalline solid. (7.3 g). $^1$H-NMR δ: 1.32 (t, J=7.1 Hz, 3H), 4.33 (q, J=7.1 Hz, 2H), 8.06 (s, br, 2H), 8.62 (s, 1H).

4-Amino-6-bis(phenylmethyl)amino-5-nitro-pyridine-3-carboxylic acid ethyl ester (10). Dibenzylamine (1.95 mL, 10 mmol), triethylamine (1.37 mL, 10 mmol), 4-amino-6-chloro-5-nitro-pyridine-3-carboxylic acid ethyl ester (2.45 g, 10 mmol) and toluene (73 mL) were combined and heated at reflux over night. The reaction mixture was cooled to room temperature and filtered through a short column of silica gel (eluting first with dichloromethane then ethyl acetate). The organics were concentrated to provide 10 as a yellow oil (4.2 g). $^1$H NMR (400 MHz, d$^6$-DMSO) δ: 1.28 (t, J=7.1 Hz, 3H), 4.25 (q, J=7.1 Hz, 2H), 4.60 (s, 4H), 7.14-7.31 (m, 10H), 8.35 (s, br, 2H), 8.54 (s, 1H).

6-Bis(phenylmethyl)amino-4,5-diamino-pyridine-3-carboxylic acid ethyl ester (11). Sodium borohydride (151 mg, 4.1 mmol) was added to a solution of nickel (II) chloride hydrate (261 mg, 1.1 mmol) in MeOH (26 mL). After 30 min. at room temperature, a solution of 4-amino-6-bis(phenylmethyl)amino-5-nitro-pyridine-3-carboxylic acid ethyl ester (0.9 g, 2.2 mmol) in dichloromethane (5 mL) was added followed by the addition of sodium borohydride (353 mg). The mixture was stirred over night then filtered through a layer of silica gel. The organic was diluted with dichloromethane, washed with brine and dried over sodium sulfate. The organics were filtered, concentrated and purified by column chromatography (dichloromethane:methanol, 20:1). 11 was obtained as a white solid (200 mg). $^1$H NMR (400 MHz, d$^6$-DMSO) δ: 1.26 (t, J=7.1 Hz, 3H), 4.21 (s, 4H), 4.22 (q, J=7.1 Hz, 2H), 4.52 (s, 2H), 6.73 (s, 2H), 7.14-7.31 (m, 10H), 8.01 (s, 1H). ESIMS, M/Z, 377 (M+1)$^+$.

4-Bis(phenylmethyl)amino-2-phenyl-1-H-imidazole[4,5-c]pyridine-7-carboxylic acid ethyl ester (12). 6-Bis(phenylmethyl)amino-4,5-diamino-pyridine-3-carboxylic acid ethyl ester (200 mg, 0.53 mmol) was heated with trimethyl orthobenzoate (5 mL) at 130° C. for 10 h. The excess solvent was removed and residue was purified by column (dichloromethane). A white solid, 12, was obtained (60 mg). $^1$H NMR (400 MHz, d$^6$-DMSO) δ: 1.36 (t, J=7.1 Hz, 3H), 4.39 (q, J=7.1 Hz, 2H), 5.30 (s, br, 4H), 7.23-7.35 (m, 10H), 7.40-7.50 (m, 3H), 8.14-8.16 (m, 2H), 8.45 (s, 1H). ESIMS, M/Z, 463 (M+1)$^+$.

4-Amino-2-phenyl-1-H-imidazole[4,5-c]pyridine-7-carboxylic acid ethyl ester TFA salt (13). 4-Bis(phenylmethyl)amino-2-phenyl-1-H-imidazole[4,5-c]pyridine-7-carboxylic acid ethyl ester (59 mg, 0.13 mmol) was treated with Pd(OH)$_2$ (15 mg, 0.11 mmol) in formic acid (2 mL) and heated at reflux over night. Another portion of Pd(OH)$_2$ (15 mg, 0.11 mmol) was added to the reaction. The mixture was heated at refluxing overnight. This procedure was repeated an additional 3 times until the reaction was complete. Removal of the solvent followed by purification using reverse phase HPLC provided the TFA salt of 13 (20 mg) as a white solid. $^1$H NMR (400 MHz, d$^6$-DMSO) δ: 1.37 (t, J=7.1 Hz, 3H), 4.42 (q, J=7.1 Hz, 2H), 7.50-7.60 (m, 3H), 8.20-8.30 (m, 2H), 8.31 (s, 1H). ESIMS, M/Z, 283 (M+1)$^+$.

4-Amino-2-phenyl-1-H-imidazole[4,5-c]pyridine-7-carboxylic acid amide TFA salt (14). 4-Amino-2-phenyl-1-H-imidazole[4,5-c]pyridine-7-carboxylic acid ethyl ester TFA salt (20 mg, 0.05 mmol) was treated with 1N NaOH (1 mL) and MeOH (1 mL) and heated at reflux for 1 hr. Solvent was removed and the residue was acidified to pH 2. The white solid was filtered, dried under vacuum and treated with SOCl$_2$ (1 mL) and heated at reflux for 1 h. Solvent was then removed and the residue was treated with ammonia in dioxane (0.5 M, 2 mL). Removal of solvent and purification by reverse phase HPLC provided 14 (10 mg) as a white solid. $^1$H NMR (400 MHz, d$^6$-DMSO) δ: 7.50-7.60 (m, 3H), 7.80 (s, br, 1H), 8.15-8.35 (m, 4H), 8.75 (s, br, 2H). ESIMS, M/Z, 254 (M+1)$^+$.

Example 2

Preparation of 7-carboxamido-4-amino-2-[3,4,5-trimethoxy]phenyl-thieno[3,2-c]pyridine

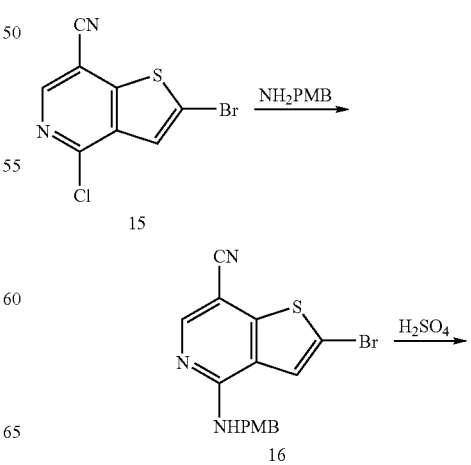

47

-continued

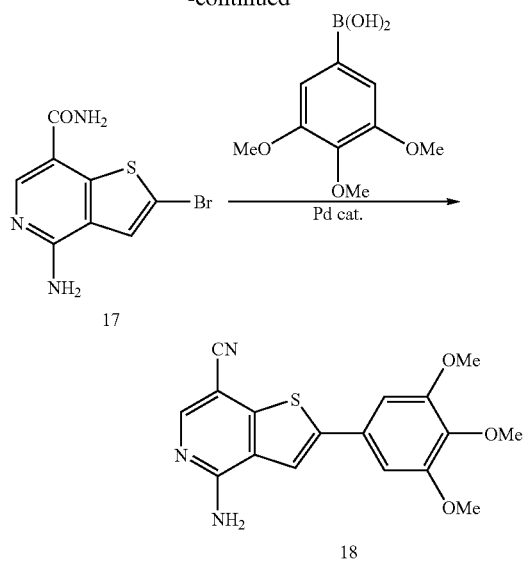

2-Bromo-4-chloro-7-cyanothieno[3,2-c]pyridine (15). 2-bromo-4-chloro-7-cyanothieno[3,2-c]pyridine, 15 was prepared according to the procedure described in U.S. Pat. No. 3,9803,095.

2-Bromo-7-cyano-4-p-methoxybenzylaminothieno[3,2-c]pyridine (16). To a stirred solution of 4-methoxybenzylamine (1.2 equiv., 2.4 mmol) and $K_2CO_3$ (2.4 equiv., 4.8 mmol) in 5 mL anhydrous 1-methyl-2-pyrrolidinone was added 15 (1 equiv., 2 mmol). The mixture was heated at 130° C. under $N_2$ for 1.5 h, allowed to cool, and the product precipitated by the addition of $H_2O$ (5 mL). The mixture was filtered, washed with water, and dried, yielding 16 (1.33 mmol) as a brown solid. $^1$H NMR (400 MHz, $d^6$-DMSO) δ: 8.75 (1H, t, broad), 8.56 (1H, s), 8.21 (1H, s), 7.43 (2H, d, J=8.6 Hz), 7.04 (2H, d, J=8.6), 4.84 (2H, d, J=5.8), 3.88 (3H, s).

2-Bromo-7-carboxamido-4-amino-thieno[3,2-c]pyridine hydrogensulfate salt (17). 1 mL concentrated $H_2SO_4$ was added to 16 (250 mg) and the mixture stirred at room temperature for 1.5 h. Approx. 3 mL of ice was added to the reaction flask. The gray precipitate was filtered and washed with water to yield 110 mg of the hydrogensulfate salt of 17. $^1$H NMR (400 MHz, $d^6$-DMSO) δ: 8.63 (1H, s), 8.30 (1H, broad s), 8.19 (2H, broad d), 8.12 (1H, s), 7.78 (1H, broad s).

7-Carboxamido-4-amino-2-[3,4,5-trimethoxy]phenylthieno[3,2-c]pyridine (18). 3,4,5 trimethoxybenzene boronic acid (1.2 equiv., 0.35 mmol) was added to a mixture of 17 (1 equiv., 0.3 mmol) and $K_2CO_3$ (2.5 equiv., 0.75 mmol) in 1 mL DMF and 0.5 mL $H_2O$. The mixture was degassed for 10 min. with $N_2$, and $PdCl_2(dppf):DCM$ complex was added. The mixture was heated at 85° C. under $N_2$ for 30 min. The mixture was cooled to ambient temperature, diluted with water, filtered, and the precipitate purified further by recrystallization from DMF/$H_2O$. Filtration and washing with water and ethanol yielded 18 as a brown solid. $^1$H NMR (400 MHz, $d^6$-DMSO) δ: 8.65 (1H, s), 8.19 (1H, s), 8.14 (1H, broad, s), 7.42 (1H, broad, s), 7.28 (1H, s), 7.13 (1H, s), 4.06 (2H, s), 3.88 (1H, s).

48

Example 3

Preparation of 4-amino-2-(4-methyl-thiophen-2-yl)-thieno[3,2-c]pyridine-7-carboxylic acid amide

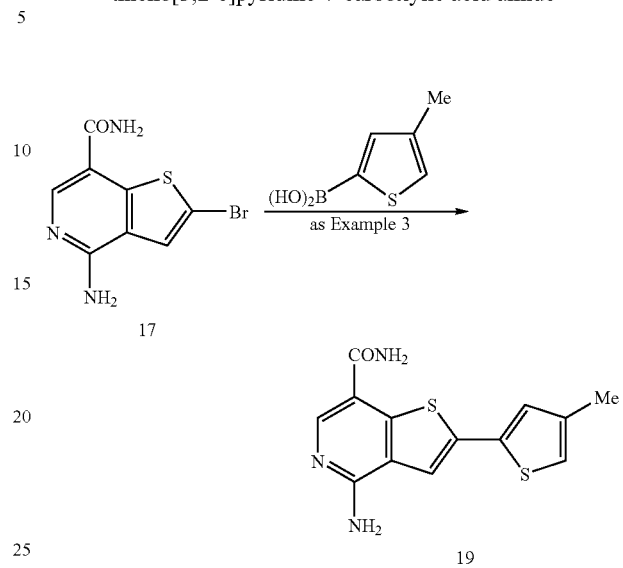

4-Amino-2-(4-methyl-thiophen-2-yl)thieno[3,2-c]pyridine-7-carboxylic acid amide (19). 19 was prepared from 4-amino-2-bromo-thieno[3,2-c]pyridine-7-carboxylic acid amide 17 and 4-methyl-2-thiopheneboronic acid according to the general procedure described in Example 2. $^1$H NMR (400 MHz, $d^6$-DMSO) δ: 2.25 (s, 3H), 7.29 (s, 1H), 7.36 (s, 1H), 7.80 (br s, 1H), 8.14 (s, 1H), 8.40 (br s, 1H), 8.46 (s, 1H). MS (EI) m/z (M+H$^+$) 290.

Example 4

Preparation of 4-Amino-2-prop-1-ynyl-thieno[3,2-c]pyridine-7-carboxylic acid amide

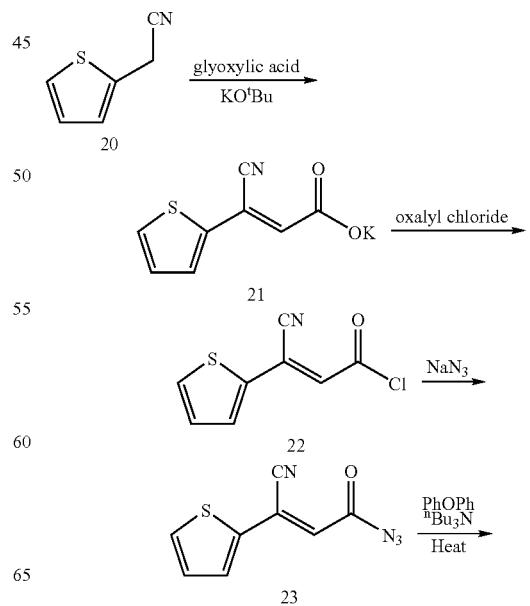

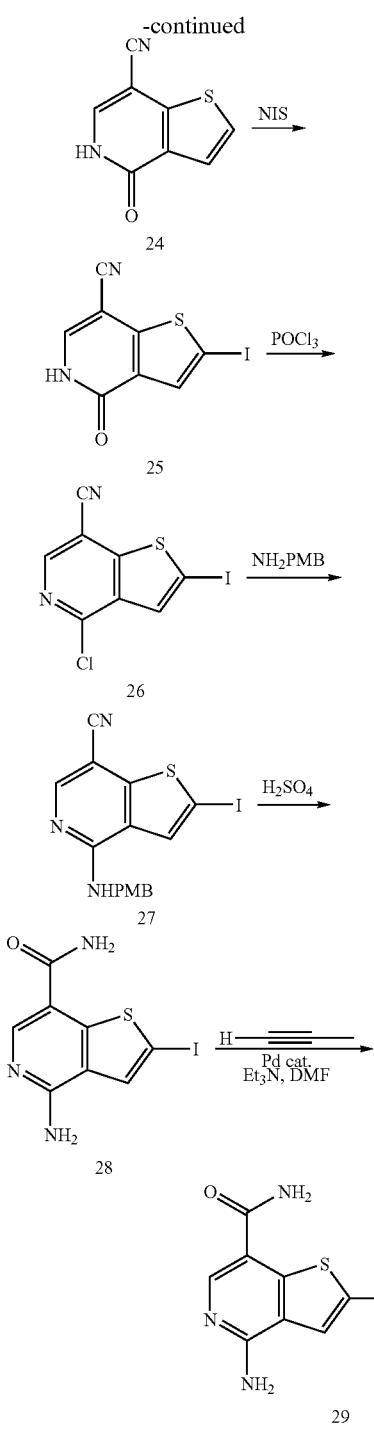

3-Cyano-3-thiophen-2-yl-acryloyl chloride (22). To a stirring solution of oxalyl chloride (81.17 mL, 0.93 mol) in $CH_2Cl_2$ (350 mL) was added 3-cyano-3-thiophen-2-yl-acrylic acid potassium salt 21 (100 g, 0.45 mol) portion-wise over 20 min. An additional 250 mL of $CH_2Cl_2$ were added to assist stirring. The slurry was stirred at room temperature for 30 min and was then filtered. The potassium chloride salts were washed with copious $CH_2Cl_2$. Collected organic rinses were combined and solvent removed under vacuum to afford 84.3 g of 22, which was carried on to the next step without further purification.

3-Cyano-3-thiophen-2-yl-acryloyl azide (23). To a vigorously stirring suspension of $NaN_3$ (55 g, 0.85 mol) in 1:1; dioxane:$H_2O$ (200 mL) cooled to 0° C. was added dropwise over 20 min a solution of 3-cyano-3-thiophen-2-yl-acryloyl chloride 22 (84.3 g, 0.428 mol) in dioxane (150 mL). After stirring at 0° C. for 20 min, the reaction was warmed to room temperature and stirred for 1 h. To the reaction solution was added 600 mL $H_2O$, thus producing a precipitate which was filtered, washed with $H_2O$ and dried under vacuum to provide pure 85 g of 23.

4-Oxo-4,5-dihydro-thieno[3,2-c]pyridine-7-carbonitrile (24). To a stirring solution of diphenyl ether (1.5 L) and trin-butylamine (0.3 L) heated to an equilibrated temperature of 215° C. was dropwise added a solution of 3-cyano-3-thiophen-2-yl-acryloyl azide 23 (85 g, 0.416 mol) in $CH_2Cl_2$ (340 mL). The temperature was maintained between 210-215° C. during this time. Following addition, the reaction was stirred a further 30 min, then allowed to cool to room temperature, during which the pure product precipitated from solution. The product was filtered and washed with copious hexane. Drying the precipitate under vacuum provided 58.4 g of 24. $^1H$ NMR (400 MHz, $d^6$-DMSO) δ 12.36 (s, 1H), 8.27 (s, 1H), 7.81 (d, J=5 Hz, 1H), 7.57 (d, J=5 Hz 1H).

2-Iodo-4-oxo-4,5-dihydro-thieno[3,2-c]pyridine-7-carbonitrile (25). To 4-oxo-4,5-dihydro-thieno[3,2-c]pyridine-7-carbonitrile 24 (5 g, 28.4 mmol) in a 1:1 solution of acetic acid and DMF (18.4 mL) was added N-iodosuccinimide (12.8 g, 56.8 mmol). The reaction was warmed to 80° C. and stirred for 21 h. The reaction was diluted 10 fold with water and neutralized with aqueous sodium bicarbonate. The precipitate was filtered, washed with water and dried to provide 7.27 g of 25. $^1H$ NMR (400 MHz, $d^6$-DMSO) δ 12.45 (s, 1H), 8.25 (d, J=5 Hz, 1H), 7.77 (s, 1H).

4-Chloro-2-iodo-thieno[3,2-c]pyridine-7-carbonitrile (26). To 2-iodo-4-oxo-4,5-dihydro-thieno[3,2-c]pyridine-7-carbonitrile 25 (7.75 g, 25.6 mmol) was added $POCl_3$ (90 mL). The reaction was stirred under reflux overnight. $POCl_3$ was removed by rotary evaporation followed by suspension of solids in $H_2O$ (500 mL) and filtration. The solids were washed with copious amounts of $H_2O$, saturated bicarbonate solution, and washed further with $H_2O$ to provide upon drying 7.52 g of 26. $^1H$ NMR (400 MHz, $d^6$-DMSO) δ 8.82 (s, 1H), 8.06 (s, 1H).

2-Iodo-4-(4-methoxybenzylamino)-thieno[3,2-c]pyridine-7-carbonitrile (27). To NMP (41.3 mL) and 4-methoxybenzylamine (3.66 mL, 28.1 mmol) was added $K_2CO_3$ (7.76 g, 56.2 mmol) and 4-chloro-2-iodo-thieno[3,2-c]pyridine-7-carbonitrile 26 (7.52 g, 23.4 mmol). The reaction was heated to 80° C. After 1.5 h, NMP was distilled away under reduced pressure. The resulting solids were suspended in $H_2O$ (500 mL) and filtered. The product was recrystallized from 350 mL of toluene to obtain 7.75 g of 27. $^1H$ NMR (400 MHz, $d^6$-DMSO) δ 8.58 (t, J=6 Hz, 1H), 8.35 (s, 1H), 8.17 (s, 1H), 7.28 (d, J=9 Hz, 2H), 6.89 (d, J=9 Hz, 2H), 4.68 (d, J=6 Hz, 2H), 3.37 (s, 3H).

3-Cyano-3-thiophen-2-yl-acrylic acid potassium salt (21). To a stirring solution of thiophene-2-acetonitrile 20 (Aldrich, Milwaukee, Wis.) (80.6 g, 0.655 mol) in MeOH (1.3 L) was added glyoxylic acid (63.3 g, 0.688 mol). To the reaction solution was added portion-wise over 10 minutes potassium tert-butoxide (77.2 g, 0.688 mol). A nitrogen atmosphere was applied, and the solution was brought to reflux. After 6 h, the reaction was warmed to room temperature, filtered, and washed with copious amounts of MeOH. After drying under reduced pressure, 100 g of 21 as a white crystalline solid was obtained.

4-Amino-2-iodo-thieno[3,2-c]pyridine-7-carboxylic acid amide (28). To 2-iodo-4-(4-methoxy-benzylamino)-thieno[3,2-c]pyridine-7-carbonitrile 27 (3.88 g, 9.21 mmol) was added conc. H$_2$SO$_4$ (9.75 mL). The reaction was stirred for 1 h at room temperature, then quenched by the addition of ice (20 g). The filtered precipitate was washed with H$_2$O, then suspended in 30% MeOH—CH$_2$Cl$_2$ (30 mL). Triethylamine was added dropwise until the solids dissolved. The solution was purified by silica gel column chromatography (eluent: 10 to 20% MeOH in CH$_2$Cl$_2$ with 1% NH$_4$OH additive) to yield 2.6 g of 28. $^1$H NMR (400 MHz, d$^6$-DMSO) δ 8.46 (s, 1H), 7.94 (m, 2H), 7.31 (bs, 1H), 7.18 (s, 2H).

4-Amino-2-prop-1-ynyl-thieno[3,2-c]pyridine-7-carboxylic acid amide (29). A flask containing 4-amino-2-iodo-thieno[3,2-c]pyridine-7-carboxylic acid amide 28 (0.075 g, 0.24 mmol), PdCl$_2$(PPh$_3$)$_2$ (0.014 g, 0.018 mmol), and CuI (0.0034 g, 0.018 mmol) in DMF (0.75 mL) and TEA (0.1 mL) was evacuated and purged to a propyne atomsphere at 760 Torr. The reaction was stirred overnight, then H$_2$O (10 mL) added. The precipitate was collected dried and purified by silica gel column chromatography (eluent: 10% MeOH, 1% NH$_4$OH in CH$_2$Cl$_2$) to afford 0.039 mg of 29. $^1$H NMR (400 MHz, d$^6$-DMSO) δ 8.53 (s, 1H), 7.90 (bs, 1H), 7.73 (s, 1H), 7.23 (m, 3H), 2.14 (s, 3H).

Example 5

Preparation 4-Amino-2-cyclopent-1-enyl-thieno[3,2-c]pyridine-7-carboxylic acid amide

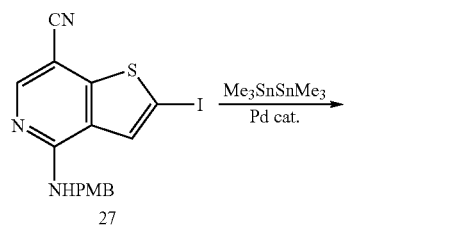

27

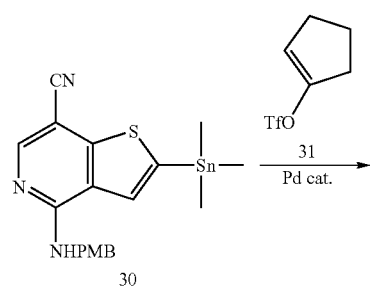

30

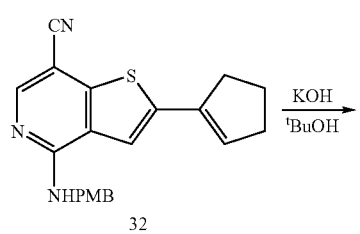

32

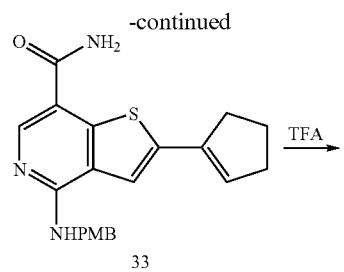

33

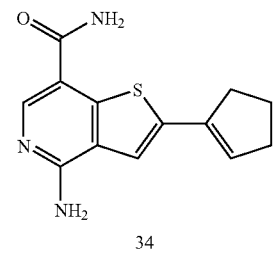

34

4-(4-Methoxy-benzylamino)-2-(trimethyl-stannanyl)thieno[3,2-c]pyridine-7-carbonitrile (30). To 2-Iodo-4-(4-methoxy-benzylamino)-thieno[3,2-c]pyridine-7-carbonitrile (1.0 g, 2.37 mmol) 27 in N$_2$ sparged THF (8 mL) was added Pd—Cl$_2$(PPh$_3$)$_2$ (0.083 g, 0.12 mmol), then hexamethylditin (0.93 g, 2.84 mmol). The reaction was stirred at room temperature for 1.5 h. The reaction contents were diluted with CH$_2$Cl$_2$ (24 mL) and filtered. The solvents were then removed by rotary evaporation. Silica gel column chromotagraphy (eluent: 1:1; Et$_2$O:hexanes) provided 48 mg of 30. $^1$H NMR (400 MHz, CDCl$_3$) δ 8.32 (s, 1H), 7.36 (d, J=8 Hz, 2H), 7.29 (s, 1H), 6.93 (d, J=8 Hz, 2H), 5.50 (m, 1H), 4.80 (d, J=5 Hz, 2H), 3.84 (s, 3H), 0.46 (s, 9H).

2-Cyclopent-1-enyl-4-(4-methoxy-benzylamino)-thieno[3,2-c]pyridine-7-carbonitrile (32). A solution of degassed THF (9.5 mL) containing 4-(4-methoxy-benzylamino)-2-(trimethyl-stannanyl)-thieno[3,2-c]pyridine-7-carbonitrile 30 (0.19 g, 0.49 mmol) and trifluoromethanesulfonic acid cyclopent-1-enyl ester 31 (Adah et al., Tetrahedron, 1997, 53, 6747) (0.32 g, 1.46 mmol) was added to a separate flask containing a nitrogen sparged suspension of Pd(PPh)$_4$ (0.041 g, 0.036 mmol), LiCl (0.42 g, 10 mmol) in THF (9.5 mL). The suspension was brought to reflux under nitrogen atmosphere for 12 h resulting in consumption of the tin reagent. A three fold volume of 10% ethyl acetate in CH$_2$Cl$_2$ was added to the cooled suspension. After filtration, solvent was removed in vacuo. Silica gel column chromatography (eluent: 2.5-5% ethyl acetate in CH$_2$Cl$_2$) followed by vigorous extraction from saturated KF solution provided 75 mg of 32. $^1$H NMR (400 MHz, CDCl$_3$) δ 8.32 (s, 1H), 7.34 (d, J=8 Hz, 2H), 6.94 (d, J=8 Hz, 2H), 6.90 (s, 1H) 6.20 (t, J=2 Hz, 1H) 5.41 (m, 1H), 4.77 (d, J=5 Hz, 2H), 3.84 (s, 3H), 2.74 (m, 2H), 2.60 (m, 2H), 2.08 (p, J=7 Hz, 2H).

2-Cyclopent-1-enyl-4-(4-methoxy-benzylamino)-thieno[3,2-c]pyridine-7-carboxylic acid amide (33). 2-Cyclopent-1-enyl-4-(4-methoxy-benzylamino)-thieno[3,2-c]pyridine-7-carbonitrile 32 (0.020 g, 0.055 mmol), crushed KOH (0.10 g) and tert-butanol (1.5 mL) was brought to reflux for 45 minutes. The reaction mixture was diluted with CH$_2$Cl$_2$ (20 mL) and extracted with H$_2$O (5 mL). The organic layer was concentrated in vacuo to provide 33. $^1$H NMR (400 MHz, CDCl$_3$) δ 8.37 (s, 1H), 7.34 (d, J=8 Hz, 2H), 6.91 (m, 3H), 6.24 (m, 1H), 5.93 (bs, 2H), 5.37 (t, J=5 Hz, 1H), 4.78 (d, J=5 Hz, 2H), 3.83 (s, 3H), 2.73 (m, 2H), 2.57 (m, 2H), 2.04 (p, J=7 Hz, 2H).

4-Amino-2-cyclopent-1-enyl-thieno[3,2-c]pyridine-7-carboxylic acid amide (34). To 2-cyclopent-1-enyl-4-(4-methoxy-benzylamino)-thieno[3,2-c]pyridine-7-carboxylic acid amide 33 (21 mg, 0.055 mmol.) was added TFA (2 mL) and the solution was heated to 50° C. for 1 h. Solvents were removed in vacuo. Silica gel column chromotagraphy (eluent: 1 NH$_4$OH, 7% MeOH in CH$_2$Cl$_2$) provided 1.1 mg of 34. $^1$H NMR (400 MWz, d$^6$-DMSO) δ 8.46 (s, 1H), 7.89 (bs, 1H), 7.51 (s, 1H), 7.24 (bs, 1H), 7.12 (bs, 2H), 6.15 (m, 1H), 2.72 (m, 2H), 2.53 (m, 2H), 2.01 (p, J=7 Hz, 2H).

Example 6

Preparation of 4-amino-2-cyclopentyl-thieno[3,2-c]pyridine-7-carboxylic acid amide

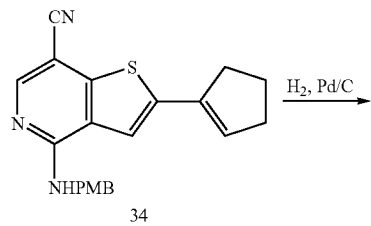

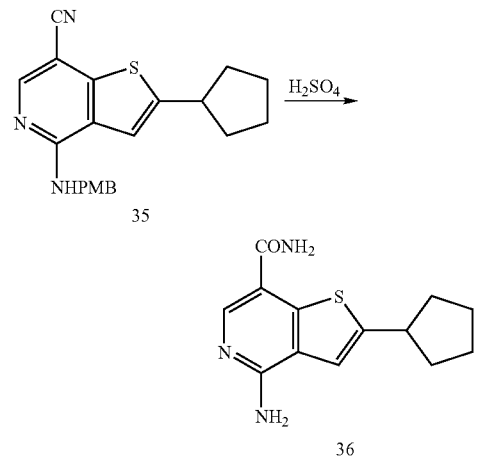

4-Amino-2-cyclopentyl-thieno[3,2-c]pyridine-7-carboxylic acid amide (36). A suspension of 4-amino-2-cyclopent-1-enyl-thieno[3,2-c]pyridine-7-carboxylic acid amide 34 (prepared in example 6 above) (0.056 g, 0.155 mmol) and 10% palladium on carbon (5 mol %) in DMF (1 mL) was stirred under H$_2$ (1 atm) for 20 h. The suspension was diluted with MeOH (10 mL) and filtered. Solvent was removed in vacuo. To the crude solid of 35 was added concentrated H$_2$SO$_4$ (0.25 mL). The purple solution was stirred for 1 h followed by the addition of ice (2 g). The precipitate was filtered then purified by silica gel column chromatography (eluent: 10% MeOH, 1% NH$_4$OH in CH$_2$Cl$_2$) and converted to the HCl salt to afford 12.5 mg of 36. $^1$H NMR (400 MHz, d$^6$-DMSO) δ 8.76 (s, 2H), 8.45 (s, 1H), 8.29 (s, 1H), 7.75 (m, 3H), 3.37 (m, 1H), 2.14 (m, 2H), 1.72 (m, 6H).

Example 7

Preparation of 4-Amino-2-imidazol-1-yl-thieno[3,2-c]pyridine-7-carboxylic acid amide

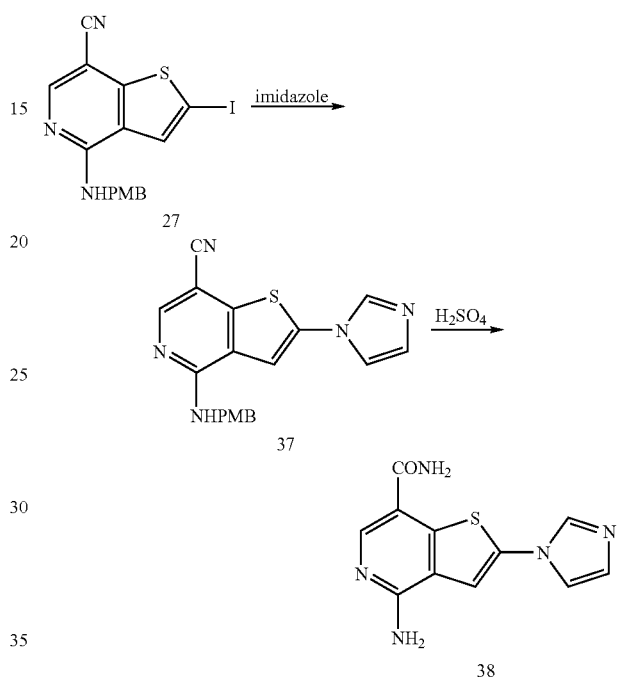

2-Imidazol-1-yl-4-(4-methoxy-benzylamino)-thieno[3,2-c]pyridine-7-carbonitrile (37). To an oven dried Schlenk tube was added CuI (0.0057 g, 0.030 mmol), imidazole (0.097 g, 1.42 mmol), Cs$_2$CO$_3$ (0.405 g, 1.25 mmol). The tube was evacuated and purged to argon 5 times. Under argon, the tube was supplied with 2-iodo-4-(4-methoxy-benzylamino)-thieno[3,2-c]pyridine-7-carbonitrile 27 (0.25 g, 0.59 mmol) trans-1,2-cyclohexanediamine (0.014 mL, 0.12 mmol), and dioxane (1 mL). The reaction contents were briefly evacuated and the vessel purged to argon 3 times, then sealed and brought to 110° C. with stirring. After 24 h, 20 mL of CH$_2$Cl$_2$ were added to the cooled reaction. The mixture was filtered and solvents removed in vacuo. Silica gel column chromatography (eluent: 3% MeOH in CH$_2$Cl$_2$) provided 0.12 g of 37. $^1$H NMR (400 MHz, d$^6$-DMSO) δ 8.57 (t, J=6 Hz, 1H), 8.47 (s, 1H), 8.23 (bs, 1H), 8.00 (s, 1H), 7.71 (bs, 1H), 7.31 (d, J=8 Hz, 2H), 7.21 (bs, 1H), 6.91 (d, J=8 Hz, 2H), 3.74 (s, 3H).

4-Amino-2-imidazol-1-yl-thieno[3,2-c]pyridine-7-carboxylic acid amide (38). To 2-imidazol-1-yl-4-(4-methoxy-benzylamino)-thieno[3,2-c]pyridine-7-carbonitrile 37 (0.050 g, 0.14 mmol) was added H$_2$SO$_4$ (0.25 mL). After stirring at room temperature for 1 h, 2 g of ice were added to the solution. The precipitate was filtered, washed with H$_2$O, then dissolved in 30% methanol, 2.5% triethylamine in CH$_2$Cl$_2$. The solution was concentrated, the solid was suspended in H$_2$O, then filtered and rinsed with H$_2$O resulting in pure 38. $^1$H NMR (400 MHz, d$^6$-DMSO) δ 8.57 (s, 1H), 8.17 (s, 1H), 8.02 (bs, 1H), 7.77 (s, 1H), 7.67 (bs, 1H), 7.39 (bs, 1H), 7.18 (m, 3H).

Example 8

Preparation 4-Amino-2-pyrrolidin-1-yl-thieno[3,2-c]pyridine-7-carboxylic acid amide

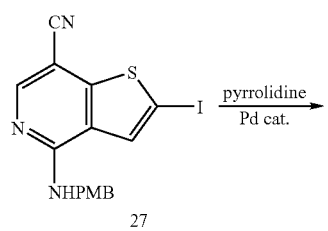

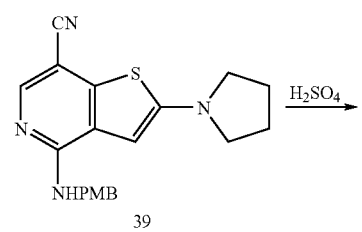

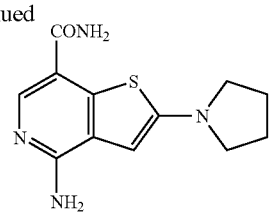

4-Amino-2-pyrrolidin-1-yl-thieno[3,2-c]pyridine-7-carboxylic acid amide (39). To an oven dried, nitrogen flushed flask was added $Pd_2(dba)_3$ (0.011 g, 0.012 mmol), BINAP (0.015 g, 0.024 mmol). Dry THF (2 mL) was added and the mixture stirred at room temperature for 10 min. A solution of 2-iodo-4-(4-methoxy-benzylamino)-thieno[3,2-c]pyridine-7-carbonitrile 27 (0.25 g, 0.59 mmol) in THF (3.5 mL) was added followed by addition of pyrrolidine (0.059 mL, 0.712 mmol) and $Cs_2CO_3$ (0.27 g, 0.83 mmol). The mixture was briefly sparged with nitrogen, then heated at 65° C. for 15 h. The cooled reaction mixture was diluted with $CH_2Cl_2$ (15 mL) and extracted with saturated aqueous $NH_4Cl$. The organics were dried with $Na_2SO_4$ and rapidly flashed through a plug of silica gel (eluent: 5-10% ethyl acetate in toluene). The concentrated crude product was dissolved in $H_2SO_4$ and stirred for 1 h at room temperature. Ice (2 g) was added to the solution and the filtered solution was brought to pH 11 with 50% NaOH. The precipitate was filtered to provide 16 mg of 40. $^1$H NMR (400 MHz, $d^6$-DMSO) δ 8.23 (s, 1H), 7.78 (s, 1H), 7.35 (s, 1H), 6.53 (s, 2H), 6.08 (s, 1H), 3.30 (t, J=6.5 Hz, 4H), 2.03 (p, J=3 Hz, 4H).

Example 9

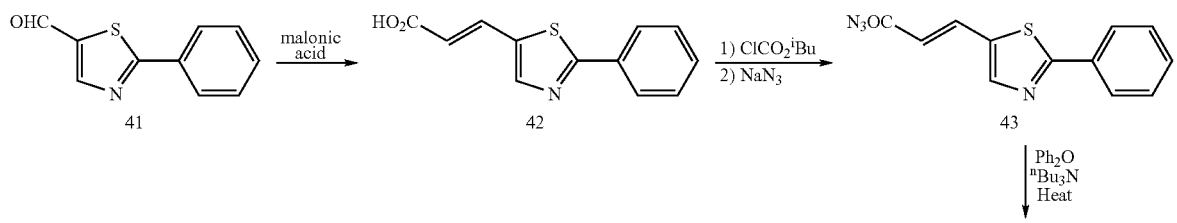

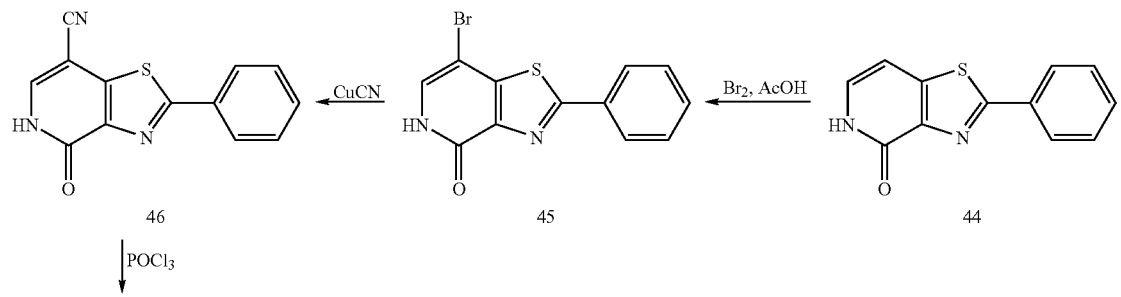

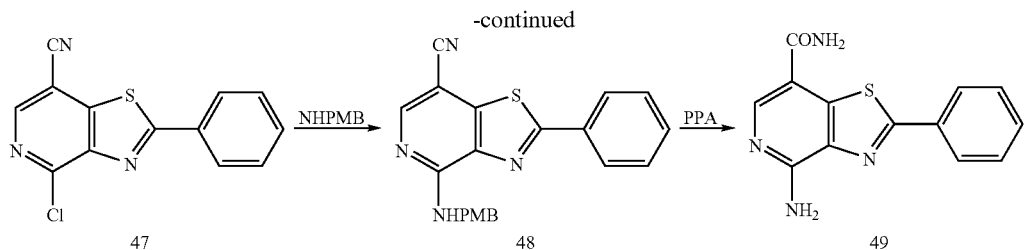

3-(2-Phenyl-thiazolo-5-yl)acrylic acid (42). 2-phenyl-thiazole-5-carbaldehyde 41 (Silberg A. et al. Chem. Ber. 1964, 97, 1684-1687) (3.1 g, 16.4 mmol) was treated with malonic acid (2.4 g, 23.0 mmol), pyridine (3 mL) and piperidine (0.16 mL) and the mixture was heated at reflux for 6 hours before being cooled to room temperature. The mixture was then poured into water (50 mL) with stirring. The resulted yellow solid 42 was filtered, washed with water and air-dried (2.45 g). $^1$H NMR (400 MHz, d$^6$-DMSO) δ: 6.25 (d, J=15.7 Hz, 1H), 7.53 (m, 3H), 7.78 (d, J=15.7 Hz, 1H), 7.97 (m, 2H), 8.23 (s, 1H).

3-(2-Phenyl-thiazolo-5-yl)acryloyl azide (43). To a solution of 3-(2-phenyl-thiazolo-5-yl)acrylic acid 42 (1.75 g, 7.6 mmol) and Et$_3$N (1.40 mL, 9.9 mmol) in acetone (20 mL) at 0° C. was added dropwise ClCO$_2$Bu$^i$ (1.3 mL, 9.9 mmol). After stirring for 1 h at 0° C., NaN$_3$ (643 mg, 9.9 mmol) in water (5 mL) was added and the resulted mixture was stirred at 0° C. for a further 30 min and then at rt for 30 min before the addition of water (100 mL). Filtration gave 43 as a yellow solid, which was washed with water and air-dried (1.85 g). $^1$H NMR (400 MHz, d$^6$-DMSO) δ: 6.40 (d, J=15.6 Hz, 1H), 7.54 (m, 3H), 7.99 (m, 2H), 8.02 (d, J=15.6 Hz, 1H), 8.39 (s, 1H).

2-Phenyl-5H-thiazolo[4,5-c]pyridin-4-one (44). To a stirred mixture of phenyl ether (20 mL) and $^n$Bu$_3$N (5 mL) at 230° C. was added dropwise a solution of 3-(2-phenyl-thiazolo-5-yl)acryloyl azide 43 (1.35 g, 5.26 mmol) in dichloromethane (10 mL). The addition rate was controlled such that the internal temperature remained above 190° C. After addition, the resulting brown solution was stirred for 30 min before being cooled to rt. Hexane (50 mL) was added and the yellow solid was filtered, washed with hexane and dried in the air to afford 44 (0.85 g). $^1$H NMR (400 MHz, d$^6$-DMSO) δ: 6.98 (d, J=6.9 Hz, 1H), 7.37 (d, J=6.9 Hz, 1H), 7.55 (m, 3H), 8.01 (m, 2H), 11.76 (br s, 1H). MS (EI) m/z (M+H$^+$) 229.

7-Bromo-2-phenyl-5H-thiazolo[4,5-c]pyridin-4-one (45). A solution of 2-phenyl-5H-thiazolo[4,5-c]pyridin-4-one 44 (400 mg, 1.75 mmol) in acetic acid (5 mL) at rt was treated with bromine (320 mg, 1.93 mmol) and the resulting mixture was heated at reflux for 30 min. After cooling to rt, water (20 mL) was added to the mixture. The yellow solid which formed was filtered, washed with water and dried in the air to afford 45 (527 mg). $^1$H NMR (400 MHz, d$^6$-DMSO) δ: 7.57 (m, 3H), 7.70 (s, 1H), 8.05 (m, 2H), MS (EI) m/z (M+H$^+$) 308.

4-Chloro-2-phenyl-thiazolo[4,5-c]pyridine-7-carbonitrile (47). A mixture of 7-bromo-2-phenyl-5H-thiazolo[4,5-c]pyridin-4-one 5 (515 mg, 1.68 mmol) and CuCN (331 mg, 3.70 mmol) in DMF was heated at reflux for 10 hours before cooling to rt. A solution of FeCl$_3$ (3.32 g, 20 mmol) in concentrated HCl (0.9 mL) and water (5.2 mL) was then added to decompose the copper complex. The mixture was stirred at 70° C. for 15 min and then allowed to cool to rt. Water (35 mL) was added and a yellow solid 6 was formed which was filtered, washed with water and dried in the air (380 mg). 4-oxo-2-phenyl-4,5-dihydro-thiazolo[4,5-c]pyridine-7-carbonitrile 46 was treated with POCl$_3$ (5 mL) and the mixture heated at reflux for 4 hours. The solvent was removed under reduced pressure and the residue was partitioned between dichloromethane and aqueous sodium bicarbonate solution. The organics were separated and dried over sodium sulfate. Removal of solvent followed by silica gel column chromatography (eluent: dichloromethane) gave white solid 47 (255 mg). $^1$H NMR (400 MHz, d$^6$-DMSO) δ: 7.61 (m, 3H), 8.21 (m, 2H), 8.93 (s, 1H). MS (EI) m/z (M+H$^+$) 272.

4-(4-Methoxy-benzylamino)-2-phenyl-thiazolo[4,5-c]pyridine-7-carbonitrile (48). A mixture of 4-chloro-2-phenyl-thiazolo[4,5-c]pyridine-7-carbonitrile 47 (54.2 mg, 0.2 mmol) and potassium carbonate (66 mg, 0.48 mmol) in NMP (1 mL) was treated with 4-methoxybenzylamine (32.5 µL, 2.4 mmol) and the mixture stirred at 130° C. for 8 hours. Silica gel column chromatography (eluent: dichloromethane and ethyl acetate (10 to 1)) afforded 48 as a pale yellow solid (70 mg). $^1$H NMR (400 MHz, d$^6$-DMSO) δ: 3.71 (s, 3H), 4.72 (d, J=5.9 Hz, 2H), 6.87 (d, J=8.4 Hz, 2H), 7.31 (d, J=8.4 Hz, 2H), 7.60 (m, 3H), 8.15 (m, 2H), 8.47 (s, 1H), 8.84 (t, J=6.1 Hz, 1H). MS (EI) m/z (M+H$^+$) 373.

7-Carboxamido-4-amino-2-phenyl-thiazolo[4,5-c]pyridine (49). 4-(4-methoxy-benzylamino)-2-phenyl-thiazolo[4,5-c]pyridine-7-carbonitrile 48 (70 mg, 0.19 mmol) was treated with polyphosphoric acid (2 mL) and the mixture was heated at 110° C. for 2 hours. After cooling to rt, water (10 mL) was added and the resulting solid was filtered. The filtrate was neutralized with 4M NaOH solution. The white solid formed was filtered, washed with water and dried in the air affording 49 (46 mg). $^1$H NMR (400 MHz, d$^6$-DMSO) δ: 7.30 (s, 2H), 7.42 (br s, 1H), 7.56 (m, 3H), 8.04 (br s, 1H), 8.14 (m, 2H), 8.59 (s, 1H). MS (EI) m/z (M+H$^+$) 271.

Example 10

Preparation of 7-amino-2-phenyl-thieno[2,3-c]pyridine-4-carboxylic acid amide

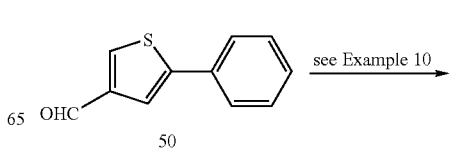

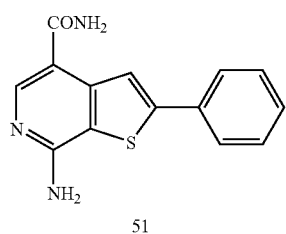

7-Amino-2-phenyl-thieno[2,3-c]pyridine-4-carboxylic acid amide (51). 51 was synthesized from 5-phenyl-thiophene-3-carbaldehyde 50 (Gjoes et al. Acta Chem Scand 1972, 26, 1851-1858) in a similar manner to the procedure used in Example 9. $^1$H NMR (400 MHz, d$^6$-DMSO) δ: 7.04 (s, 2H), 7.08 (br s, 1H), 7.45 (m, 1H), 7.53 (m, 2H), 7.78 (m, 3H), 8.34 (s, 1H), 8.37 (s, 1H). MS (EI) m/z (M+H$^+$) 270.

Example 11

Preparation of 4-amino-3-methyl-2-phenyl-thieno[3,2-c]pyridine-7-carboxylic acid amide

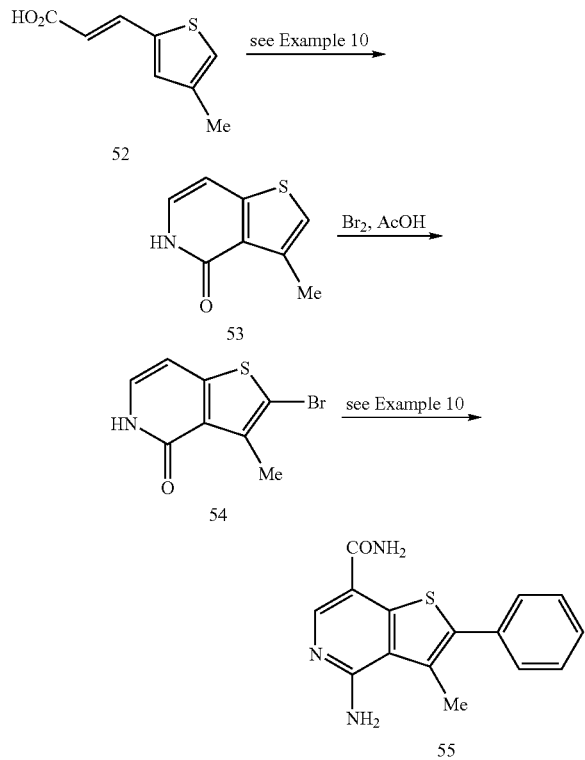

3-Methyl-5H-thieno[3,2-c]pyridin-4-one (53). 53 was prepared from 3-(4-methyl-thiophen-2-yl)-acrylic acid 52 (Poirier Y. et al. Bull. Soc. Chim. Fr., 1966, 1052-1068) in a similar manner to that described in Example 9. $^1$H NMR (400 MHz, d$^6$-DMSO) δ: 2.68 (d, J=1.1 Hz, 3H), 6.69 (d, J=7.0 Hz, 1H), 6.87 (d, J=1.1 Hz, 1H), 7.13 (d, J=7.0 Hz, 1H), 10.75 (br s, 1H). MS (EI) m/z (M+H$^+$) 166.

4-Amino-3-methyl-2-phenyl-thieno[3,2-c]pyridine-7-carboxylic acid amide (54). A solution of 3-methyl-5H-thieno[3,2-c]pyridin-4-one 53 (1.45 g, 8.8 mmol) in acetic acid (25 mL) was treated with bromine (0.5 mL, 9.7 mmol). The mixture was then stirred at 100° C. for 30 min. After cooling to rt, water (50 mL) was added. Filtration gave 2-bromo-3-methyl-5H-thieno[3,2-c]pyridin-4-one 54 as a yellow solid containing approx. 28% of a dibromide species. The crude material was converted to 55 using the procedure described in Example 9. $^1$H NMR (400 MHz, d$^6$-DMSO) δ: 2.56 (s, 3H), 6.64 (s, 2H), 7.25 (br s, 1H), 7.50 (m, 5H), 7.85 (br s, 1H), 8.50 (s, 1H). MS (EI) m/z (M+H$^+$) 284.

Example 12

Preparation of 4-amino-2(1H-pyrazol-4-yl)thieno[3,2-c]pyridine-7-carboxylic acid amide

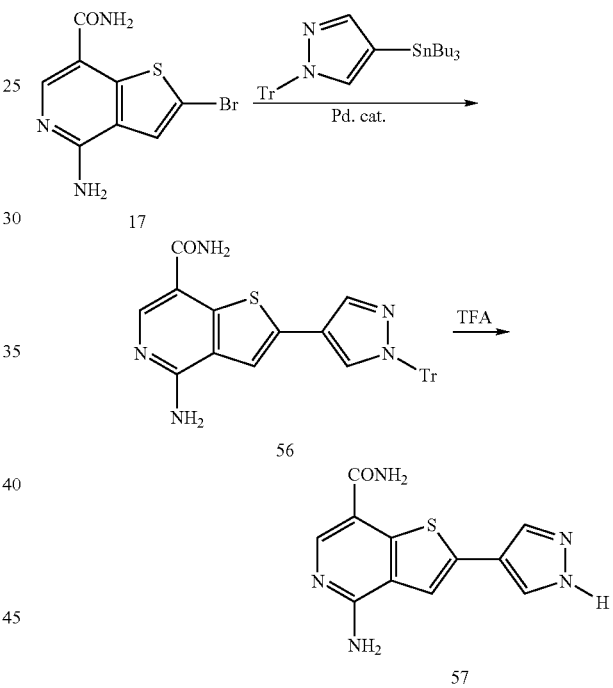

4-Amino-2(1H-pyrazol-4-yl)thieno[3,2-c]pyridine-7-carboxylic acid amide (57). A mixture of 4-amino-2-bromo-thieno[3,2-c]pyridine-7-carboxylic acid amide 17 (100 mg, 0.37 mmol), 4-tributylstannyl-1-triphenylmethylpyrazole (380 mg, 0.56 mmol) and tetrakis(triphenylphosphine)palladium(0) (50 mg, 0.043 mmol) in dioxane (3 mL) by with column chromatography on silica gel (eluent: DCM/MeOH, 20/1 to 10/1) gave 56 as a white solid (60 mg). 56 was treated with 50% TFA in dichloromethane (2 mL) for 2 hours at rt. The solvent was then removed under reduced pressure and the residue was partitioned between dichloromethane and sodium bicarbonate solution. The organics were dried and removed. Silica gel column chromatography (eluent: DCM/MeOH, 20/1 to 5/1) gave 57 as a white solid (20 mg). $^1$H NMR (400 MHz, d$^6$-DMSO) δ: 6.97 (s, 1H), 7.10 (s, 1H), 7.22 (s, 1H), 7.30 (br s, 2H), 7.72 (s, 1H), 7.81 (br s, 1H), 8.15 (br s, 1H), 8.42 (s, 1H). MS (EI) m/z (M+H$^+$) 260.

Example 13

Preparation of 4-Amino-2-[4-(2-cyanoethyl)-5-methylthiophen-2-yl]-thieno[3,2-c]pyridine-7-carboxylic acid amide

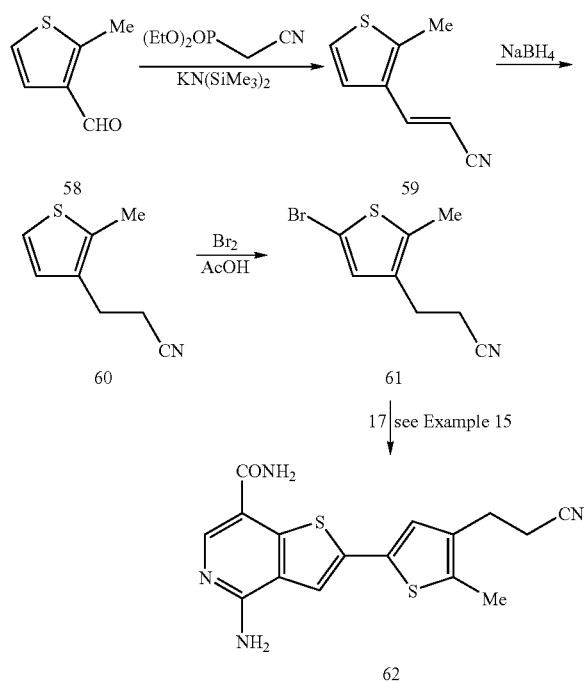

3-(2-Methylthiophen-3-yl)-acylonitrile (59). To a solution of diethyl(cyanomethyl)phosphonate (1.26 mL, 7.8 mmol) in THF (20 mL) at 0° C. was added dropwise a 0.5 M solution of KN(SiMe$_3$)$_2$ in toluene (13.2 mL, 6.6 mmol). After 30 min, the resulting solution was added dropwise to a solution of 2-methyl-3-thiophenecarbaldehyde 58 (Comins D L et al. *J. Org. Chem.*, 1987, 52, 104-109) (756 mg, 6 mmol) in THF (20 mL) at 0° C. The mixture was then stirred at rt for 30 min before being quenched with saturated aqueous ammonium chloride solution. The organics were separated and the water layer was extracted with EtOAc (2×10 mL). The combined organics were washed with brine and dried over MgSO$_4$. Removal of the solvent followed with silica gel column chromatography (eluent: DCM/hexane, 1/1) gave 59 as a white solid (795 mg).

3-(2-Methylthiophen-3-yl)-propionitrile (60). A solution of 3-(2-methylthiophen-3-yl)-acylonitrile 59 (410 mg, 2.8 mmol) in pyridine (4 mL) and EtOH (1 mL) was treated with sodium borohydride (104 mg, 11 mmol) at rt and then the mixture was heated to 100° C. for 4 hours. After cooling to rt, water was added and the mixture was extracted with EtOAc (2×20 mL). The combined organics were washed with water and dried over MgSO$_4$. Removal of the solvent followed with silica gel column chromatography (eluent: DCM/hexane, 1/1) gave 60 as a colorless liquid (370 mg).

3-(5-Bromo-2-methyl-thiophen-3-yl)-propionitrile (61). A solution of 3-(2-methylthiophen-3-yl)-propionitrile 60 (320 mg, 2.1 mmol) in acetic acid (5 mL) was treated with bromine (0.12 mL, 2.3 mmol) and the mixture stirred at rt for 1 hour. Water was added and the mixture was extracted with EtOAc (2×20 mL). The combined organics were washed with water and dried over MgSO$_4$. Removal of the solvent followed with silica gel column chromatography (eluent: DCM/hexane, 1/1) gave 61 as a colorless liquid (330 mg).
$^1$H NMR (400 MHz, CDCl$_3$) δ: 2.35 (s, 3H), 2.53 (t, J=10.5 Hz, 2H), 2.84 (t, J=10.5 Hz, 2H) 6.80 (s, 1H).

4-Amino-2-[4-(2-cyanoethyl)-5-methylthiophen-2-yl]-thieno[3,2-c]pyridine-7-carboxylic acid amide (62). 62 was prepared from 4-amino-2-bromo-thieno[3,2-c]pyridine-7-carboxylic acid amide 17 and 3-(5-bromo-2-methyl-thiophen-3-yl)-propionitrile 61 as a white solid in a similar manner to the procedure described in Example 14. $^1$H NMR (400 MHz, d$^6$-DMSO) δ: 2.40 (s, 3H), 2.81 (s, 4H), 7.15 (s, 2H), 7.23 (s, 1H), 7.24 (br s, 1H), 7.70 (s, 1H), 7.80 (br s, 1H), 8.46 (s, 1H). MS (EI) m/z (M+H$^+$) 343.

Example 14

Preparation of 4-amino-2-morpholin-4-ylmethyl-thieno[3,2-c]pyridine-7-carboxylic acid amide

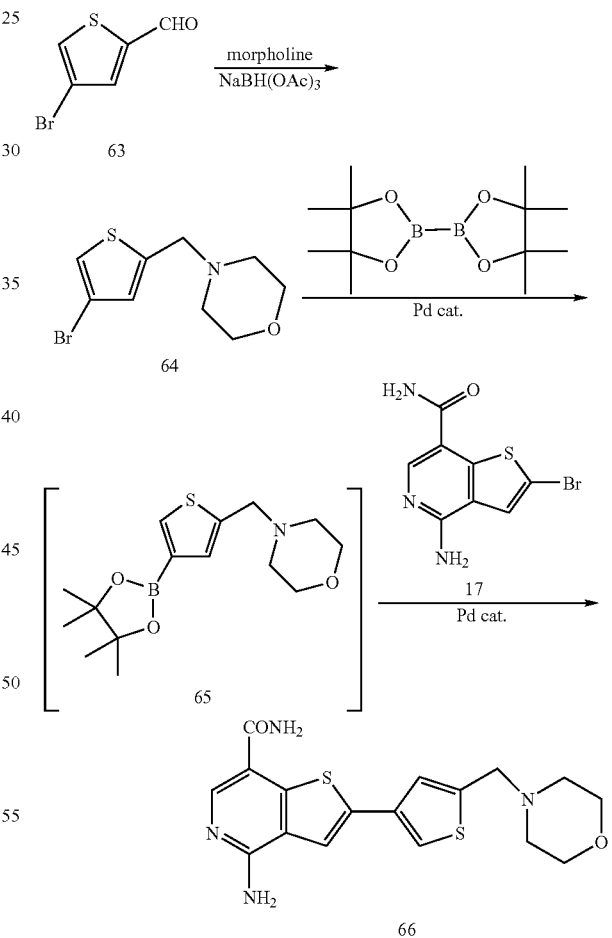

4-(4-Bromo-thiophen-2-ylmethyl)-morpholine (64). To a solution of 4-bromothiophene-2-carbaldehyde 63 (Avocado, UK) (1.20 g, 6.3 mmol) in THF (50 mL) at rt was added dropwise morpholine (0.96 g, 11 mmol). After the reaction was stirred at rt for 5 minutes, NaBH(OAc)$_3$ (3.18 g, 15 mmol) was added in one portion. The resulting mixture was stirred at rt for 3 h. Ethyl acetate (80 mL) was added and then washed with NaHCO₃ (20 mL×2) and brine (20 mL). The organic layer was dried with MgSO₄. After the solvent was evaporated, the residue was purified by silica gel column chromatography to give 64 (1.31 g).

¹H NMR (400 MHz, CDCl₃) δ, 2.50-2.52 (m, 4H), 2.67 (s, 2H), 3.72-3.75 (m, 4H), 6.87 (s, 1H), 7.15 (d, J=1.4 Hz, 1H). MS (EI) m/z (M+H⁺) 263.

4-Amino-2-morpholin-4-ylmethyl-thieno[3,2-c]pyridine-7-carboxylic acid amide (66). To a mixture of 4-(4-bromo-thiophen-2-ylmethyl)-morpholine 64 (173 mg, 0.66 mmol), bis(pinacolato)diboron (352 mg, 1.39 mmol.), Pd(PPh₃)₄ (76 mg, 0.07 mmol) and KOAc (194 mg, 2.0 mmol) was added degassed DMF (5 mL). The reaction mixture was heated at 120° C. under N₂ for 2 h and then cooled down to room temperature. A solution of 4-amino-2-bromo-thieno[3,2-c]pyridine-7-carboxylic acid amide 17 (150 mg, 0.55 mmol), Pd(PPh₃)₄ (69 mg, 0.06 mmol) and Na₂CO₃ (1.0 mL of a 2M aqueous solution, 3.3 mmol) in DMF (2.0 mL) was added. The resulting mixture was heated at 90 ⁰ C for 1.5 h. The solvent was then removed via vacuum, the residue was dissolved in DMSO (4.0 mL) and the mixture purified by reverse phase preparative HPLC to give 66 (134 mg). ¹H NMR (400 MHz, CDCl₃) δ, 3.12 (m, 2H), 3.32 (m, 2H), 3.82 (m, 2H), 3.95 (m, 2H), 4.62 (s, 2H), 7.75 (s, 1H), 7.81 (br, 1H), 8.09 (s, 1H), 8.34 (s, 1H), 8.38 (br, 1H), 8.56 (s, 1H), 9.19 (br, 1H), 11.73 (br, 1H). MS (EI) m/z (M+H⁺) 375.

Example 15

Preparation of 4-Amino-2-(2,2-dioxo-2,3,3a,7a-tetrahydro-1H-2λ⁶-benzo[c]thiophen-5-yl)-thieno[3,2-c]pyridine-7-carboxylic acid amide

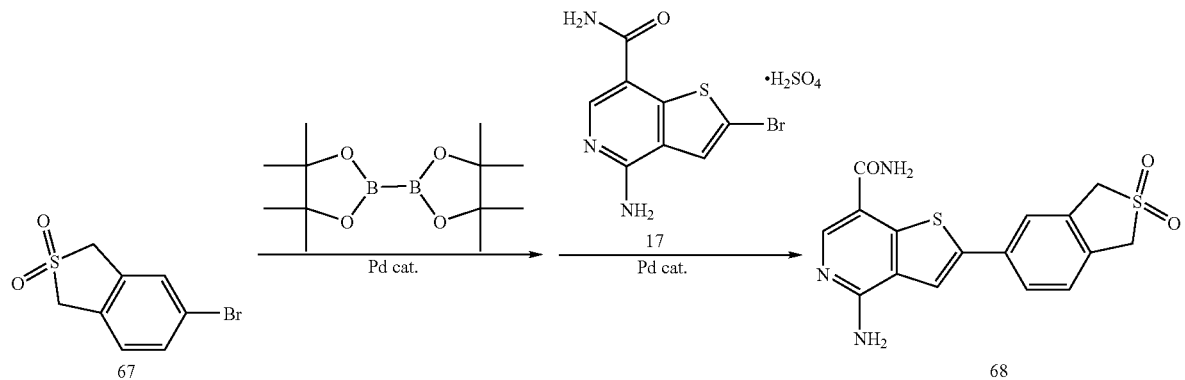

4-Amino-2-(2,2-dioxo-2,3,3a,7a-tetrahydro-1H-2λ⁶-benzo[c]thiophen-5-yl)-thieno[3,2-c]pyridine-7-carboxylic acid amide (68). To a stirred solution 5-bromo-1,3-dihydro-benzo[c]thiophene 2,2-dioxide (160 mg, 0.65 mmol) 67 (Salor, Milwaukee, Wis.) in DMSO (1 mL) was added bis(pinacolato)diboron (178 mg, 0.70 mmol), KOAc (159 mg, 1.6 mmol) and Pd(dppf)Cl₂ DCM complex (22 mg, 0.027 mmol). The mixture was degassed with N₂ and heated at 85° C. for 2 h then DMSO (2 mL), H₂O (0.5 mL), K₂CO₃ (223 mg, 1.6 mmol) and 4-amino-2-bromo-thieno[3,2-c]pyridine-7-carboxylic acid amide H₂SO₄ salt 17 (200 mg, 0.54 mmol) were added. The mixture was stirred at 85° C. for a further 12 h then filtered. The residue was washed with DMSO (2 mL) and the filtrate purified by reverse phase preparative HPLC to yield 68 as a white solid. ¹H-NMR (400 MHz, d⁶-DMSO) δ 8.31 (s, 1H), 8.24 (s, 1H), 8,19 (bs, 1H), 7.97-7.92 (m, 3H), 7.85 (d, 1H), 4.78 (s, 2H), 4.71 (s, 2H).

Example 16

Preparation of 4-amino-2-{4-cyanomethyl-2-[2-(1-methyl-pyrrolidine-2-yl)-ethoxy]-phenyl}-thieno[3,2-c]pyridine-7-carboxylic acid amide

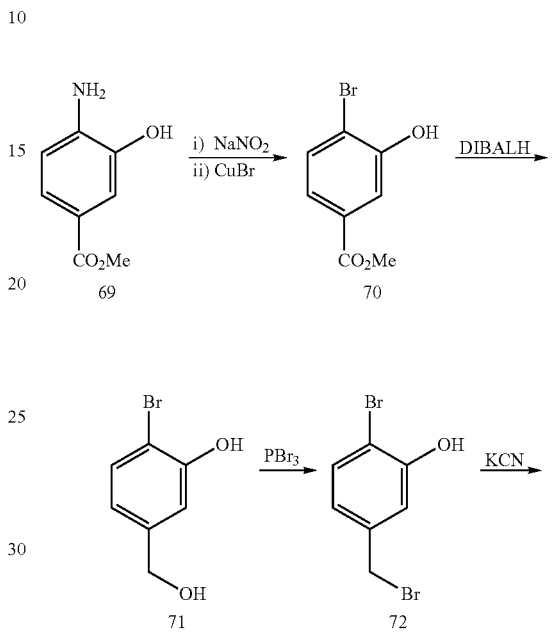

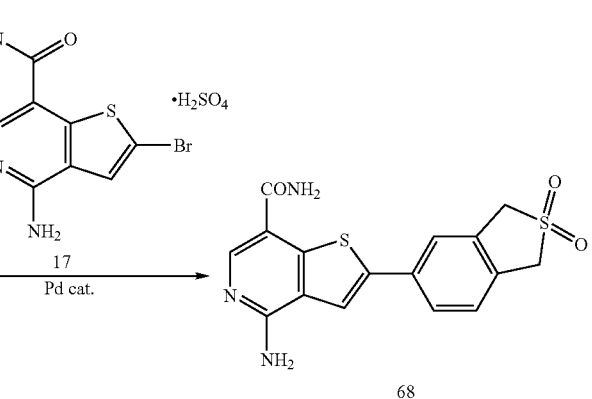

-continued

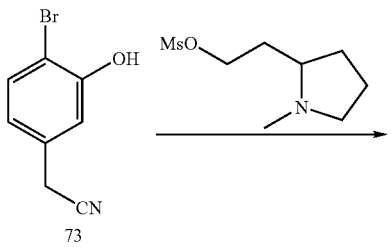

-continued

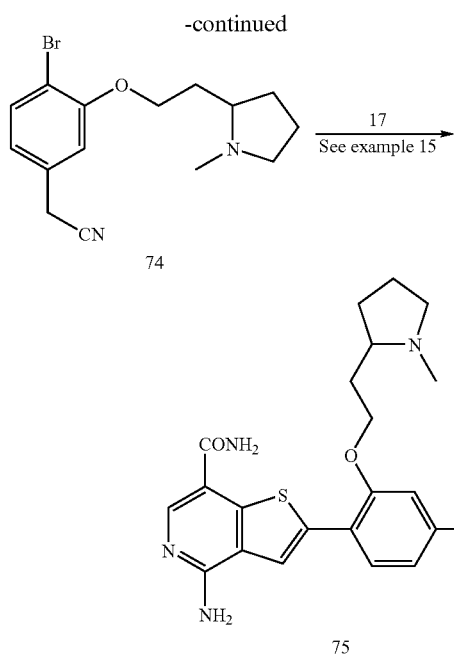

4-Bromo-3-hydroxybenzoic acid methyl ester (70). To a suspension of methyl 4-amino-3-hydroxybenzoate 69 (21.7 g, 127 mmol) in water (115 mL) at 0° C. was added a solution of sodium nitrite (9.1 g, 127 mmol) in water (50 mL). The resultant mixture was stirred at 0° C. for 1 h. Meanwhile, copper sulfate pentahydrate (42.4 g, 169 mmol) was dissolved in water (135 mL) with heating and sodium bromide (26.4 g, 257 mmol) was added slowly with stirring. The resultant dark green solution was stirred for 5 min, and then was treated with a solution of sodium sulfite (11.3 g, 90 mmol) in water (40 mL). The resultant lime green slurry was stirred for 5 min, and then cooled by the addition of ice. The ice water was decanted off, carefully avoiding dryness. The residue was rinsed with water (3×) and the resultant white solid was dissolved in 115 mL concentrated HBr (115 mL). This acidic copper bromide solution was added to the diazonium salt suspension (see above) at 0° C. The resultant mixture was gradually heated up to 100° C., then stirred at this temperature for 1 h. Significant foaming was observed. After this time, the reaction mixture was cooled and brought to pH 4-5 by the addition of sodium carbonate. EtOAc was added and the mixture was filtered. The filtrate was extracted with EtOAc (3×). The organic layers were dried over $Na_2SO_4$ and filtered to give 70. $^1$H NMR (400 MHz CDCl$_3$) δ: 3.91 (s, 3H), 5.81 (br s, 1H), 7.48 (dd, J=8.5 Hz, 1.4 Hz, 1H), 7.54 (d, J=8.5 Hz, 1H), 7.68 (s, 1H). MS (EI) m/z (M−H⁻) 229.

2-Bromo-5-hydroxymethylphenol (71). To a suspension of 4-bromo-3-hydroxybenzoic acid methyl ester 70 (6.97 g, 30.2 mmol) in dichloromethane (360 mL) at 0° C. was added DIBALH (100 mL of a 1 M in toluene, 100 mmol) portionwise. Significant gas evolution was observed. The resultant mixture was warmed to room temperature and stirred for 2.75 h. After this time, the reaction mixture was quenched by the addition of saturated aqueous sodium potassium tartrate (600 mL) and saturated aqueous ammonium chloride (100 mL). The resultant biphasic mixture was stirred vigorously for 2 h, and then extracted with dichloromethane (3×). The organic layers were dried over $Na_2SO_4$ and filtered, to give 71. $^1$H NMR (400 MHz CDCl$_3$) δ: 1.70 (br s, 1H), 4.64 (d, J=4.5 Hz, 2H), 5.55 (br s, 1H), 6.82 (dd, J=8.0 Hz, 2.0 Hz, 1H), 7.04 (d, J=2.0 Hz, 1H), 7.44 (d, J=8.0 Hz, 1H). MS (EI) m/z (M−H⁻) 201.

2-Bromo-5-bromomethylphenol (72). To a suspension of 2-bromo-5-hydroxymethylphenol 71 (5.17 g, 25.5 mmol) in chloroform (100 mL) at 0° C. was added a solution of PBr$_3$ (1.21 g 12.7 mmol) in chloroform (60 mL) over 30 min. The resultant solution was stirred at 0° C. for 1 h, and then was warmed to room temperature and stirred for an additional 1.75 h. After this time, the reaction mixture was poured into ice water and extracted with dichloromethane (2×). The organic layers were dried over $Na_2SO_4$, filtered, and the filtrate was purified by silica gel chromatography (eluent: dichloromethane:EtOAc, 95:5) to give 72. $^1$H NMR (400 MHz CDCl$_3$) δ: 4.40 (s, 2H), 5.52 (s, 1H), 6.85 (dd, J=8.2 Hz, 2.1 Hz, 1H), 7.06 (d, J=2.1 Hz, 1H), 7.43 (d, J=8.2 Hz, 1H). MS (EI) m/z (M−H⁻) 263.

{4-Bromo-3-[2-(1-methyl-pyrrolidine-2-yl)-ethoxy]-phenyl}-acetonitrile (74). A suspension of KCN (16.0 g, 238.3 mmol) in DMF (100 mL) was heated at 60° C. for 30 min. The slurry was cooled to room temperature and treated with a solution of 2-bromo-5-bromomethylphenol 72 (4.16 g, 15.7 mmol) in DMF (50 mL). The resultant mixture stirred at room temperature for 23 h, and then was diluted with water and extracted with ethyl acetate (5×). The organic layers were dried over $Na_2SO_4$, filtered, and the filtrate was purified by chromatography on silica gel (hexanes:EtOAc, 3:1) to afford impure (4-bromo-3-hydroxy-phenyl)acetonitrile 73. To a solution of KOH (26.5 mg) in MEOH (1.5 mL) was added (4-bromo-3-hydroxy-phenyl)-acetonitrile 73 (100.0 mg), the resulting mixture was stirred at room temperature for 10 min then conentrated in vacuo. DMSO (3 mL) and methanesulfonic acid 2-(1-methyl-pyrrolidin-2-yl)-ethyl ester, (prepared from 2-(1-methyl-pyrrolidin-2-yl)-ethanol, methane sulfonyl chloride in presence of triethylamine) were added. The reaction mixture was stirred at room temperature overnight. DCM (80 mL) was added and the organics washed with saturated aqueous NaHCO$_3$ solution (20 mL) and brine (20 mL). The organic layer was dried with MgSO$_4$. The residue was purified by silica gel column chromatography (eluent: DCM/MeOH, 4/1) to give 74. MS (EI) m/z (M+H⁺) 324.

4-Amino-2-{4-cyanomethyl-2-[2-(1-methyl-pyrrolidine-2-yl)-ethoxy]-phenyl}-thieno[3,2-c]pyridine-7-carboxylic acid amide (75). 75 was prepared from 74 and 4-amino-2-bromo-thieno[3,2-c]pyridine-7-carboxylic acid amide 17 in a similar manner to that described for Example 14. MS (EI) m/z (M+H⁺) 436.

Example 17

Preparation of 4-amino-2-[5-(2-cyano-ethyl)-thiophen-3-yl]-thieno[3,2-c]pyridine-7-carboxylic acid amide

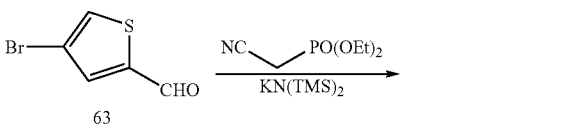

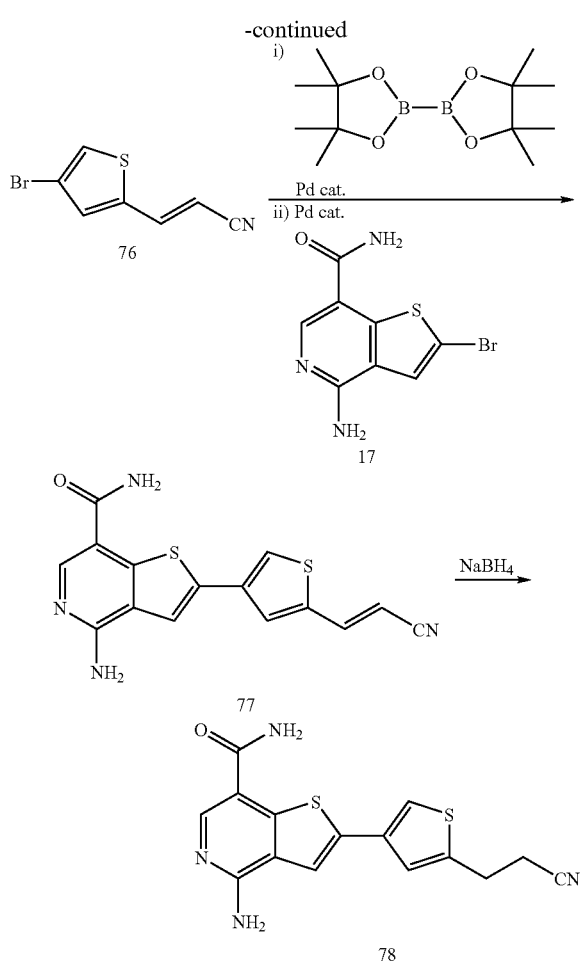

(3.6 mL), and Pd(PPh$_3$)$_4$ (0.12 g, 0.11 mmol) were added. The reaction mixture was then heated at 100° C. under nitrogen until completion of the reaction (approx. 1 h), cooled to room temperature and concentrated in vacuo to approx. half volume. The mixture was diluted with water (20 mL) and the precipitate of 77 that formed was collected by filtration, washed with MeOH, and dried. 4-amino-2-[5-(cyano-vinyl)-thiophen-3-yl]-thieno[3,2-c]pyridine-7-carboxylic acid amide 77 was then dissolved in pyridine (5 mL) and EtOH (1 mL). To the resulting solution was added NaBH$_4$ (0.16 g, 4.1 mmol). The solution was then heated at 100° C. until completion of the reaction (approx. 2 h) and then concentrated in vacuo. The crude product was purified by silica gel column chromatography (eluent: 80% of CH$_2$Cl$_2$:MeOH:NH$_4$OH (89:9:1) in CH$_2$Cl$_2$). The major fractions were combined and concentrated to give 78 (0.12 g) as a pale-yellow solid. $^1$H NMR (400 MHz, d$^6$-DMSO) δ: 8.48 (s, 1H), 7.90 (br.s, 1H), 7.86 (s, 1H), 7.65 (d, J=1.4 Hz, 1H), 7.31 (s, 1H), 7.26 (br s, 1H), 7.12 (s, 2H), 3.17 (t, 2H), 2.92 (t, 2H). MS (EI) m/z (M+H$^+$) 329 and (M+Na$^+$) 351.

Example 18

Preparation of 4-amino-2[4-(2-cyano-ethyl)-5-(3-hydroxy-propyl)-thiophen-2-yl]-thieno[3,2-c]pyridine-7-carboxylic acid amide

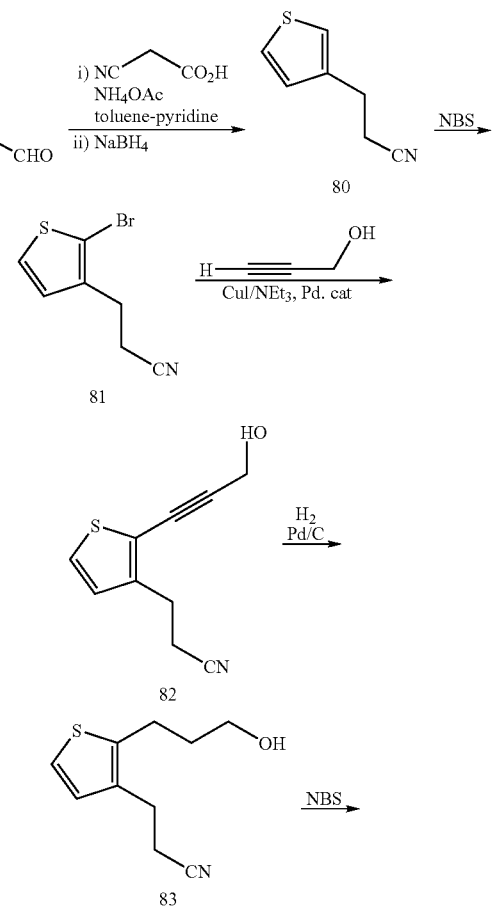

3-(4-Bromo-thiophen-2-yl)-acrylonitrile (76). A solution of diethyl(cyanomethyl)phosphonate (2.1 mL, 12.9 mmol) in anhydrous THF (50 mL) was cooled to 0° C. under nitrogen and treated with KN(TMS)$_2$ (11 mmol of a 0.5 M solution in toluene). After stirring for 15 min at 0° C., a solution of 4-bromo-2-thiophenecarboxaldehyde 63 (Aldrich, Wis.) (1.9 g, 10 mmol) in anhydrous THF (50 mL) was added and the resulting mixture was stirred for 30 min at 0° C. Saturated aqueous NH$_4$Cl solution was added and the crude product extracted three times with diethylether. The ether extracts were dried over Na$_2$SO$_4$, filtered, and evaporated, and the product was purified by flash chromatography on a silica gel column (eluent: 5% EtOAc in hexane). The major fractions were combined and concentrated to give 76 (2.1 g) in 9.3 to 1 ratio of trans to cis isomers as a white solid; For trans isomer: $^1$H NMR (400 MHz, d$^6$-DMSO) δ: 7.90 (s, 1H), 7.77 (d, J=16.5 Hz, 1H), 7.57 (s, 1H), 6.28 (d, J=16.5 Hz, 1H); For cis isomer: $^1$H NMR (400 MHz, d$^6$-DMSO) δ 7.97 (s, 1H), 7.65 (s, 1H), 7.57 (d, J=11.1 Hz, 1H), 5.82 (d, J=11.7 Hz, 1H). MS (EI) m/z [(M+H$^+$) ($^{79}$Br)] 214 and [(M+H$^+$) ($^{81}$Br)] 216.

4-Amino-2-[5-(2-cyano-ethyl)-thiophen-3-yl]-thieno[3,2-c]pyridine-7-carboxylic acid amide (78). A mixture of 3-(4-bromo-thiophen-2-yl)-acrylonitrile 76 (0.33 g, 1.55 mmol), potassium acetate (0.47 g, 4.74 mmol), bis(pinacolato)diboron (0.84 g, 3.3 mmol), Pd(PPh$_3$)$_4$ (0.12 g, 0.1 mmol), and DMF (11 mL) was heated at 100° C. under nitrogen for 1 h. 4-Amino-2-bromo-thieno[3,2-c]pyridine-7-carboxylic acid amide 17 (0.28 g, 1.0 mmol), 2 M aqueous Na$_2$CO$_3$ solution

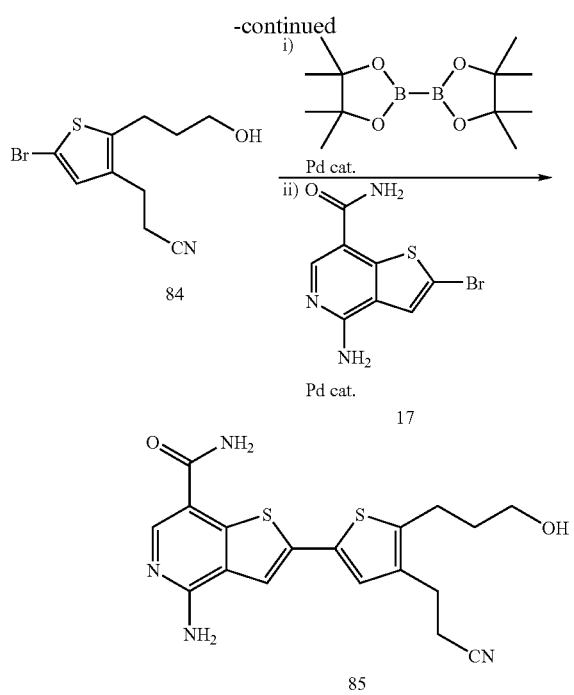

3-Thiophen-3-yl-propionitrile (80). A mixture of cyanoacetic acid (7.56 g, 88.9 mmol), thiophene-3-carbaldehyde 79 (Aldrich, Wis.) (10.97 g, 97.8 mmol), ammonium acetate (0.36 g, 4.7 mmol), toluene (89 mL), and pyridine (47 mL) was heated at reflux for 20 h in a flask fitted with a Dean-Stark trap and condenser. After evaporation of solvents, a solution of the residue in $CH_2Cl_2$ (300 mL) was washed with water, dried over $Na_2SO_4$, filtered, and evaporated. The crude product was isolated by flash chromatography on a silica gel column using 10% to 20% gradient of EtOAc in hexane as eluent to afford 3-thiophen-3-yl acrylonitrile (6.38 g) in a 1.8 to 1 ratio of trans to cis isomer as a dark brown oil. The product was then dissolved in pyridine (100 mL) and EtOH (20 mL). To the resulting solution was added $NaBH_4$ (3.57 g, 94.4 mmol). The solution was then heated at 100° C. until completion of the reaction approx. (4 h) and concentrated in vacuo. The crude product was purified by silica gel column chromatography (eluent: 11% EtOAc in hexane). The major fractions were combined and concentrated to give 80 (4.03 g) as a yellow liquid. $^1$H NMR (400 MHz, d$^6$-DMSO) δ: 7.50 (dd, J=3.0 and 5.0 Hz, 1H), 7.31 (m, 1H), 7.07 (dd, J=1.0 and 5.0 Hz, 1H), 2.89 (m, 2H), 2.81 (m, 2H). MS (EI) m/z (M+H$^+$) 138.

3-(2-Bromo-3-yl)-propionitrile (81). To a solution of 3-thiophen-3-yl-propionitrile 80 (4.01 g, 29.2 mmol) in DMF (20 mL) was added NBS (5.72 g, 32.2 mmol). The mixture was then stirred at room temperature until completion of the reaction (approx. 2 h) and concentrated in vacuo. A solution of the residue in EtOAc (200 mL) was washed with water, dried over $Na_2SO_4$, filtered, and concentrated in vacuo. The crude product was purified by silica gel column chromatography (eluent: 11% to 17% gradient of EtOAc in hexane). The major fractions were combined and concentrated to give 81 (5.48 g) as a yellow liquid. $^1$H NMR (400 MHz, d$^6$-DMSO) δ: 7.60 (d, J=5.63 Hz, 1H), 7.06 (d, J=5.64 Hz, 1H), 2.82 (m, 4H). MS (EI) m/z [(M+H$^+$) ($^{79}$Br)] 215.9 and [(M+H$^+$) ($^{81}$Br)] 218.

3-[2-(3-Hydroxy-prop-1-ynyl)-thiophen-3-yl]-propionitrile (82). To a stirred solution of 3-(2-bromo-thiophen-3-yl)-propionitrile 81 (0.5 g, 2.31 mmol), CuI (0.04 g, 0.23 mmol), $PdCl_2(PPh_3)_2$ (0.08 g, 0.12 mmol) in $NEt_3$ (6 mL) at room temperature was added propargyl alcohol (0.28 mL, 4.62 mmole) and the reaction mixture was stirred at 50° C. for 9 h. The mixture was concentrated in vacuo and purified by silica gel column chromatography (eluent: 50% EtOAc in hexane). The major fractions were combined and concentrated to give 82 (0.27 g) as a yellow syrup. $^1$H NMR (400 MHz, d$^6$-DMSO) δ: 7.54 (d, J=5.0 Hz, 1H), 7.10 (d, J=5.0 Hz, 1H), 5.37 (t, J=6.0 Hz, 1H), 4.34 (d, J=6.0 Hz, 2H), 2.93 (t, J=7.0 Hz, 2H), 2.84 (t, J=7.0 Hz, 2H). MS (EI) m/z (M−OH$^+$) 174.

3-[2-(3-Hydroxy-propyl)-thiophen-3-yl]-propionitrile (83). To a stirred solution of 3-[2-(3-hydroxy-prop-1-ynyl)-thiophen-3-yl]-propionitrile 82 (0.27 g, 1.39 mmol) was dissolved in MeOH (5 mL). To this solution was added Pd/C [10% w/w] (0.15 g, 0.14 mmol). The mixture was then stirred under an atmosphere of hydrogen at room temperature for 4 h then filtered through a Celite pad and concentrated in vacuo. Purification by silica gel column chromatography (eluent: 50% EtOAc in hexane) afforded 83 (0.18 g) as a colorless syrup. $^1$H NMR (400 MHz, d$^6$-DMSO) δ: 7.27 (d, J=5.0 Hz, 1H), 6.94 (d, J=5.0 Hz, 1H), 4.51 (t, J=5.0 Hz 1H), 3.42 (dd, J=6.0 Hz and 11.5 Hz, 2H), 2.82-2.71 (m, 6H), 1.70 (m, 2H). MS (EI) m/z (M+H$^+$) 196, (M−OH$^+$) 178.

3-[5-Bromo-2-(3-hydroxy-propyl)-thiophen-3-yl]-propionitrile (84). To a solution of 3-[2-(3-hydroxy-propyl)-thiophen-3-yl]-propionitrile 83 (0.18 g, 0.9 mmol) in DMF (2 mL) was added NBS (0.18 g, 0.99 mmol). The mixture was then stirred at room temperature for 6 hours and then concentrated in vacuo. A solution of the residue in $CH_2Cl_2$ (80 mL) was washed with water, dried over $Na_2SO_4$, filtered, and concentrated in vacuo. Purification by silica gel column chromatography (eluent: 50% EtOAc in hexane) afforded 84 (0.08 g). $^1$H NMR (400 MHz, d$^6$-DMSO) δ: 7.06 (s, 1H), 4.53 (t, J=6.0 Hz, 1H), 3.41 (dd, J=6.0 and 11.5 Hz, 2H), 2.75 (m, 6H), 1.67 (m, 2H). MS (EI) m/z [(M+H$^+$) ($^{79}$Br)] 274, [(M+H$^+$) ($^{81}$Br)] 276, [(M−OH$^+$) ($^{79}$Br)] 256 and [(M−OH$^+$) ($^{81}$Br)] 258.

4-Amino-2[4-(2-cyano-ethyl)-5-(3-hydroxy-propyl)-thiophen-2-yl]-thieno[3,2-c]pyridine-7-carboxylic acid amide (85). A mixture of 3-[5-bromo-2-(3-hydroxy-propyl)-thiophen-3-yl]-propionitrile 84 (0.08 g, 0.3 mmol), potassium acetate (0.09 g, 0.91 mmol), bis(pinacolato)diboron (0.16 g, 0.63 mmol), Pd(PPh$_3$)$_4$ (0.023 g, 0.02 mmol), and DMF (2 mL) was heated at 100° C. under nitrogen for 1 h. 4-Amino-2-bromo-thieno[3,2-c]pyridine-7-carboxylic acid amide 17 (0.54 g, 0.2 mmol), 2 M aqueous $Na_2CO_3$ solution (0.7 mL), and Pd(PPh$_3$)$_4$ (0.023 g, 0.02 mmole) were added. The reaction mixture was then heated at 100° C. under nitrogen for 40 min. then cooled to room temperature and filtered. The filtrate was concentrated in vacuo and purified by silica gel column chromatography (eluent: $CH_2Cl_2$:MeOH:$NH_4OH$ (89:9:1) to afford 85 (0.02 g) as an yellow solid. $^1$H NMR (400 z, d$^6$-DMSO) δ: 8.46 (s, 1H), 7.90 (br.s, 1H), 7.72 (s, 1H), 7.24 (s, 1H), 7.23 (br.s, 1H), 7.15 (s, 2H), 4.56 (t, 1H), 3.47 (dd, J=6.0 and 11.5 Hz, 2H), 2.82 (m, 6H), 1.75 (m, 2H). MS (EI) m/z (M+H$^+$) 387.

Example 19

Preparation of 4-amino-2-[5-(3-cyano-tetrahydro-furan-2-yl)-thiophen-3-yl]-thieno[3,2-c]pyridine-7-carboxylic acid amide

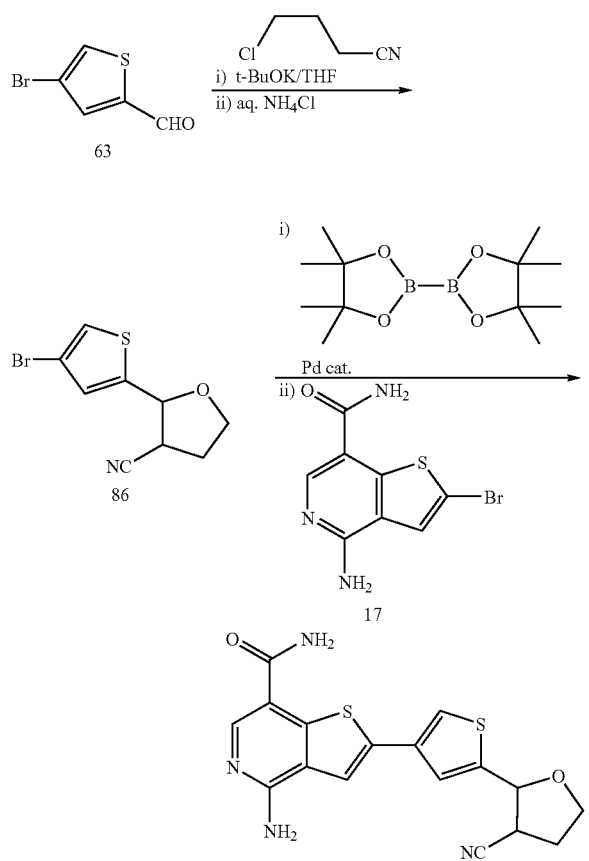

2-(4-Bromo-thiophen-2-yl)-tetrahydro-furan-3-carbonitrile (86). Addition of 4-bromo-2-thiophenecarboxaldehyde 63 (Aldrich, Wis.) (1.0 g, 5.23 mmol) to a solution of t-BuOK (1 M in THF, 5.23 mL, 5.23 mmol) at 0° C. was followed immediately by the addition of 4-chloro-butyronitrile (0.51 mL, 5.3 mmol). After 3 h, the reaction mixture was allowed to warm to the room temperature and saturated, aqueous NH$_4$Cl solution was then added. The crude reaction mixture was then separated and the aqueous fraction extracted twice with EtOAc. The combined EtOAc extracts were dried over Na$_2$SO$_4$, filtered and concentrated in vacuo. Purification by silica gel column chromatography (eluent: 10% to 20% gradient of EtOAc in hexane) afforded trans-86 (0.3 g) as an yellow liquid. $^1$H NMR (400 MHz, d$^6$-DMSO) δ: 7.68 (d, J=1.5 Hz, 1H), 7.19 (dd, J=1.0 Hz and 1.5 Hz, 1H), 5.26 (d, J=7.0 Hz, 1H), 4.04 (m, 1H), 3.96 (m, 1H), 3.44 (m, 1H), 2.41 (m, 1H), 2.29 (m, 1H). MS (EI) m/z [(M+H$^+$)$^+$ ($^{79}$Br)] 258 and [(M+H$^+$)$^+$ ($^{81}$Br)] 260.

4-Amino-2-[5-(3-cyano-tetrahydro-furan-2-yl)-thiophen-3-yl]-thieno[3,2-c]pyridine-7-carboxylic acid amide (87). 87 was prepared from 2-(4-bromo-thiophen-2-yl)-tetrahydro-furan-3-carbonitrile 86 and 4-amino-2-bromo-thieno[3,2-c]pyridine-7-carboxylic acid amide 17 in a similar manner to that described in Example 18. $^1$H NMR (400 MHz, d$^6$-DMSO) δ: 8.48 (s, 1H), 7.90 (bs, 1H), 7.89 (s, 1H), 7.77 (s, 1H), 7.46 (s, 1H), 7.26 (bs, 1H), 7.12 (s, 2H), 5.30 (d, J=7.49 Hz, 1H), 4.09 (m, 1H), 3.99 (m, 1H), 3.44 (m, 1H), 2.49 (m, 1H), 2.33 (m, 1H). MS (EI) m/z (M+H$^+$) 371.

Example 20

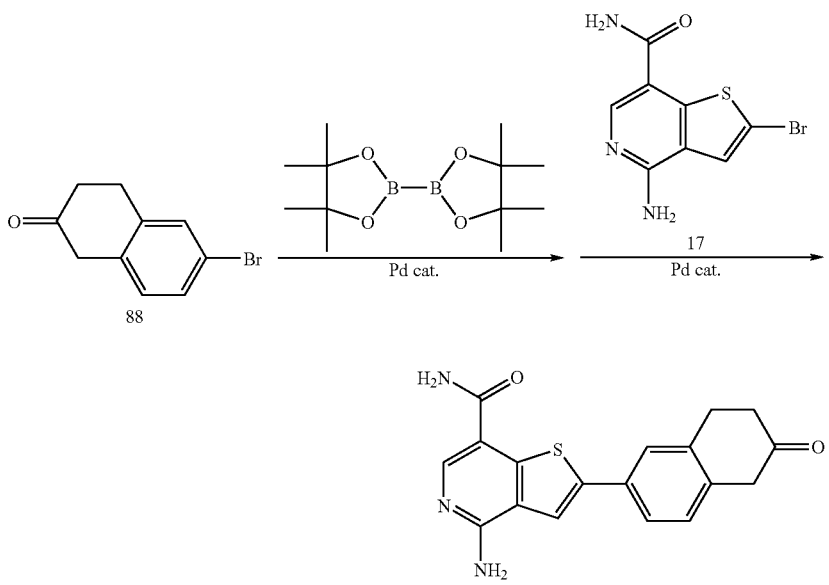

4-Amino-2-(6-oxo-5,6,7,8-tetrahydro-naphthalen-2-yl)-thieno[3,2-c]pyridine-7-carboxylic acid amide (89). 89 was prepared from 6-bromotetralone 88 (Fischer, USA) and 4-amino-2-bromo-thieno[3,2-c]pyridine-7-carboxylic acid amide 17 in a similar manner to that described in Example 14. $^1$H NMR (400 MHz, d$^6$-DMSO) δ: 2.49-2.52 (buried t, 2H), 3.13 (t, J=6.5 Hz, 2H), 3.66 (s, 2H), 7.32 (d, J=8.0 Hz, 1H), 7.59 (dd, J=9.5 Hz, 2.0 Hz, 1H), 7.66 (s, 1H), 7.65-7.78 (br s, 1H), 8.17-8.23 (br s, 1H), 8.28 (s, 1H), 8.44 (s, 1H), 8.45-8.66 (br s, 2H). MS (EI) m/z (M+H$^+$) 338, (2M+H$^+$) 675.

Example 21

Preparation of 4-Amino-2-(6-hydroxy-5,6,7,8-tetrahydro-naphthalen-2-yl)-thieno[3,2-c]pyridine-7-carboxylic acid amide

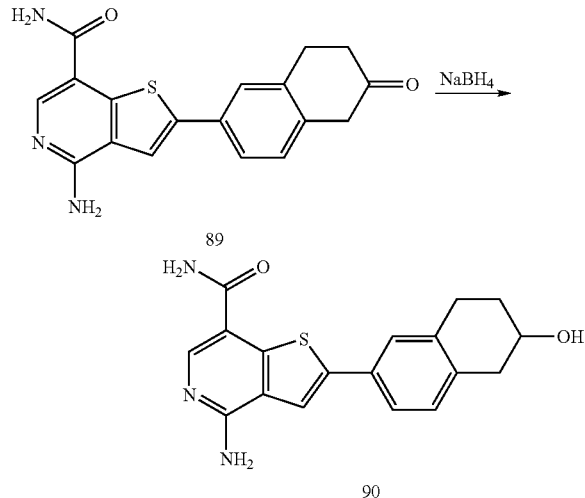

4-Amino-2-(6-hydroxy-5,6,7,8-tetrahydro-naphthalen-2-yl)-thieno[3,2-c]pyridine-7-carboxylic acid amide (90). To a suspension of 4-amino-2-(6-oxo-5,6,7,8-tetrahydro-naphthalen-2-yl)-thieno[3,2-c]pyridine-7-carboxylic acid amide 89 (24.5 mg, 0.07 mmol) in absolute ethanol (4 mL) was added sodium borohydride (11.5 mg, 0.30 mmol). After 1.25 h at room temperature, the reaction mixture was concentrated, partially dissolved in a mixture of DMSO and MeOH, and filtered. The filtrate was purified by reverse phase preparative HPLC to give 90. $^1$H NMR (400 MHz, d$^6$-DMSO) δ: 1.63-1.74 (m, 1H), 1.87-1.96 (m, 1H), 2.57-2.68 (m, 1H), 2.73-2.81 (m, 1H), 2.90-3.02 (m, 2H), 3.93-4.01 (m, 2H), 7.20 (d, J8.0 Hz, 1H), 7.44-7.48 (m, 2H), 7.70-7.83 (br s, 1H), 8.26 (s, 2H), 8.41 (s, 1H), 8.63-8.83 (br s, 2H). MS (EI) m/z (M+H$^+$) 340, (2M+H$^+$) 679.

Example 22

Preparation of 4-Amino-2-(2-methoxy-thiophen-3-yl)-thieno[3,2-c]pyridine-7-carboxylic acid amide

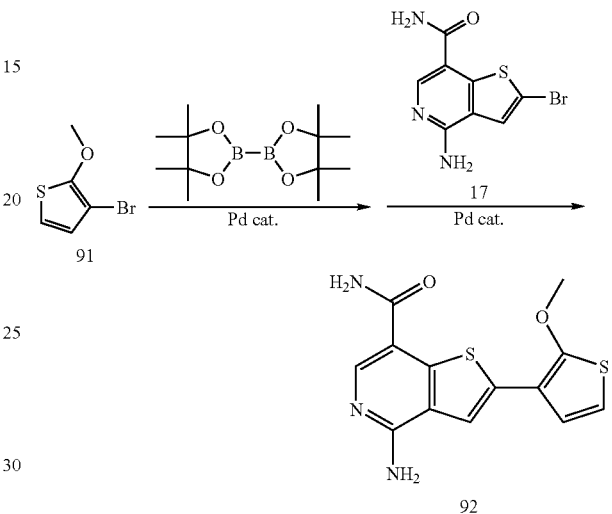

4-Amino-2-(2-methoxy-thiophen-3-yl)-thieno[3,2-c]pyridine-7-carboxylic acid amide (92). 92 was prepared from 3-bromo-2-methoxythiophene 91 (Zhang, Y.; Hornfeldt, A.-B.; Gronowitz, S.; Stalhandske, C. Acta Chemica Scand. 1994, 48, 843-849) and 4-amino-2-bromo-thieno[3,2-c]pyridine-7-carboxylic acid amide in a similar manner to that described for Example 14. $^1$H NMR (400 MHz, d$^6$-DMSO) δ: 4.10 (s, 3H), 7.13 (d, J6.0 Hz, 1H), 7.28 (d, J6.0 Hz, 1H), 7.69-7.78 (br s, 1H), 8.19 (s, 1H), 8.20-8.30 (br s, 1H), 8.40 (s, 1H), 8.60-8.80 (br s, 2H). MS (EI) m/z (M+H$^+$) 306, (2M+H$^+$) 611.

Example 23

Preparation of 4-Amino-2-(1-methyl-2,2-dioxo-2,3-dihydro-1H-2Δ6-benzo[c]isothiazol-5-yl)-thieno[3,2-c]pyridine-7-carboxylic acid amide

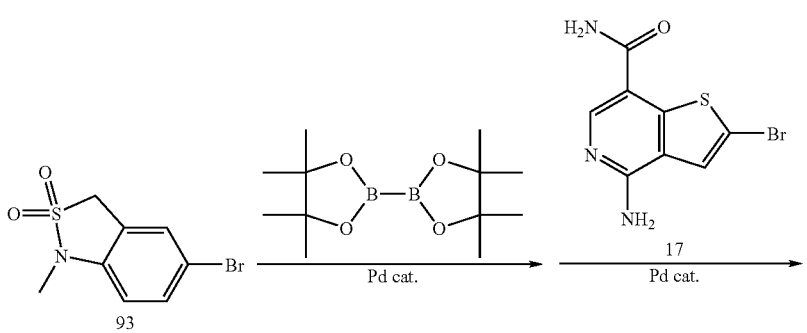

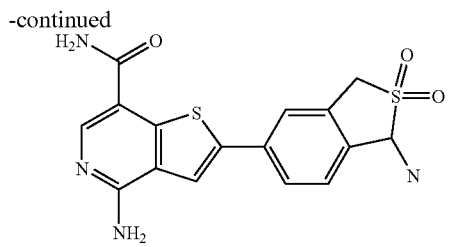

94

4-Amino-2-(1-methyl-2,2-dioxo-2,3-dihydro-1H-2□6-benzo [c]isothiazol-5-yl)-thieno[3,2-c]pyridine-7-carboxylic acid amide (94). 94 was prepared from 5-bromo-1-methyl-1,3-dihydro-benzo[c]isothiazole 2,2-dioxide 93 (Skorcz, J. A.; Suh, J. T.; Germershausen, R. L. J. Heterocyclic Chem. 1973, 10, 249-253) and 4-amino-2-bromo-thieno[3,2-c]pyridine-7-carboxylic acid amide 17 in a similar manner to that described for Example 14. $^1$H NMR (400 MHz, d$^6$-DMSO) δ: 3.29 (s, 3H), 4.99 (s, 2H), 7.24-7.29 (m, 1H), 7.59-7.75 (br s, 1H), 7.83-7.97 (m, 2H), 8.39 (s, 1H), 8.60 (s, 1H), 8.71-8.90 (br s, 1H). MS (EI) m/z (M+H$^+$) 375.

Example 24

Preparation of 1-(4-Amino-2-phenyl-thieno[3,2-c]pyridin-7-yl)-ethanone

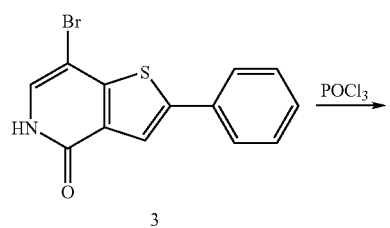

3

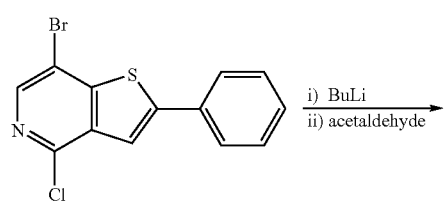

95

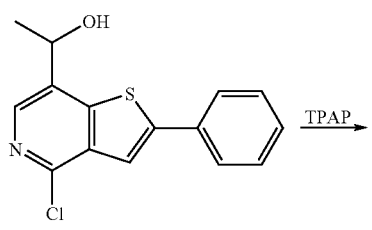

96

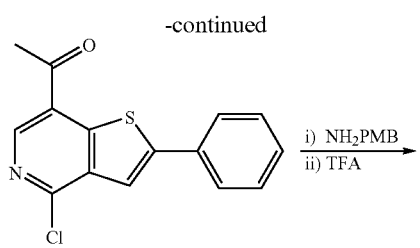

97

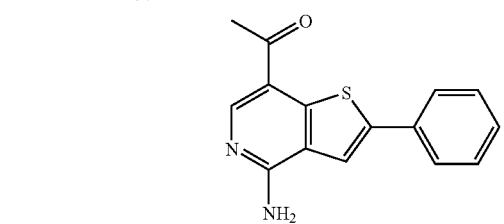

98

Bromo-2-oxo-4 dihydrothieno[3,2-c]pyridine (1). Bromo-2-oxo-4 dihydrothieno[3,2-c]pyridine, 1 was prepared according to Eloy and Deryckere (*Bull. Soc. Chim. Belges*, 1970, 79:301-312).

2-Phenyl-4-oxo-4,5-dihydrothieno[3,2-c]pyridine (2). Compound 1 (0.43 mmol) was dissolved with heating (ca. 85° C.) in DMF (1.5 mL). To the solution was added phenylboronic acid (0.50 mmol), Pd(dppf)Cl$_2$CH$_2$Cl$_2$ (0.075 mmol), K$_2$CO$_3$ (0.564 mmol) and H$_2$O (1.5 mL). The vessel was purged with N$_2$ for 10 min. The solution, under N$_2$, was heated to 85° C. After 2 h, solvents were removed in vacuo. The residue was purified by Si-gel column chromatography (5% MeOH in CH$_2$Cl$_2$) to yield 0.074 g. $^1$H NMR (400 MHz, d$^6$-DMSO) δ: 11.49 (s, 1H), 7.88 (s, 1H), 7.77 (d, J=7 Hz, 2H), 7.47 (t, J=7 Hz 2H), 7.38 (t, J=7 Hz 1H), 7.29 (t, J=6 Hz, 1H), 6.88 (d, J=7 Hz, 1H).

7-Bromo-2-phenyl-4-oxo-4,5-dihydrothieno[3,2-c]pyridine (3). To compound 2 (3.92 g, 17.24 mmol) in DMF (133 mL) was added NBS (3.37 g, 19.0 mmol). The solution was heated to 60° C. After 1 h, the solution volume was reduced to approximately one half the volume, and the solution was poured into H$_2$O (700 mL). The precipitate was filtered, washed with water, and dried to yield 5.08 g of 3. $^1$H NMR (400 MHz, d$^6$-DMSO) δ: 11.84 (s, 1H), 8.05 (s, 1H), 7.82 (d, J=7 Hz, 2H), 7.61 (s, 1H), 7.48 (t, J=7 Hz 2H), 7.4 (t, J=7 Hz, 1H).

7-Bromo-4-chloro-2-phenyl-thieno[3,2-c]pyridine (95). A mixture of 7-bromo-2-phenyl-5H-thieno[3,2-c]pyridin-4-one 3 (2.28 g, 7.5 mmol) in phosphorus oxychloride (27 mL) was heated at reflux for 21 h. The reaction mixture was basified to pH 5-6 by the addition of saturated aqueous sodium carbonate and extracted with dichloromethane (1×). The organic layer was dried over Na₂SO₄, filtered, and the filtrate was purified by silica gel column chromatography (eluent: hexane:EtOAc, 97:3) to give 95.

¹H NMR (400 MHz, CDCl₃) δ: 7.41-7.52 (m, 3H), 7.72-7.78 (m, 3H), 8.28 (s, 1H). MS (EI) m/z (M+H⁺) 324.

1-(4-Chloro-2-phenyl-thieno[3,2-c]pyridin-7-yl)-ethanol (96). 7-bromo-4-chloro-2-phenyl-thieno[3,2-c]pyridine 95 (130 mg, 0.40 mmol) was azeotroped to dryness from benzene and dissolved in THF (11 mL). Upon cooling to −78° C., the solution was treated dropwise with n-BuLi (168 μl of a 2.5 M solution in hexane, 0.42 mmol). After 2 min, acetaldehyde (50 μl, 0.89 mmol) was added and the resultant solution was stirred at −78° C. for 1 h. After this time, the reaction mixture was warmed to 0° C., quenched with saturated aqueous ammonium chloride and extracted with ethyl acetate (3×). The organic layers were dried over Na₂SO₄, filtered, and the filtrate was purified by silica gel column chromatography (eluent: hexane:EtOAc, 4:1) to give 96. ¹H NMR (400 MHz, CDCl₃) δ: 1.68 (d, J=6.5 Hz, 3H), 2.29 (bd, 1H), 5.22-5.29 (m, 1H), 7.38-7.49 (m, 3H), 7.69 (s, 1H), 7.73-7.78 (m, 2H), 8.13 (s, 1H). MS (EI) m/z (M+H⁺) 290.

1-(4-Chloro-2-phenyl-thieno[3,2-c]pyridin-7-yl)-ethanone (97). To a suspension of 1-(4-chloro-2-phenyl-thieno[3,2-c]pyridin-7-yl)-ethanol 96 (92 mg, 0.32 mmol) and 168 mg of powdered 4A molecular sieves in dichloromethane (35 mL) was added TPAP (11 mg, 0.03 mmol). The resultant mixture was stirred at room temperature for 1 h. After this time, the reaction mixture was diluted with dichloromethane and washed with saturated aqueous sodium thiosulfate (1×) and saturated aqueous copper sulfate (1×). The organic layer was dried over Na₂SO₄, filtered, and the filtrate was purified by silica gel column chromatography (eluent: hexane:EtOAc, 17:3) to give 97. ¹H NMR (400 MHz, CDCl₃) δ: 2.79 (s, 3H), 7.40-7.53 (m, 3H), 7.75 (s, 1H), 7.78-7.83 (m, 2H), 8.83 (s, 1H). MS (EI) m/z (M+H⁺) 288.

1-(4-Amino-2-phenyl-thieno[3,2-c]pyridin-7-yl)-ethanone (98). To a suspension of 1-(4-chloro-2-phenyl-thieno[3,2-c]pyridin-7-yl)-ethanone 97 (61 mg, 0.21 mmol) and potassium carbonate (174 mg, 1.26 mmol) in DMF (1.8 mL) was added 4-methoxybenzylamine (85 μl, 0.64 mmol). The resultant mixture was heated at 50° C. for 6.75 h. After this time, 20 mL of a 1:1 mixture of dichloromethane and methanol was added and the resultant slurry was filtered. The filtrate was concentrated and the residue was dissolved in trifluoroacetic acid (7 mL). The resultant mixture was heated at 55° C. for 2.75 h. After this time, the reaction mixture was concentrated and the residue was purified by silica gel column chromatography (eluent: dichloromethane:MeOH:Et₃N, 98.5:1.5:0.5) to give 98.

¹H NMR (400 MHz, CDCl₃) δ: 2.66 (s, 3H), 5.78-6.15 (br s, 2H), 7.37 (t, J=7.0 Hz, 1H), 7.45 (t, J=7.5 Hz, 2H), 7.54 (s, 1H), 8.0 (d, J=3.5 Hz, 2H), 8.56 (s, 1H). MS (EI) m/z (M+H⁺) 269.

Example 25

Preparation of 4-cyclohexyamino-2-(4'-t-butylphenyl)-thieno[3,2-c]pyridine 7-carboxylic acid amide (103)

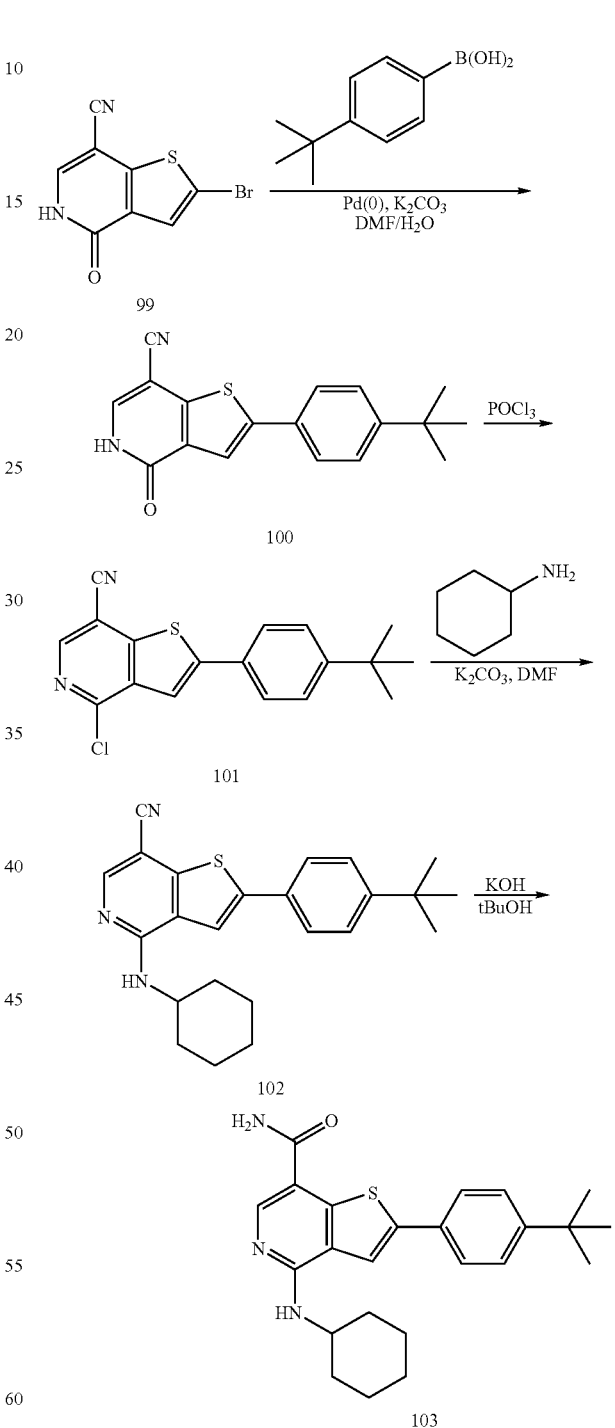

7-Cyano-2-bromo-4-oxo-4,5-dihydrothieno[3,2-c]-pyridine (99). 7-Cyano-2-bromo-4-oxo-4,5-dihydrothieno[3,2-c]-pyridine was prepared according to the procedure described in U.S. Pat. No. 3,891,660.

7-Cyano-2-(4'-t-butylphenyl)-4-oxo-4,5-dihydrothieno[3,2-c]-pyridine (100). To a solution of 7-cyano-2-bromo-4-oxo-4,5-dihydrothieno[3,2-c]-pyridine (2.0 g, 7.84 mmol) in DMF (40 mL) and water (15 mL) was added 4-t-butylphenyl boronic acid (2.1 g, 11.8 mmol), potassium carbonate (1.4 g, 10.1 mmol) and [1,1'-bis(diphenylphosphino)ferrocene] dichloropalladium(II), complex with dichloromethane (1:1) (0.192 g, 0.23 mmol). The resulting mixture was stirred under nitrogen for 4 h at 80° C. After this time the mixture was diluted with DMF (20 mL), filtered through celite to remove palladium residues and water (100 mL) added. The precipitated solid was filtered, washed thoroughly with water and dried in air by suction at room temperature providing 1.4 g of 100 which was used without further analysis or purification.

4-Chloro-7-cyano-2-(4'-t-butylphenyl)-thieno[3,2-c]pyridine (101). 7-Cyano-2-(4'-t-butylphenyl)-4-oxo-4,5-dihydrothieno[3,2-c]-pyridine was dissolved in phosphorus oxychloride (25 mL) and the resulting solution heated at reflux for 2 h. After this time the mixture was poured into ice and stirred for 1 h. The precipitated solid was filtered and washed with water, drying by suction in air at room temperature affording 1.05 g of 101.

¹H NMR (300 MHz, d⁶-DMSO) δ 8.83 (s, 1H), 8.11 (s, 1H), 7.92 (d, 2H), 7.56 (d, 2H), 1.34 (s, 9H).

4-Cyclohexylamino-7-cyano-2-(4'-t-butylphenyl)-thieno [3,2-c]pyridine (102). To a solution of 4-chloro-7-cyano-2-(4'-t-butylphenyl)-thieno[3,2-c]pyridine (0.05 g, 0.153 mmol) in DMF was added cyclohexylamine (0.017 g, 0.168 mmol) and potassium carbonate (0.023 g, 0.168 mmol). The resulting mixture was stirred under nitrogen at 80° C. for 2 h. After this time the mixture was partitioned between ethyl acetate (10 mL) and saturated aqueous sodium bicarbonate solution (10 mL), and the organic layer washed with water and brine, then dried over magnesium sulphate and concentrated under reduced pressure. Purification by silica gel chromatography (eluent 20% ethyl acetate in hexane) afforded 0.042 g of 102. ¹H NMR (400 MHz, CDCl₃) δ 8.27 (s, 1H), 7.63 (d, 2H), 7.50 (d, 2H), 7.38 (s, 1H), 5.14 (bs, 1H), 4.20 (bs, 1H), 2.18 (m, 2H), 1.80 (m, 4H), 1.6-1.12 (m, 13H).

4-Cyclohexyamino-2-(4'-t-butylphenyl)-thieno[3,2-c]pyridine 7-carboxylic acid amide (103). 4-Cyclohexylamino-7-cyano-2-(4'-t-butylphenyl)-thieno[3,2-c]pyridine (0.042 g, 0.11 mmol) was taken up in t-butanol (2 mL) and powdered potassium hydroxide (0.007 g, 0.12 mmol) was added. The resulting mixture was heated to reflux for 3 h. After that time the mixture was cooled and water added, the resulting solid was filtered, washed with water and dried to yield 25 mg of 103. ¹H NMR (400 MHz, CDCl₃), δ 8.22 (s, 1H), 7.69 (d, 2H), 7.47 (d, 2H), 7.36 (s, 1H), 5.58 (bs, 2H), 5.07 (d, 1H), 4.05 (m, 1H), 2.17 (m, 2H), 1.82 (m, 2H), 1.71 (m, 1H), 1.50 (m, 2H), 1.36 (s, 9H), 1.30 (m, 3H). MS (EI) m/z (M+H⁺) 408, (2M+H⁺) 815.

Example 26

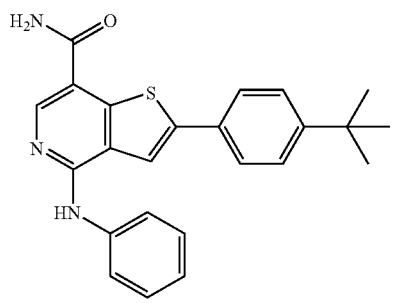

104

Preparation of 4-phenylamino-2-(4'-t-butylphenyl)-thieno [3,2-c]pyridine 7-carboxylic acid amide (104). 104 was prepared from 4-chloro-7-cyano-2-(4'-t-butylphenyl)-thieno[3,2-c]pyridine (101) and aniline in a similar manner to that described for Example 25. ¹H NMR (400 MHz, CDCl₃) δ 8.41 (s, 1H), 7.70 (m, 4H), 7.51 (s, 1H), 7.47 (d, 2H), 7.40 (t, 2H), 7.19 (bs, 1H), 7.16 (t, 1H), 1.28 (s, 9H). MS (EI) m/z (M+H⁺) 402.

Example 27

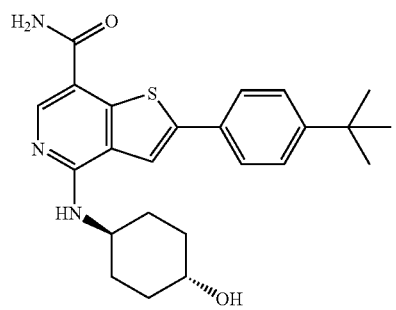

105

Preparation of 4-(4'-trans-hydroxycyclohexylamino)-2-(4"-t-butylphenyl)-thieno[3,2-c]pyridine 7-carboxylic acid amide (105). 105 was prepared from 4-chloro-7-cyano-2-(4'-t-butylphenyl)-thieno[3,2-c]pyridine (101) and 4-trans-hydroxycyclohexylamine in a similar manner to that described for Example 25. ¹H NMR (400 MHz, d⁶ DMSO) δ 8.51 (s, 1H), 8.22 (s, 1H), 7.89 (bs, 1H), 7.65 (d, 2H), 7.50 (d, 2H), 7.25 (s, 1H), 7.24 (s, 1H), 4.62 (d, 1H), 4.07 (m, 1H), 3.47 (m, 1H), δ 2.0 (m, 2H), 1.90 (m, 2H), 1.41 (m, 4H), 1.32 (s, 9H). MS (EI) m/z (M+H⁺) 424.

Example 28

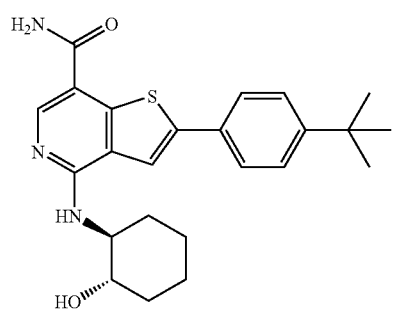

106

Preparation of 4-(2'-trans-hydroxycyclohexylamino)-2-(4"-t-butylphenul)-thieno[3,2-c]pyridine 7-carboxylic acid amide (106). 106 was prepared from 4-chloro-7-cyano-2-(4'-t-butylphenyl)-thieno[3,2-c]pyridine (101) and 2-trans-hydroxycyclohexylamine in a similar manner to that described for Example 25. ¹H NMR (400 MHz, d⁶ DMSO) δ 8.48 (s, 1H), 8.25 (s, 1H), 7.88 (bs, 1H), 7.67 (d, 2H), 7.51 (d, 2H), 7.26 (s, 1H), 7.25 (s, 1H), 4.77 (d, 1H), 4.03 (m, 1H), 3.52 (m, 1H), 2.00 (m, 2H), 1.70 (m, 2H), 1.35 (s, 9H), 1.30 (m, 4H). MS (EI) m/z (M+H⁺) 424.

Example 29

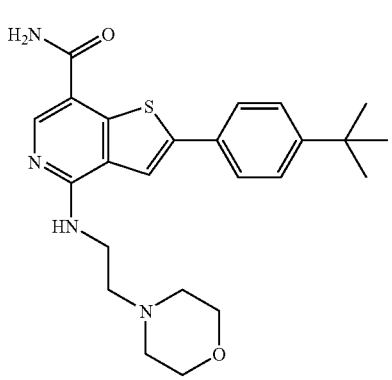

Preparation of 4-[2'-(4"-morpholine)ethylamino]-2-(4"-t-butylphenul)-thieno[3,2-c]pyridine 7-carboxylic acid amide (107). 107 was prepared from 7-cyano-4-chloro-2-(4'-t-butylphenyl)-thieno[3,2-c]pyridine (101) and 4-(2-aminoethyl)morpholine in a similar manner to that described in Example 25. $^1$H NMR (300 MHz, d$^6$-DMSO) δ 8.45 (s, 1H), 8.0 (bs, 1H), 7.90 (s, 1H), 7.5 (d, 2H), 7.4 (d, 3H), 3.8 (bm), 3.3 (bm, 8H), 1.2 (s, 9H). MS (EI) m/z (M+H$^+$) 439, 352.

Example 30

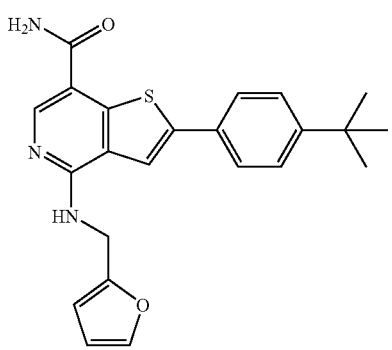

Preparation of 4-furfurylamino-2-(4'-t-butylphenyl)-thieno[3,2-c]pyridine 7-carboxylic acid amide (108). 108 was prepared from 4-chloro-7-cyano-2-(4'-t-butylphenyl)-thieno[3,2-c]pyridine (101) and furfurylamine in a similar manner to that described in Example 25. $^1$H NMR (300 MHz, d$^6$-DMSO) δ 8.25 (s, 1H), 8.0 (s, 1H), 7.9 (bs, 1H), 7.4 (d, 3H), 7.3 (d, 3H), 6.2 (bs, 2H), 4.55 (d, 2H), 1.1 (s, 9H). MS (EI) m/z (2M+H$^+$) 811, (M+H$^+$) 406.5

Example 31

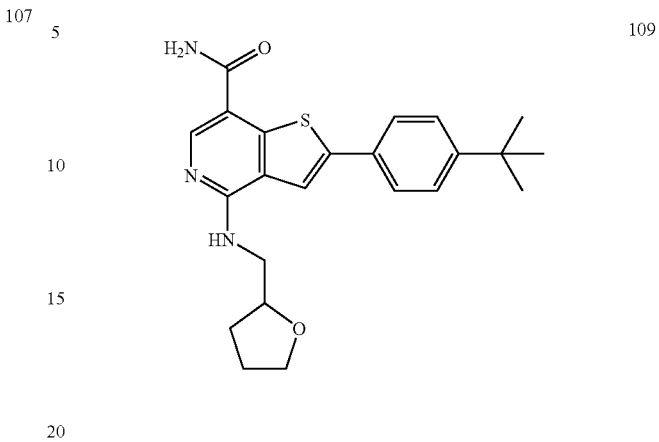

Preparation of 4-tetrahydrofurfurylamino-2-(4'-t-butylphenyl)-thieno[3,2-c]pyridine 7-carboxylic acid amide (109). 109 was prepared from 4-chloro-7-cyano-2-(4'-t-butylphenyl)-thieno[3,2-c]pyridine (101) and tetrahydrofurfurylamine in a similar manner to that described in Example 25. $^1$H NMR (300 MHz, d$^6$-DMSO) δ 8.4 (s, 1H), 8.3 (s, 1H), 7.7 (d, 2H), 7.55 (d, 2H), 4.15 (m, 1H), 3.6-3.8 (m, 4H), 2.0 (m, 1H), 1.90 (m, 2H), 1.7 (m, 1H), 1.3 (s, 9H). MS (EI) m/z (2M+H$^+$) 819, (M+H$^+$) 410, 326.

Example 32

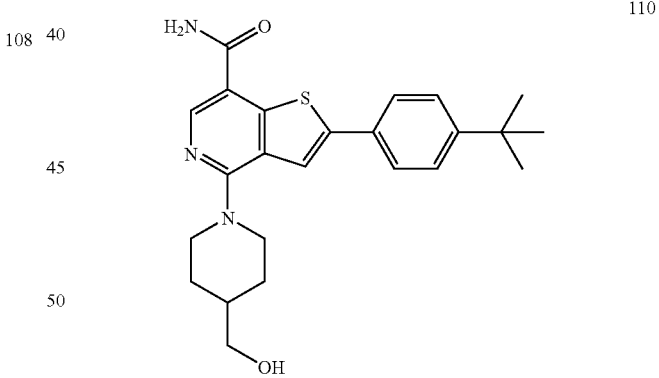

Preparation of 4-(4'-hydroxymethylpiperidinyl)-2-(4"-t-butylphenyl)-thieno[3,2-c]pyridine 7-carboxylic acid amide (110). 110 was prepared from 4-chloro-7-cyano-2-(4'-t-butylphenyl)-thieno[3,2-c]pyridine (101) and 4-piperidinemethanol in a similar manner to that described in Example 25. $^1$H NMR (300 MHz, d$^6$-DMSO) δ 8.6 (s, 1H), 8.25 (s, 1H), 7.8 (d, 3H), 7.65 (bs, 1H), 7.5 (d, 2H), 4.3 (d, 2H), 3.4 (d, 2H), 3.2 (t, 2H), 1.90 (d, 2H), 1.4 (m, 2H), 1.35 (s, 9H). MS (EI) m/z (2M+H$^+$) 847.5, (M+H$^+$) 424

Example 33

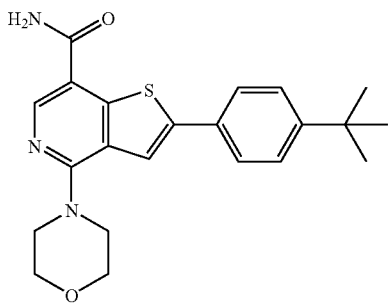

111

Preparation of 4-morpholino-2-(4'-t-butylphenyl)thieno[3,2-c]pyridine 7-carboxylic acid amide (111). 111 was prepared from 4-chloro-7-cyano-2-(4'-t-butylphenyl)-thieno[3,2-c]pyridine (101) and morpholine in a similar manner to that described in Example 25. $^1$H NMR (300 MHz, CDCl$_3$) δ 8.35 (s, 1H), 7.6 (d, 2H), 7.4 (d, 3H), 6.2 (bs, 2H), 3.9 (m, 4H), 3.7 (m, 4H), 1.3 (s, 9H). MS (EI) m/z (2M+H$^+$) 791.5, (M+H$^+$) 396.5.

Example 34

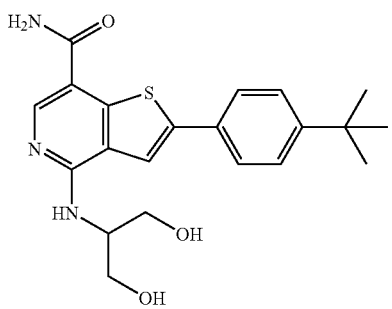

112

Preparation of 4-(1'-hydroxymethyl)ethanolamino-2-(4'-t-butylphenyl)-thieno[3,2-c]pyridine 7-carboxylic acid amide (112). 112 was prepared from 4-chloro-7-cyano-2-(4'-t-butylphenyl)-thieno[3,2-c]pyridine (101) and 2-amino-1,3-propanediol in a similar manner to that described in Example 25. $^1$H NMR 300 MHz, d$^6$-DMSO) δ 8.4 (m, 2H), 8.25 (bs, 1H), 7.7 (d, 2H), 7.6 (bs, 1H), 7.5 (d, 2H), 4.3 (m, 1H), 3.7 (m, 4H), 1.3 (s, 9H). MS (EI) m/z (2M+H$^+$) 799.5, (M+H$^+$) 400.5.

Example 35

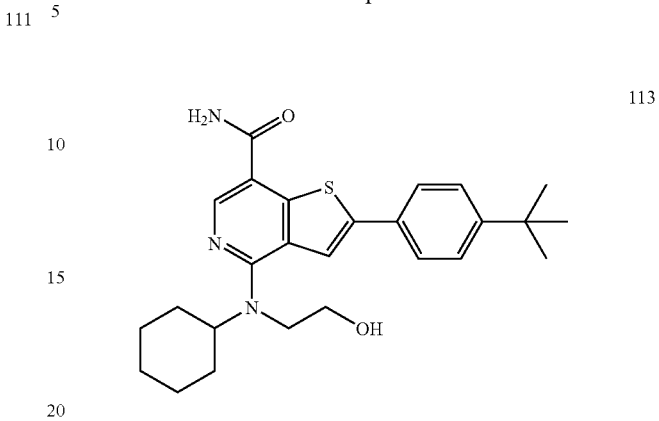

113

Preparation of 4-(N-cyclohexyl)ethanolamino-2-(4'-t-butylphenyl)-thieno[3,2-c]pyridine 7-carboxylic acid amide (113). 113 was prepared from 4-chloro-7-cyano-2-(4'-t-butylphenyl)-thieno[3,2-c]pyridine (101) and N-cyclohexylethanolamine in a similar manner to that described in Example 25. $^1$H NMR (300 MHz, d$^6$-DMSO) δ 8.65 (s, 1H), 8.05 (m, 1H), 7.7 (d, 3H), 7.6 (d, 2H), 4.4 (t, 1H), 3.7 (m, 2H), 3.6 (m, 2H), 1.7-1.9 (m, 10H). MS (EI) m/z (M+H$^+$) 452.5.

Example 36

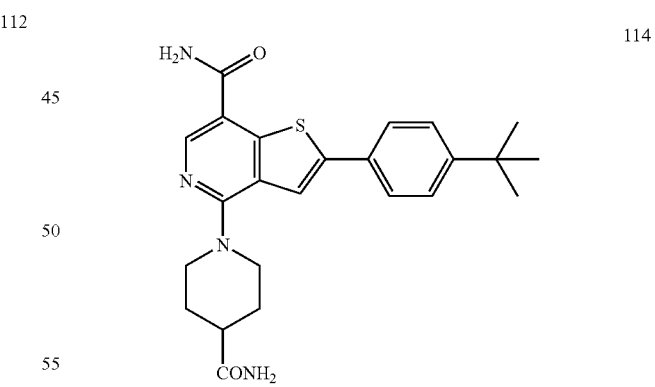

114

Preparation of 4-(4'-amidopiperidin-1'-yl)-2-(4'-t-butylphenyl)-thieno[3,2-c]pyridine 7-carboxylic acid amide (114). 114 was prepared from 4-chloro-7-cyano-2-(4'-t-butylphenyl)-thieno[3,2-c]pyridine (101) and isonipecotamide in a similar manner to that described in Example 25. $^1$H NMR (300 MHz, d$^6$-DMSO) δ 8.5 (s, 1H), 8.1 (bs, 1H), 7.7 (d, 3H), 7.5 (bs, 1H), 7.4 (d, 2H), 7.3 (bs, 1H), 6.8 (bs, 1H), 4.1 (d, 2H), 3.1 (t, 1H), 1.75 (m, 6H), 1.1 (s, 9H). MS (EI) m/z (M+H⁺) 437.

Example 37

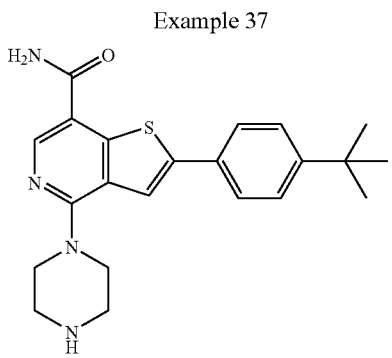

115

Preparation of 4-(N-piperazinyl)-2(4'-t-butylphenyl) thieno[3,2-c]pyridine 7-carboxylic acid amide (115). 115 was prepared from 4-chloro-7-cyano-2-(4'-t-butylphenyl)-thieno[3,2-c]pyridine (101) and piperazine in a similar manner to that described in Example 25. ¹H NMR (300 MHz, d⁶-DMSO) δ 8.7 (bs, 1H), 8.6 (s, 1H), 8.1 (bs, 1H), 7.7 (m, 3H), 7.4 (d, 2H), 3.65 (m, 4H), 1.2 (s, 9H). MS (EI) m/z (2M+H⁺) 789.5, (M+H⁺) 395.5.

Example 38

Preparation of 4-(4'-trans-hydroxycyclohexylamino)-2-(4''-ethylsulphonylphenyl)-thieno[3,2-c]pyridine 7-carboxylic amide

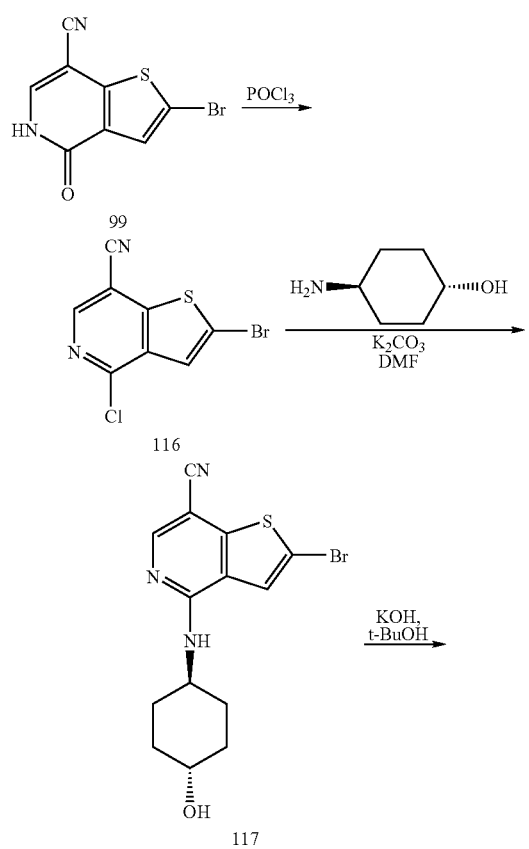

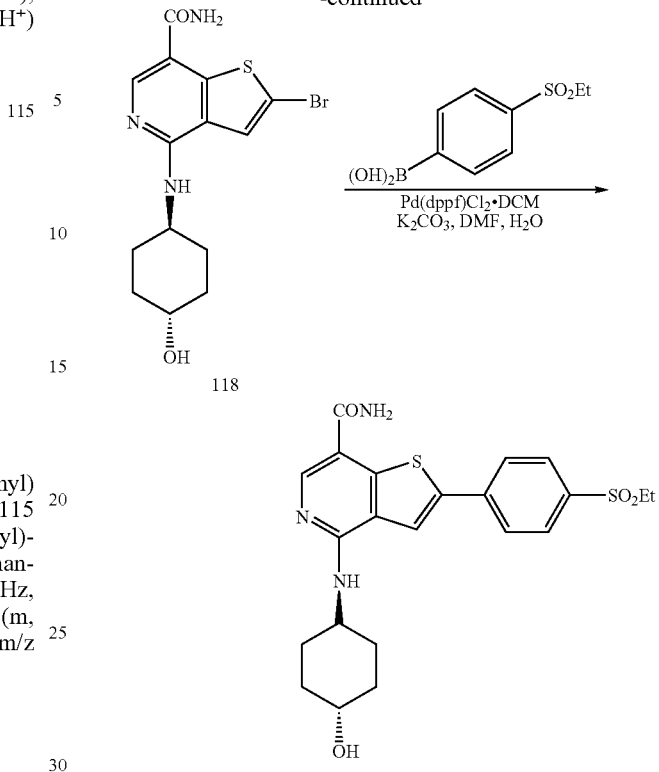

7-Cyano-2-bromo-4-oxo-4,5-dihydrothieno[3,2-c]-pyridine (99). 7-Cyano-2-bromo-4-oxo-4,5-dihydrothieno[3,2-c]-pyridine was prepared according to the procedure described in U.S. Pat. No. 3,891,660.

2-Bromo-4-chloro-7-cyano-thieno[3,2-c]pyridine (116). 2-Bromo-7-cyano-4-oxo-4,5-dihydrothieno[3,2-c]-pyridine (99) (2.0 g, 7.84 mmol) was dissolved in phosphorus oxychloride (60 mL) and the resulting solution heated at reflux for 2 h. After this time the mixture was poured into ice and stirred for 1 h. The precipitated solid was filtered, washed with water and dried (50° C., P₂O₅, in vacuo), affording a brown solid (1.99 g). ¹H NMR (300 MHz, d⁶-DMSO) δ 9.05 (s, 1H), 8.21 (s, 1H)

2-Bromo-4-(4'-trans-hydroxycyclohexylamino)-7-cyano-thieno[3,2-c]pyridine (117). To a solution of 2-bromo-4-chloro-7-cyano-thieno[3,2-c]pyridine (116) (1.99 g, 7.27 mmol) in DMF was added 4-trans-hydroxycyclohexylamine (1.21 g, 7.98 mmol) and potassium carbonate (3.0 g, 21.7 mmol). The resulting mixture was stirred under nitrogen at 70° C. for 2 h. The solvent was removed in vacuo and the brown solid triturated in water. The brown solid was filtered, washed with water and dried (50° C., P₂O₅, in vacuo), affording a brown solid (2.73 g). ¹H NMR (300 MHz, d⁶-CDCl₃) δ 8.20 (s, 1H), 7.19 (s, 1H), 5.85 (d, 1H), 4.10 (m, 1H), 2.2-1.9 (dd, 4H), 1.5-1.13 (m, 4H)

2-Bromo-4-(4'-trans-hydroxycyclohexylamino)-thieno[3,2-c]pyridine 7-carboxylic amide (118). 2-Bromo-4-(4'-trans-hydroxycyclohexylamino)-7-cyano-thieno[3,2-c]pyridine (117) (2.73 g, 7.76 mmol) was taken up in t-butanol (70 mL) and powdered potassium hydroxide (2.2 g, 39 mmol) added. The resulting mixture was heated to reflux for 2 h. After cooling the mixture was diluted with water (50 mL) and ethyl acetate (200 mL). The organic layer was separated, washed with water (50 mL), and dried (magnesium sulphate). Evaporation of the solvent in vacuo gave a yellow solid (2.3 g). $^1$H NMR (300 MHz, d$^6$-MeOD) δ 8.69 (s, 1H), 7.95 (s, 1H), 4.32 (bm, 1H), 3.84 (bm, 1H), 2.4-2.2 (m, 4H), 1.70 (t, 4H).

4-(4'-trans-hydroxycyclohexylamino)-2-(4"-ethylsulphonylphenyl)-thieno[3,2-c]pyridine 7-carboxylic amide (119). To a mixture of 2-bromo-4-(4'-trans-hydroxycyclohexylamino)-thieno[3,2-c]pyridine 7-carboxylic amide (118) (50 mg, 0.14 mmol) in DMF (2 mL) and water (0.2 mL) was added 4-ethylsulphonylphenyl boronic acid (43 mg, 0.2 mmol), potassium carbonate (30 mg) and [1,1'-bis(diphenylphosphino)ferrocene]dichloropalladium(II), complex with dichloromethane (10 mg, 0.01 mmol). The resulting mixture was stirred under nitrogen at 100° C. for 1 h. After this time the mixture was cooled, filtered and purified by preparative HPLC. The desired fractions were freeze dried to give a white solid (91 mg). $^1$H NMR (300 MHz, d$^6$-MeOD) δ 8.28 (s, 1H), 7.88 (s, 1H), 3.77 (bm, 1H), 3.58 (bm, 1H), 3.13 (q, 2H), 2.05 (bm, 4H), 1.64-1.42 (m, 4H), 1.13 (t, 3H). MS (EI) m/z (M+H$^+$) 460.

Example 39

Preparation of 4-(trans-4'-hydroxycyclohexylamino)-2-(4"-N-morpholinethoxyphenyl)-thieno[3,2-c]pyridine 7-carboxylic acid amide) (122)

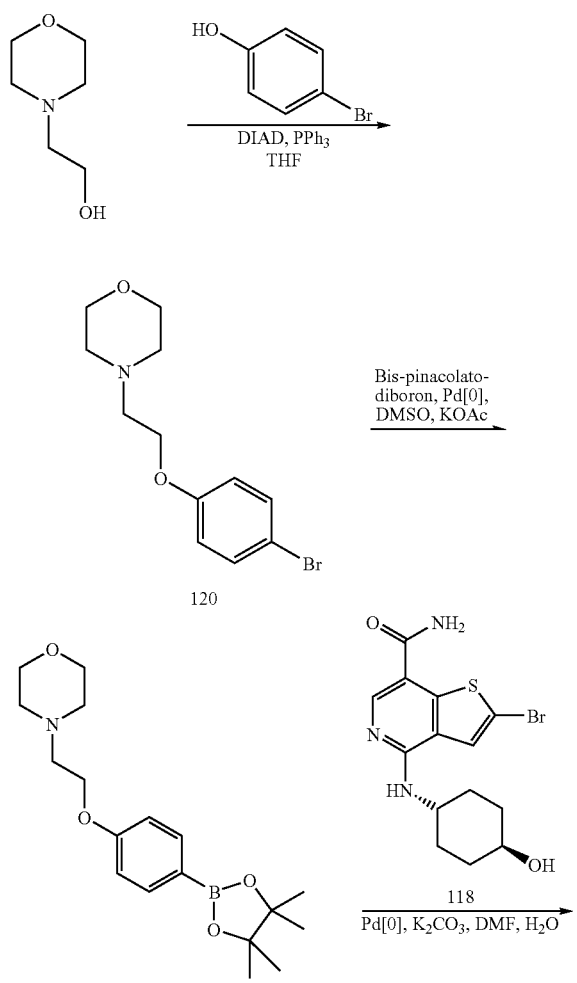

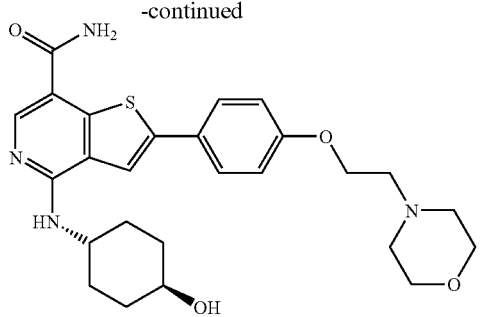

N-(4-bromophenoxyethyl)morpholine (120). To a solution of 4-bromophenol (3.30 g, 20.0 mmol), triphenylphoshine (5.25 g, 20.0 mmol) and N-(2-hydroxyethyl)morpholine (2.51 g, 19.1 mmol) in THF (30 mL) was added diisopropyl azodicarboxylate (3.94 mL, 20.0 mmol) over 10 min. The reaction mixture was stirred at room temperature for 2 h, and then hydrochloric acid (50 mL, 1N) was added. The mixture was extracted with diethyl ether (2×50 mL), and then the pH was adjusted to 10 with 2N aq. NaOH. The mixture was then extracted with ethyl acetate (2×50 mL) and the combined organic layers were dried over MgSO$_4$ and concentrated under reduced pressure to afford N-(4-bromophenoxyethyl)morpholine (4.54 g, 15.9 mmol) as a white solid.

N-(4-pinacolatoboronylphenoxyethyl)morpholine (121). To a solution of bis-pinacolatodiboron (0.113 g, 0.44 mmol), KOAc (0.140 g, 1.45 mmol) and [1,1'-bis(diphenylphosphino)ferrocene]dichloropalladium(II) complex with dichloromethane (1:1) (0.020 g, cat.) in DMSO (3 mL) at 100° C. was added N-(4-bromophenoxyethyl)morpholine (120) (0.126 g, 0.44 mol) in DMSO (3 mL) over 30 min. After a further 4 h, the reaction mixture was cooled, diluted with ethyl acetate (50 mL), and extracted with brine (25 mL) and water (2×25 mL). The organic layer was then concentrated under reduced pressure to afford N-(4-pinacolatoboronylphenoxyethyl)morpholine (0.190 g) as a pale brown solid which was used without further purification.

4-(trans-4'-hydroxycyclohexyamino-2-(4"-N-morpholinethoxyphenyl)-thieno[3,2-c]pyridine 7-carboxylic acid amide (122). A solution of 4-(trans-4'-hydroxycyclohexylamino)-2-bromothieno[3,2-c]pyridine 7-carboxylic acid amide (118), prepared as described in Example 38, (0.040 g, 0.108 mmol), N-(4-pinacolatoboronylphenoxyethyl)morpholine (0.085 g, from above experiment), K$_2$CO$_3$ (0.060 g, 0.43 mmol) in DMF (1 mL) and water (0.5 mL) was heated to 75° C. After 16 h, the reaction mixture was filtered and purified by preparative HPLC to afford (122) as a white powder after freeze-drying (0.031 g). $^1$H NMR (300 MHz, DMSO) δ, 1.20-1.52 (m, 4H), 1.84-2.03 (m, 4H), 3.86-4.05 (4H, m), 4.38-4.48 (2H, m), 7.16 (2H, d), 7.60 (1H, br s), 7.71 (2H, d), 8.23 (2H, br s), 8.40 (1H, s), 10.21 (1H, br s). Signals for the remaining 8 protons are obscured by the DMSO peak at 3.2-3.6 ppm. MS (EI) m/z (M+H$^+$) 497.

Example 40

Preparation of 4-(trans-4'-hydroxycyclohexylamino)-2-(4"-methylthiazolethoxyphenyl)-thieno[3,2-c]pyridine 7-carboxylic acid amide (123)

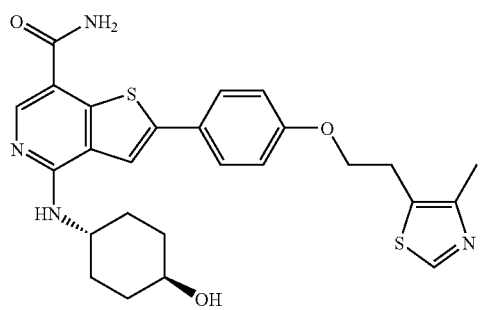

123

4-(trans-4'-Hydroxycyclohexylamino)-2-(4"-methylthiazolethoxyphenyl)-thieno[3,2-c]pyridine 7-carboxylic acid amide (123) was prepared from 4-methyl-5-thiazoleethanol and 4-(trans-4'-hydroxycyclohexylamino)-2-bromothieno[3,2-c]pyridine 7-carboxylic acid amide (118) by a three-step procedure analogous to that used in Example 39.

$^1$H NMR (300 MHz, DMSO) δ, 1.18-1.45 (m, 4H), 1.78-1.96 (m, 4H), 2.25 (3H, s), 3.14 (2H, t), 3.81 (1H, br s), 4.11 (2H, t), 6.99 (2H, d), 7.57 (1H, d), 8.14 (2H, d), 8.13 (2H, br s), 8.35 (1H, s), 8.75 (1H, br s). The signal for the remaining proton is obscured by the DMSO peak at 3.2-3.6 ppm. MS (EI) m/z (M+H$^+$) 509.

Example 41

Preparation of 4-(4'-trans-hydroxycyclohexylamino)-2-[4"-(phenylacetonitrile)phenyl]-thieno[3,2-c]pyridine-7-carboxylic acid amide (126).

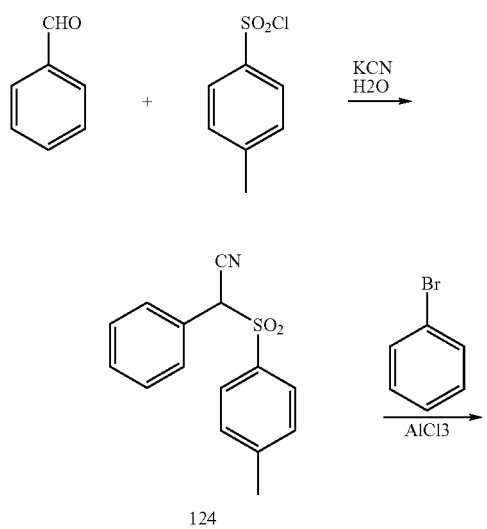

124

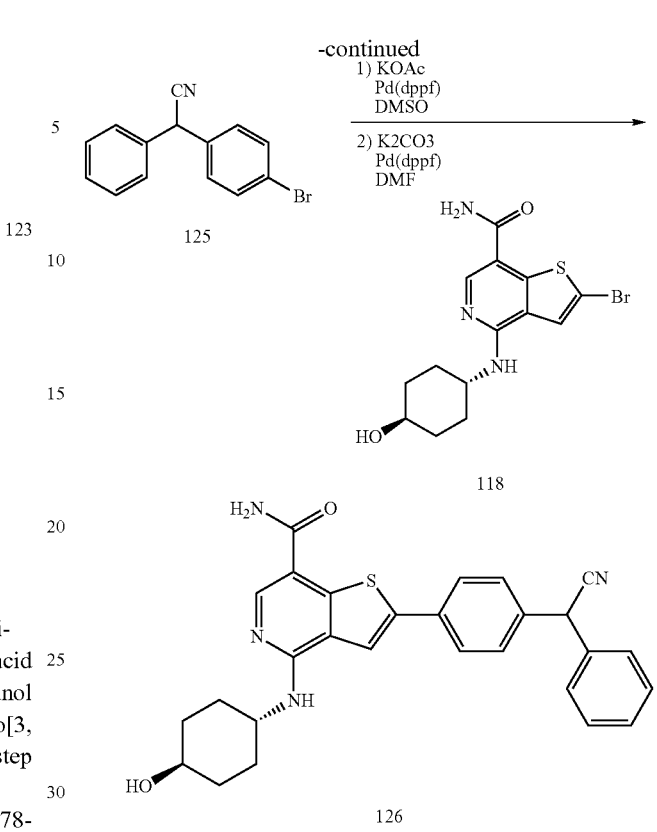

1-(4'-Toluenesulfonyl)-1-phenylacetonitrile (124). A solution of benzaldehyde (5 g, 47.1 mmol) and tosyl chloride (8.98 g, 47.1 mmol) was cooled to 0° C. A solution of potassium cyanide (3.06 g, 47 mmol) in water (10 mL) was added dropwise maintaining temperature below 5° C. After addition a white precipitate formed, the mixture was left to stir at room temperature for 30 min. The precipitate was collected by filtration and recrystallized by taking up in acetone/ethanol/diethyether (2:2:1-200 mL) to the solution was added ice (200 mL) and left to warm overnight. The resulting precipitate was collected by filtration to give the desired product (12.3 g). $^1$H NMR (300 MHz, d$^1$-CDCl$_3$) δ: 7.9 (d, 2H), 7.4 (m, 7H), 6.1 (s, 1H), 2.5 (s, 3H).

1-(4'-Bromophenyl)-1-phenylacetonitrile (125). A mix of 1-(4'-toluenesulfonyl)-1-phenylacetonitrile (124) (3 g, 11 mmol) and bromobenzene (5 g, 32 mmol) was cooled to 0° C. and aluminium chloride added portionwise. The mixture was then heated to 90° C. for 3 h. The mixture was left to cool and poured onto ice. The mixture was partitioned between ethyl acetate. The organics were washed with saturated sodium hydrogencarbonate (2×), brine, dried (MgSO$_4$) and concentrated to dryness. The mixture was purified by chromatography eluting with 5% EtOAc/Hexane to give the desired product (125) (0.77 g). $^1$H NMR (300 MHz, dl-CDCl$_3$) δ: 7.5 (d, 2H), 7.4 (m, 5H), 7.25 (d, 2H), 5.1 (s, 1H)

4-(4'-trans-Hydroxycyclohexylamino)-2-[4"-(phenylacetonitrile)phenyl]-thieno[3,2-c]pyridine-7-carboxylic acid amide (126). A mixture of 1-(4'-bromophenyl)-1-phenylacetonitrile (125) (0.77 g, 2.8 mmol), potassium acetate (0.83 g, 8.4 mmol), bis(pinacolato)diboron (0.79 g, 3.1 mmol) in dimethylsulfoxide (5 mL) was degassed (argon). To the mix was added 1,1'-bis(diphenylphosphino)ferrocene-palladium(II) dichloride dichloromethane complex (25 mg) and heated to 90° C. for 2 h. The mixture was partitioned between EtOAc/ brine (2×), dried (MgSO$_4$) and concentrated to dryness. The residue was treated with 4-(4'-trans-hydroxycyclohexylamino)-2-bromo-thieno[3,2-c]pyridine-7-carboxylic acid amide (118), prepared as described in Example 38, (0.75 equiv.), potassium carbonate (0.75 equiv.) and 1,1'-bis(diphenylphosphino)ferrocene-palladium(II)dichloride dichloromethane complex (5 mol %) in dimethylformamide (2 mL) and heated to 80° C. overnight. The mixture was left to cool and partitioned between EtOAc/brine (2×), dried (MgSO$_4$) and concentrated to dryness. The mixture was purified by chromatography eluting with 10% MeOH/DCM to give a mixture which was further purified by reverse phase chromatography to give desired product (0.1 g). $^1$H NMR (300 MHz, d$^6$-DMSO) δ: 8.5 (s, 1H), 8.4 (s, 1H), 8.0 (d, 1H), 7.9 (d, 2H), 7.6 (d, 2H), 7.5 (d, 3H), 7.4 (d, 1H), 6.0 (s, 1H), 4.0 (m, 2H), 2.0 (m, 4H), 1.4 (m, 4H). MS (EI) m/z (M+H$^+$) 483

Example 42

This example provides an assay that is useful in evaluating and selecting a compound that modulates IKK.

Assay Protocol for Measuring IKKβ Enzyme Inhibition 96 well polystyrene microtiter plates were coated with Neutravidin (10 μg/mL in PBS, overnight at 4° C.). The coating solution was removed and in 80 μL/well a kinase reaction mixture was added (20 mM Tris-HCl, pH 7.5, 10 mM MgCl$_2$, 2 mM EGTA, 1 mM NaF, 0.5 mM benzamidine, 1 mM DTT, 0.1% NP-40, 10 μM ATP, 1 μM of biotinylated substrate peptide KKERLLDDRHDS-GLDSMKDEEYEQGK-bio, sequence derived from IκBα). In 10 μL/well in DMSO test compounds were added covering a final concentration range from 1 nM to 30 μM. Recombinant full-length IKKβ enzyme produced in a baculovirus system in insect cells was added in 10 μL buffer containing Tris-HCl pH 7.5 20 mM, EGTA 2 mM, benzamidine 0.5 mM, DTT 1 mM, NP-40 0.1%, MgCl$_2$ 10 mM to initiate the kinase reaction. The reaction mixture was incubated at room temperature for 45 min. During this incubation the substrate peptide gets phosphorylated by IKKβ and gets captured onto the well's surface by Neutravidin. The plate was washed 3× with 150 μL distilled water to terminate the reaction and remove components of the reaction mixture.

A conventional chemiluminescent ELISA detection technique was initiated by adding 100 μL/well primary antibody (custom-made monoclonal antibody generated to recognize the phosphorylated epitope in the substrate peptide; used at 1:10,000 dilution) premixed with horseradish peroxidase (HRP) conjugated anti-mouse secondary antibody (commercially available from several sources; used at 1:10,000 dilution) in PBS containing 2% BSA. The solution was incubated at room temperature for 40 min on a shaker, then washed 3× with 150 μL of water. 100 μL/well 10× diluted SuperSignal HRP substrate (from Pierce) was added and after 5 min incubation the chemiluminescent signal was captured by a Labsystems LuminoSkan luminometer. The point of 50% inhibition of IKKβ enzyme activity (IC$_{50}$) was determined by curve fitting with the LSW data analysis software (MDL, San Leandro, Calif.).

The compounds provided in Examples 1-25 all displayed IC$_{50}$ values of 10 μM or less in the above assay.

Example 44

This example provides an assay that is useful in evaluating and selecting a compound that modulates IRAK-1 or IRAK-4.

Assay Protocol for Measuring IRAK-1 or IRAK-4 Enzyme Inhibition 96-well polystyrene microtiter plates were coated with neutravidin for IRAK-1 or streptavidin for IRAK-4 (10 mg/mL in PBS, overnight at 4° C.). The coating solution was removed and in 80 μL/well a kinase reaction mixture was added (for IRAK-1: 20 mM Tris-HCl, pH 7.5, 10 mM MgCl$_2$, 2 mM EGTA, 1 mM NaF, 0.5 mM benzamidine, 1 mM DTT, 3 μM ATP, 1 mM of biotinylated substrate peptide bio-ARF-SRFAGSSPSQSSMVAR, sequence derived from IRAK-1; for IRAK-4: 20 mM Tris-HCl, pH 7.5, 10 mM MgCl$_2$, 2 mM EGTA, 1 mM NaF, 0.5 mM benzamidine, 1 mM DTT, 10% glycerol, 10 μM ATP, 1 mM of biotinylated substrate peptide bio-RRRVTSPARRS, sequence derived from GFAP).

At 10 μL/well in DMSO test compounds were added covering a final concentration range from 1 nM to 30 μM. Recombinant, full-length IRAK-1 or 1-4 enzyme (baculovirus expression system) was added in 10 μL buffer containing Tris-HCl pH 7.5 20 mM, EGTA 2 mM, benzamidine 0.5 mM, DTT 1 mM, MgCl$_2$ 10 mM and glycerol 10% (IRAK-4 only) to initiate the kinase reaction. The reaction mixture was incubated at room temperature for 60 min. on a shaker. During this incubation the substrate peptide is being phosphorylated by the kinase and gets captured onto the surface of the wells by neutravidin or streptavidin, respectively. The plate was washed 3× with 150 μL distilled water to terminate the reaction and remove components of the reaction mixture.

A conventional chemiluminescent ELISA detection technique was initiated by adding 100 μL/well primary antibody (monoclonal antibody YC10, generated to recognize the phosphorylated epitope in the substrate peptide; used at 1:20,000 dilution for IRAK-1 and 1:10,000 dilution for IRA-4) premixed with horseradish peroxidase (HRP) conjugated anti-mouse secondary antibody (commercially available from several sources; used at 1:10,000 dilution) in PBS containing 2% BSA. The solution was incubated at room temperature for 40 min. on a shaker, then washed 3× with 150 μL of water. 100 μL/well 10× diluted SuperSignal HRP substrate (from Pierce) was added and after 5 min. incubation the chemiluminescent signal was captured by a Labsystems LuminoSkan luminometer. The point of 50% inhibition of IRAK-1 or IRAK-4 enzyme activity (IC$_{50}$) was determined by curve fitting with the LSW data analysis software (MDL, San Leandro, Calif.).

The compounds provided in Examples 26-42 all displayed IC$_{50}$ values of 10 μM or less in the above assay.

Sequences

IRAK-1 has an N-terminal Flag tag for purification. IRAK-4 has an N-terminal His Tag. An amino acid spacer is between Tag and the kinase.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this inven-

What is claimed is
1. A compound having the formula (Ia.1):

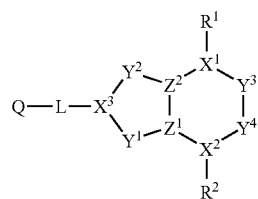

Ia.1 or a pharmaceutically acceptable salt thereof, wherein
$R^1$ is selected from the group consisting of —C(O)NR$^{1a}$R$^{1b}$, —C(O)R$^{1a}$, —CH(=NOH), —N(R$^{1b}$)C(O)R$^{1a}$, —SO$_2$NR$^{1a}$R$^{1b}$, —SO$_2$R$^{1a}$, —C(O)N(R$^{1a}$)OR$^{1b}$, —(C$_1$-C$_4$)alkylene-N(R$^{1b}$)C(O)R$^{1a}$, and —(C$_1$-C$_4$)alkylene-C(O)NR$^{1a}$R$^{1b}$; wherein R$^{1a}$ and R$^{1b}$ are selected from hydrogen, (C$_1$-C$_6$)alkyl, (C$_2$-C$_4$)alkenyl, (C$_2$-C$_6$)heteroalkyl, hydroxy(C$_1$-C$_4$)alkyl, fluoro(C$_1$-C$_4$)alkyl, cyano(C$_1$-C$_4$)alkyl, cyclo(C$_3$-C$_8$)alkyl, and mono- or di-hydroxycyclo(C$_3$-C$_8$)alkyl;
$R^2$ is selected from the group consisting of —C(O)NR$^{2a}$R$^{2b}$ and —OH; wherein R$^2$a and R$^{2b}$are selected from hydrogen, (C$_1$-C$_6$)alkyl, (C$_2$-C$_4$)alkenyl, (C$_2$-C$_6$)heteroalkyl, mono- or di-hydroxy(C$_1$-C$_4$)alkyl, fluoro(C$_1$-C$_4$)alkyl, cyano(C$_1$-C$_4$)alkyl, cyclo(C$_3$-C$_8$)alkyl, mono- or di-hydroxycyclo(C$_3$-C$_8$)alkyl, aryl, aryl(C$_1$-C$_4$)alkyl, —C(O)—(C$_1$-C$_4$)alkyl, —C(O)—(C$_1$-C$_4$)alkoxy, and C(O)-fluoro(C$_1$-C$_4$)alkyl;
L is a single bond;
Q is selected from the group consisting of(C$_2$-C$_6$)alkenyl, (C$_2$-C$_6$)alkynyl, (C$_1$-C$_6$)alkoxy, aryl, aryl(C$_1$-C$_4$)alkyl, cyclo(C$_3$-C$_8$)alkyl, and cyclo(C$_5$-C$_8$)alkenyl, wherein each of the moieties is optionally further substituted,
$X^1$, $X^2$ and $X^3$ are independently selected from the group consisting of =C—, and —CH—;
$Y^2$ is —S(O)$_m$—;
$Y^1$ and $Y^3$ are independently selected from the group consisting of =C(R$^{5a}$)—, and —C(R$^5$)(R$^6$)—;
$Y^4$ is =N— or —N(R$^5$)—;
$Z^1$ and $Z^2$ are independently CH, or =C—;
each $R^5$ and $R^6$ is independently selected from the group consisting of hydrogen, (C$_1$-C$_6$)alkyl, cyclo(C$_3$-C$_8$)alkyl, aryl, aryl(C$_1$-C$_4$)alkyl, hetero(C$_1$-C$_6$)alkyl, and arylhetero(C$_1$-C$_4$)alkyl;
each $R^{5a}$ is independently selected from the group consisting of hydrogen, halogen, (C$_1$-C$_6$)alkyl, cyclo(C$_3$-C$_8$)alkyl, aryl, aryl(C$_1$-C$_4$)alkyl, hetero(C$_1$-C$_6$)alkyl, and arylhetero(C$_1$-C$_4$)alkyl; and
the subscript m is 0;
with the proviso that said compound is other than

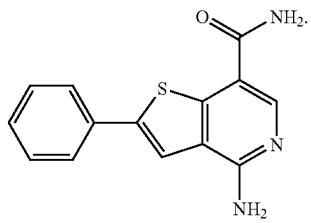

2. The compound of claim 1, wherein Q is selected from the group consisting of phenyl, naphthyl, cyclopentyl and cyclohexyl.

3. The compound of claim 1, wherein Q is unsubstituted phenyl or phenyl substituted with from 1 to 3 substituents selected from the group consisting of halogen, cyano. nitro, cyano(C$_2$-C$_6$)alkenyl, nitro(C$_2$-C$_6$)alkenyl, —R', —OR', —NR'R", —C(O)R', —CO$_2$R', —C(O)NR'R", —NR"C(O)R', —NR"CO$_2$R', —NR'C(O)NR"R'", —S(O)R', —SO$_2$R, —SO$_2$NR'R", —NR"SO$_2$R', —OC(O)NR'R", —X—C(O)R', —X—CO$_2$R', —X—C(O)NR'R", —X—NR"C(O)R', —X—NR"CO$_2$R', —X—NR'C(O)NR"R'", —X—S(O)R', —X—SO$_2$R', —X—SO$_2$NR'R", —X—NR"SO$_2$R' and —X—OC(O)NR'R", and optionally R' or R"is attached to an adjacent ring atom on the phenyl group to form a 5- or 6-membered fused ring;
(a) wherein
(b) X is (C$_1$-C$_6$)alkylene; and
R', R" and R'" are independently selected from the group consisting of hydrogen, (C$_1$-C$_6$)alkyl, (C$_2$-C$_4$)alkenyl, (C$_1$-C$_6$)heteroalkyl, hydroxy(C$_1$-C$_4$)alkyl, fluoro(C$_1$-C$_4$)alkyl, cyano(C$_1$-C$_4$)alkyl, cyano(C$_1$-C$_4$)haloalkyl, cyclo(C$_3$-C$_8$)alkyl, mono- or di-hydroxycyclo(C$_3$-C$_8$) alkyl, heterocyclo(C$_3$-C$_8$)alkyl, heterocyclo(C$_3$-C$_8$) alkyl-(C$_1$-C$_4$)alkyl, aryl, aryl(C,-C$_4$)alkyl, heteroaryl, heteroaryl(C$_1$-C$_4$)alkyl, —C(O)—(C$_1$-C$_4$)alkyl, —C(O)—(C$_1$-C$_4$)alkoxy, —C(O)-heterocyclo(C$_3$-C$_8$) alkyl and —C(O)-fluoro(C$_1$-C$_4$)alkyl; and optionally, any two of R', R"and R'" can be combined with their intervening atom(s) to form a 5-, 6- or 7-membered ring containing from 1-3 heteroatoms selected from N, O and S.

4. The compound of claim 1, wherein $R^1$ is selected from the group consisting of —C(O)NR$^{1a}$R$^{1b}$, —SO$_2$NR$^{1a}$R$^{1b}$, —SO$_2$R$^{1a}$R$^{1b}$, —SO$_2$R$^{1a}$, and —C(O)R$^{1a}$.

5. The compound of claim 1, having the formula (III):

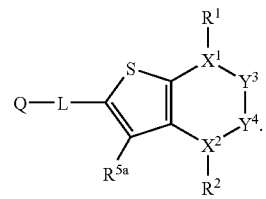

III

6. The compound of claim 1, having the formula (V):

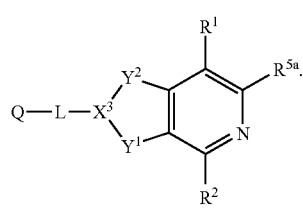

V

7. The compound of claim 1, having the formula (VI):

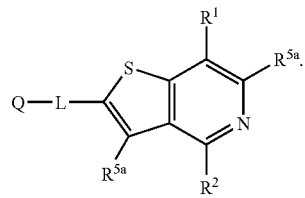

wherein each $R^{5a}$ is independently from the group consisting of hydrogen, halogen, ($C_1$-$C_6$)alkyl, cyclo($C_3$-$C_8$)alkyl, aryl, aryl($C_1$-$C_4$)alkyl, hetero($C_1$-$C_6$)alkyl, and arylhetero($C_1$-$C_4$)alkyl.

8. The compound of claim 7, wherein $R^2$ is —$NHR^{2b}$.

9. The compound of claim 7, wherein $R^1$ is selected from the group consisting of —C(O)$NHR^{1a}$, —$SO_2NHR^{1a}$, —$SO_2R^{1a}$ and —C(O)$CH_3$ and $R^2$ is —$NHR^{2b}$.

10. The compound of claim 7, wherein $R^1$ is selected from the group consisting of —C(O)$NHR^{1a}$, —$SO_2NHR^{1a}$, —$SO_2R^{1a}$ and —C(O)$CH_3$, $R^2$ is —$NHR^{2b}$ and each $R^{5a}$ is hydrogen.

11. The compound of claim 10, selected from the group consisting of:

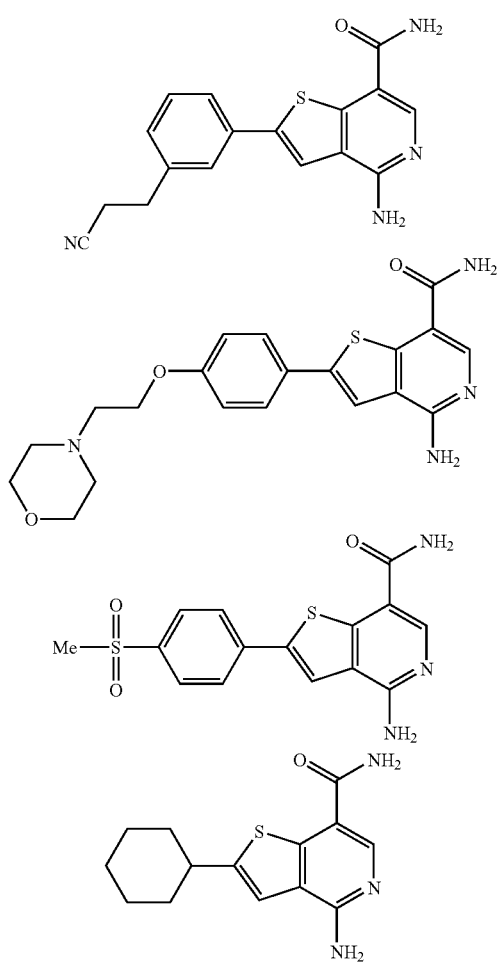

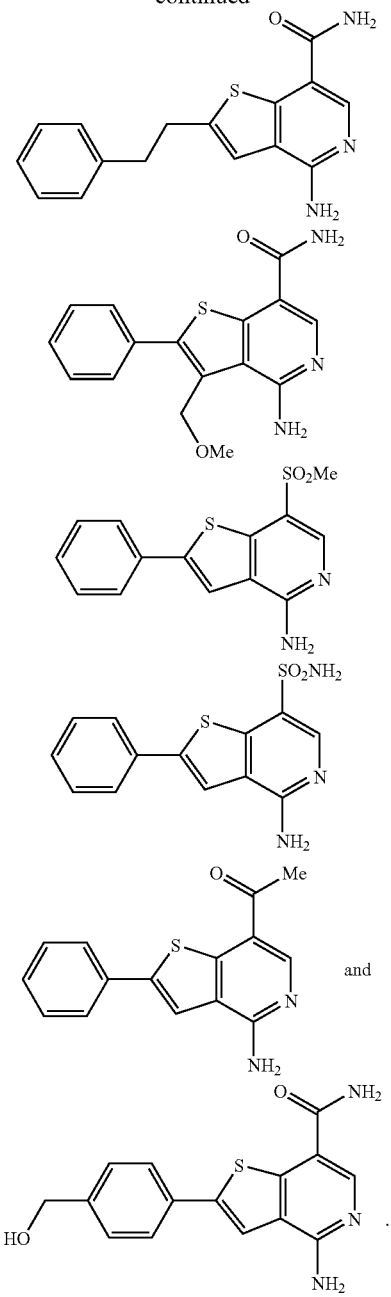

12. A pharmaceutical composition comprising a pharmaceutically acceptable carrier, excipient or diluent and a compound of claim 1.

13. A method for treating an inflammatory, metabolic or immune disease or condition selected from rheumatoid arthritis, inflammatory bowel disease, psoriasis, type 1 diabetes, type 2 diabetes, asthma, multiple sclerosis and graft rejection said method comprising administering to a subject in need thereof a therapeutically effective amount of a compound of claim 1.

14. The method of claim 13, wherein said compound is administered orally, topically, intravenously or intramuscularly.

15. The method of claim 13, wherein said compound is administered in combination with a second therapeutic agent selected from the group consisting of prednisone, dexamethasone, beclomethasone, methylprednisone, betamethasone, hydrocortisone, methotrexate, cyclosporin, rapamycin, tacrolimus, an antihistamine, a TNF antibody, an IL-1 antibody, a soluble TNF receptor, a soluble IL-1 receptor, a TNF or IL-1 receptor antagonist, a non-steroidal antiinflammatory agent, a COX-2 inhibitor, an antidiabetic agent, an anticancer agent, hydroxycloroquine, D-penicillamine, infliximab, etanercept, auranofin, aurothioglucose, sulfasalazine, sulfasalazine analogs, mesalamine, corticosteroids, corticosteroid analogs, 6-mercaptopurine, interferon β-1β, interferon β-1α, azathioprine, glatiramer acetate, a glucocorticoid and cyclophosphamide.

16. A method for modulating IKK, comprising contacting a cell with a compound of claim 1.

17. The method of claim 16, wherein said compound inhibits IKK.

18. The method of claim 16, wherein said compound inhibits IKKβ.

19. The method of claim 16, wherein said compound inhibits IKKβ and IKKα.

20. The compound of claim 1, selected from the group consisting of:

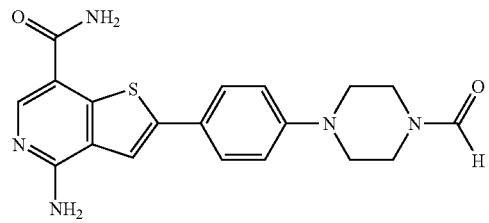

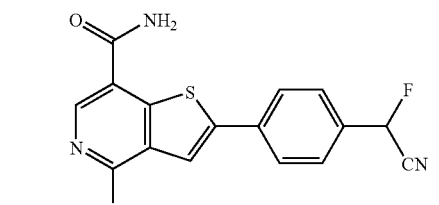

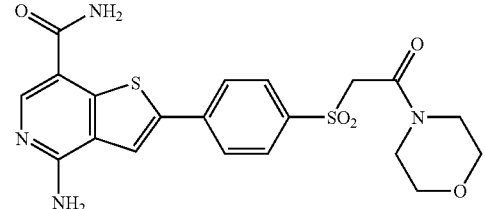

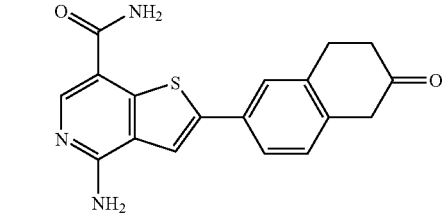

-continued

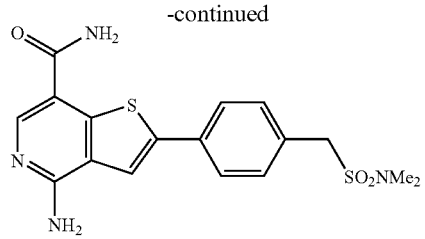

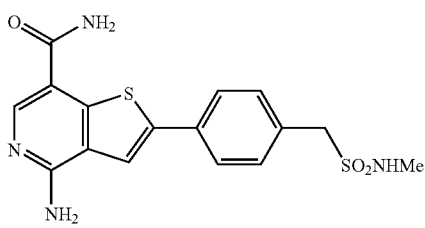

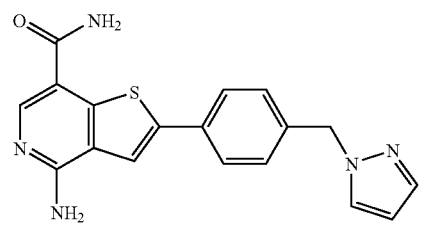

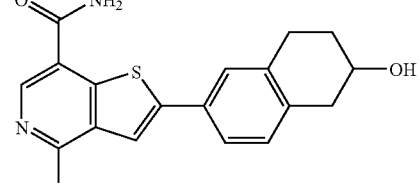

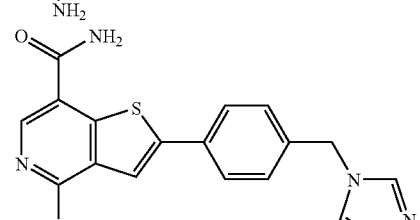

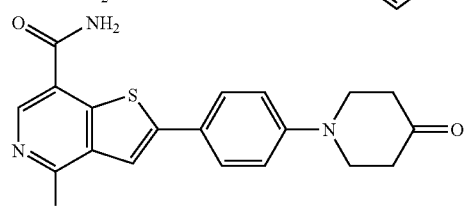

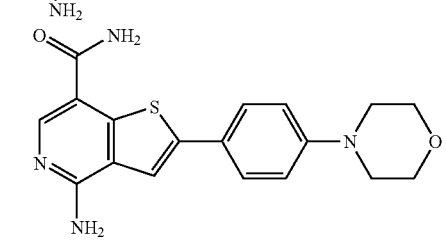

99
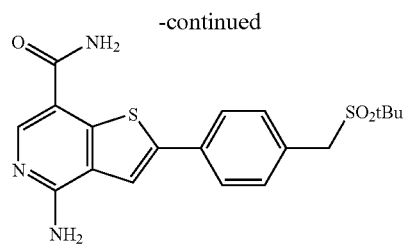
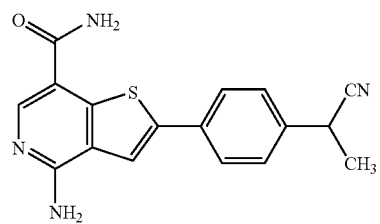
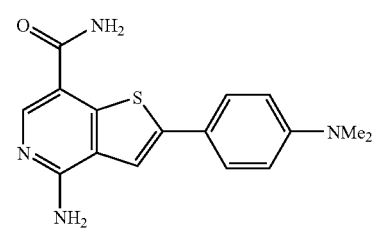
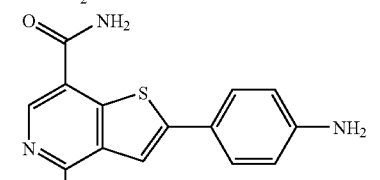
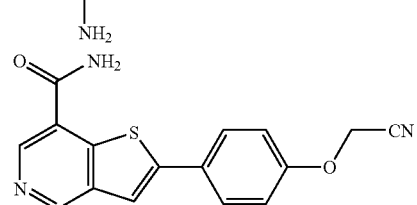
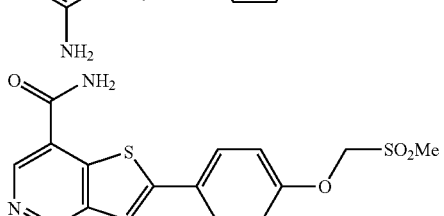
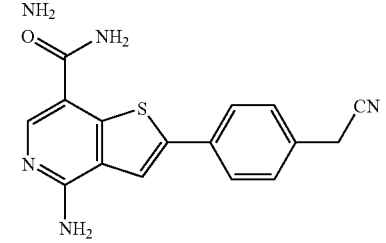
100
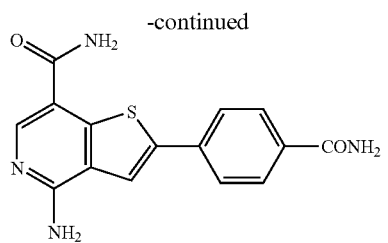
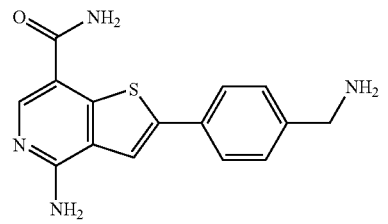
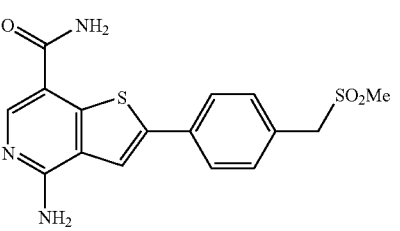
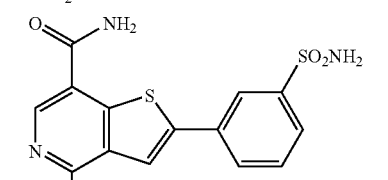
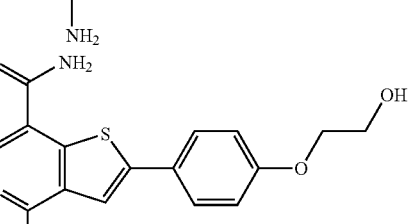
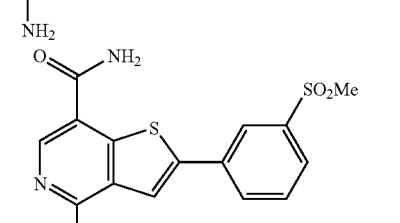
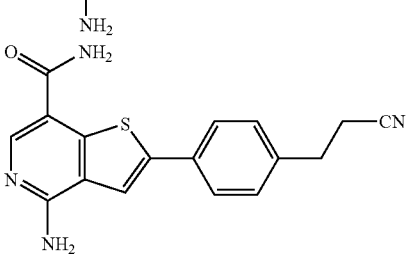

101
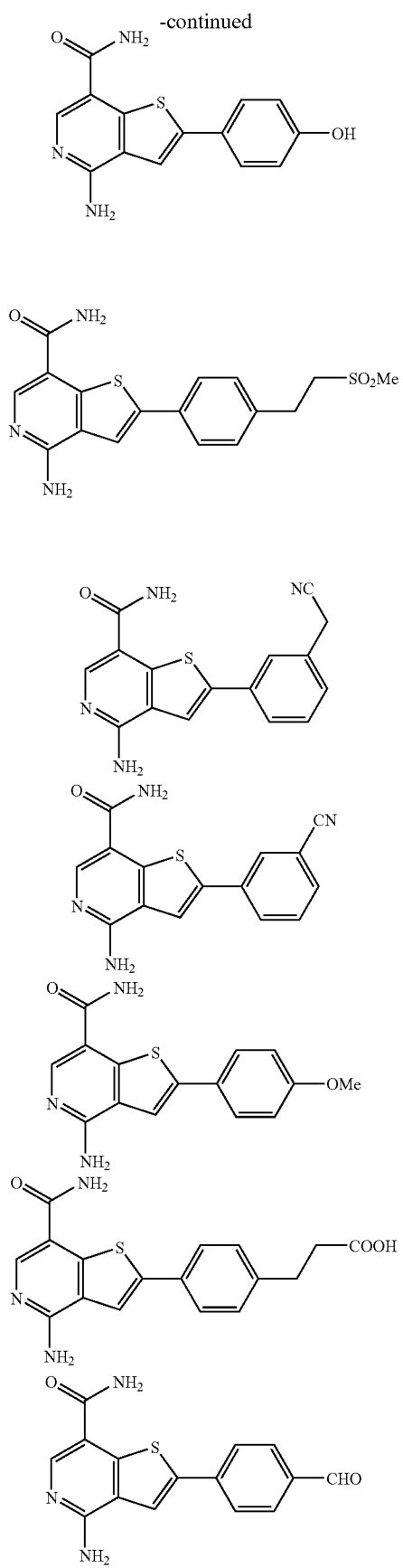
102
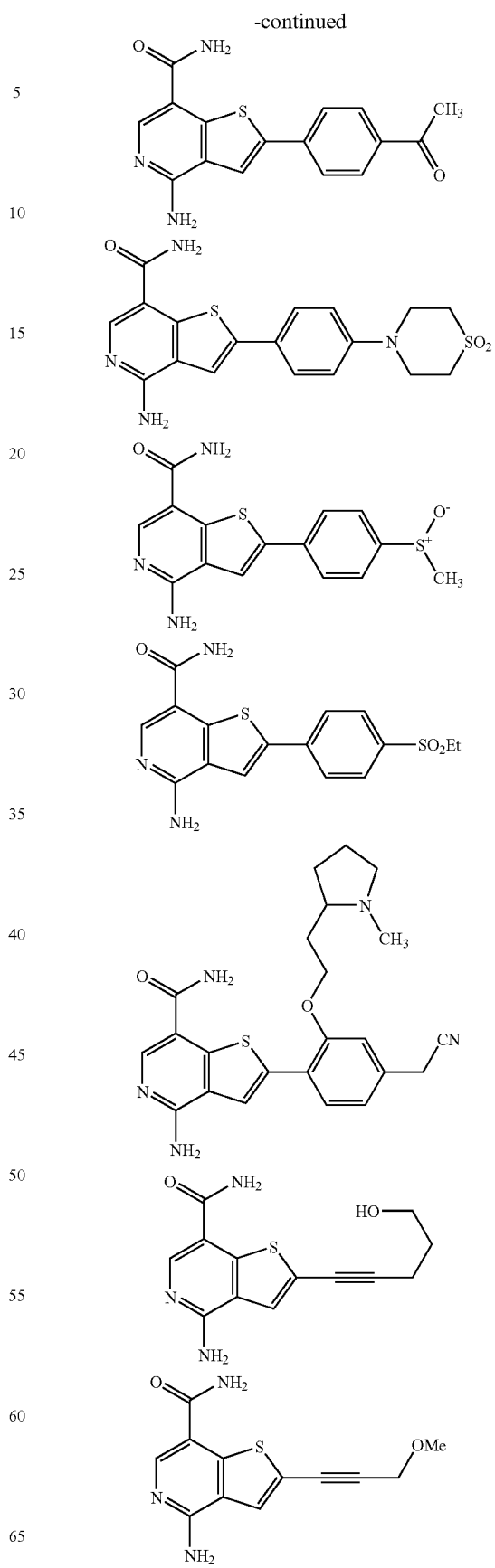

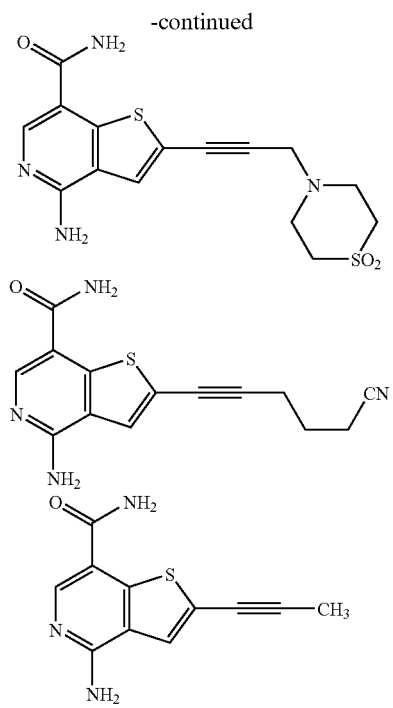
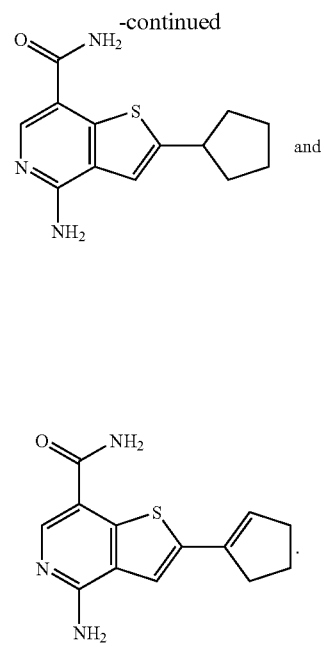

UNITED STATES PATENT AND TRADEMARK OFFICE
CERTIFICATE OF CORRECTION

| | | |
|---|---|---|
| PATENT NO. | : 7,635,695 B2 | Page 1 of 1 |
| APPLICATION NO. | : 11/709895 | |
| DATED | : December 22, 2009 | |
| INVENTOR(S) | : Burkitt et al. | |

It is certified that error appears in the above-identified patent and that said Letters Patent is hereby corrected as shown below:

Claim 1, lines 28-29, replace "-C(O)-NR$^{2a}$R$^{2b}$" with --NR$^{2a}$R$^{2b}$--;

Claim 1, line 38, replace "(C$_1$-C$_6$)alkoxy, aryl," with --(C$_1$-C$_6$)alkoxy, halogen, aryl--;

Claim 3, line 9, replace "-SO$_2$R" with --SO$_2$R'--;

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,635,695 B2  Page 1 of 1
APPLICATION NO. : 11/709895
DATED : December 22, 2009
INVENTOR(S) : Burkitt et al.

It is certified that error appears in the above-identified patent and that said Letters Patent is hereby corrected as shown below:

Column 93, Claim 1, lines 28-29, replace "-C(O)-NR$^{2a}$R$^{2b}$" with --NR$^{2a}$R$^{2b}$--;

Column 93, Claim 1, line 38, replace "(C$_1$-C$_6$)alkoxy, aryl," with --(C$_1$-C$_6$)alkoxy, halogen, aryl--;

Column 94, Claim 3, line 9, replace "-SO$_2$R" with --SO$_2$R'--;

This certificate supersedes the Certificate of Correction issued May 25, 2010.

Signed and Sealed this

Twenty-second Day of June, 2010

David J. Kappos
*Director of the United States Patent and Trademark Office*